(12) United States Patent
Wagner et al.

(10) Patent No.: US 10,639,307 B2
(45) Date of Patent: May 5, 2020

(54) METHODS RELATING TO THE DIAGNOSIS AND TREATMENT OF PREECLAMPSIA COMPRISING ADMINISTRATION OF ADAMTS13 POLYPEPTIDES

(71) Applicant: CHILDREN'S MEDICAL CENTER CORPORATION, Boston, MA (US)

(72) Inventors: Denisa D. Wagner, Dover, MA (US); Luise Erpenbeck, Boston, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 18 days.

(21) Appl. No.: 15/573,842

(22) PCT Filed: May 13, 2016

(86) PCT No.: PCT/US2016/032305
§ 371 (c)(1),
(2) Date: Nov. 14, 2017

(87) PCT Pub. No.: WO2016/186994
PCT Pub. Date: Nov. 24, 2016

(65) Prior Publication Data
US 2018/0256571 A1 Sep. 13, 2018

Related U.S. Application Data

(60) Provisional application No. 62/162,151, filed on May 15, 2015.

(51) Int. Cl.
| | | |
|---|---|---|
| *A61K 31/506* | (2006.01) | |
| *A61K 38/36* | (2006.01) | |
| *A61K 45/06* | (2006.01) | |
| *A61K 31/404* | (2006.01) | |
| *A61K 31/4412* | (2006.01) | |
| *A61P 7/02* | (2006.01) | |
| *A61K 38/17* | (2006.01) | |
| *A61P 43/00* | (2006.01) | |
| *A61P 13/12* | (2006.01) | |
| *A61P 35/00* | (2006.01) | |

(52) U.S. Cl.
CPC .......... *A61K 31/506* (2013.01); *A61K 31/404* (2013.01); *A61K 31/4412* (2013.01); *A61K 38/1767* (2013.01); *A61K 38/36* (2013.01); *A61K 45/06* (2013.01); *A61P 7/02* (2018.01); *A61P 13/12* (2018.01); *A61P 35/00* (2018.01); *A61P 43/00* (2018.01)

(58) Field of Classification Search
None
See application file for complete search history.

(56) References Cited

U.S. PATENT DOCUMENTS

| | | | |
|---|---|---|---|
| 7,501,117 B2 | 3/2009 | Laemmle et al. | |
| 2001/0049106 A1 | 12/2001 | Buckbinder et al. | |
| 2002/0090373 A1 | 7/2002 | Buckbinder et al. | |
| 2003/0073116 A1 | 4/2003 | Ginsburg et al. | |
| 2003/0166899 A1 | 9/2003 | Buckbinder et al. | |
| 2004/0185042 A1* | 9/2004 | Scheiflinger .......... | C07K 14/755 424/140.1 |
| 2007/0015703 A1 | 1/2007 | Wagner et al. | |
| 2009/0202517 A1 | 8/2009 | Yoneyama et al. | |
| 2010/0022452 A1 | 1/2010 | Silence | |
| 2013/0344073 A1 | 12/2013 | Schwaeble et al. | |
| 2014/0056888 A1 | 2/2014 | Zhou | |

FOREIGN PATENT DOCUMENTS

| | | | |
|---|---|---|---|
| EP | 1568782 A1 | 8/2005 | |
| WO | WO 02/42441 | * 5/2002 | .............. C12N 9/64 |
| WO | WO 2006/133955 | * 12/2006 | .............. C12Q 1/37 |

OTHER PUBLICATIONS

Kokama et al., PNAS, 2002; 99: 11902-11907 (Year: 2002).*
Bhattacharya et al., PLoS ONE 12(3): e0171355. https://doi.org/10.1371/journal.pone.0171355; 22 pages total (Year: 2017).*
Tokuriki and Tawflik, Current Opinion in Structural Biology 2009, 19: 596-604 (Year: 2009).*
Piche-Nicholas et al., MAbs. 2018; 10: 81-94. doi: 10.1080/19420862.2017.1389355 (Year: 2018).*
Phillips, A., J Pharm Pharmacology, 2001; 53: 1169-1174 (Year: 2001).*
Winkler, Ther. Deliv. 2013; 4: 791-809 (Year: 2013).*
Jafarlou et al., Journal of Biological Regulators & Homeostatic Agents, 2016: 30: 315-321 (Year: 2016).*
McMinn and George, Journal of Clinical Apheresis, 2001; 16: 202-209 (Year: 2001).*
The Fuchs abstract (Blood, Nov. 19, 2010 vol. 116, No. 21. Abstract No. 1437. Presented at: 52nd Annual Meeting of the American Society of Hematology, ASH 2010. Orlando, FL, United States (Year: 2010).*
Eremina et al., NEJM, 2008; 358: 1129-36 (Year: 2008).*
Maynard et al., J. Clin. Invest. 2003; 111: 649-658 (Year: 2003).*
Cardones and Bañez, Current Pharmaceutical Design, 2006; 12: 387-394 (Year: 2006).*
Plaimauer et al., "Cloning, expression, and functional characterization of the von Willebrand factor-cleaving protease (ADAMTS13)." Blood 100(10):3626-3632 (2002).
Plaimauer et al., "Expression and characterization of recombinant human ADAMTS-13." Seminars in Hematology 41(1)24-33 (2004).
Andoh et al., "Increased aggregation response of platelets in patients with inflammatory bowel disease.", J. Gastroenterol., 41(1):47-54 (2006).
Aref et al., "Increased VWF antigen levels and decreased ADAMTS13 activity in preeclampsia." Hematology 18:237-241 (2013).

(Continued)

*Primary Examiner* — Christina M Borgeest
(74) *Attorney, Agent, or Firm* — Nixon Peabody LLP; David S. Resnick; Nicole D. Kling

(57) ABSTRACT

Described herein are methods, assays, and compositions relating to the treatment of thrombosis, preeclampsia, cancer, and intestinal inflammation, e.g., by administering ADAMTS13 to a subject in need of treatment.

5 Claims, 22 Drawing Sheets
Specification includes a Sequence Listing.

(56) References Cited

OTHER PUBLICATIONS

Blake-Haskins et al., "Thrombotic microangiopathy with targeted cancer agents", Clin Cancer Res. 17(18):5858-5866 (2011).
Chang et al., "Thrombotic microangiopathy and the kidney: a nephropathologist's perspective." Diagnostic Histophatology 19(5):158-65 (2013).
Chauhan et al., "ADAMTS13: a new link between thrombosis and inflammation.", J. Exp. Med., 205(9):2065-2074 (2008).
Chen et al., "N-acetylcysteine reduces the size and activity of von Willebrand factor in human plasma and mice." The Journal of clinical investigation 121(2):593-603 (2011).
Coppo et al., "Thrombotic microangiopathies: towards a pathophysiology-based classification", Cardiovasc Hematol Disord Drug Targets 9(1):36-50 (2009).
Danese et al., "Inflammation and coagulation in inflammatory bowel disease: The clot thickens.", Am. J. Gastroenterol., 102(1):174-86 (2007).
Dhillon et al. "Mucosal capillary thrombi in rectal biopsies", Histopathology 21(2): 127-133 (1992).
Dong et al., "ADAMTS-13 rapidly cleaves newly secreted ultralarge von Willebrand factor multimers on the endothelial surface under flowing conditions", Blood 100(12):4033-4039 (2002).
Ekaney et al., "Preserved Expression of mRNA Coding von Willebrand Factor-Cleaving Protease ADAMTSI3 by Selenite and Activated Protein C", Molecular Medicine 21:355-363 (2015).
Eremina et al., "Biology of anti-angiogenic therapy-induced thrombotic microangiopathy." Seminars in Nephrology 30(6):582-590 (2010).
Esmon "The impact of the inflammatory response on coagulation.", Thrombosis Research, 114(5-6):321-327 (2004).
Feagan et al., "Vedolizumab as induction and maintenance therapy for ulcerative colitis", N Engl J. Med. 369(8):699-710 (2013).
Feys et al., "ADAMTS13 activity to antigen ratio in physiological and pathological conditions associated with an increased risk of thrombosis.", Br. J. Haematol., 138(4):534-540 (2007).
Feys et al., "Inhibition of von Willebrand factor-platelet glycoprotein Ib interaction prevents and reverses symptoms of acute acquired thrombotic thrombocytopenic purpura in baboons." Blood 120:3611-3614 (2012).
George et al., "Ten patient stories illustrating the extraordinarily diverse clinical features of patients with thrombotic thrombocytopenic purpura and severe ADAMTSI3 deficiency", Journal of Clinical Apheresis 27(6):302-311 (2012).
Harries et al., "Platelet count: a simple measure of activity in Crohn's disease.", Br. Med. J., 286(6376):1476 (1983).
Ippolito et al. "An integrated assessment of histopathological changes of the enteric neuromuscular compartment in experimental colitis.", JCellMolAfed 19(2): 485-500 (2015).
Jilma-Stohlawetz et al., "A dose ranging phase I/II trial of the von Willebrand factor inhibiting aptamer ARC1779 in patients with congenital thrombotic thrombocytopenic purpura" Thrombosis and haemostasis 106:539-547 (2011).
Lechner et al., "Acquired immune-mediated thrombophilia in lymphoproliferative disorders." Leukemia & Lymphoma 52:1836-1843 (2011).

Ley et al., "Getting to the site of inflammation: the leukocyte adhesion cascade updated", Nature Reviews Immunology 7(9):678-689 (2007).
Li et al., "Treatment of refractory thrombotic thrombocytopenic purpura with N-acetylcysteine: a case report." Transfusion 54:1221-1224 (2014).
Mannucci et al., "Patients with localized and disseminated tumors have reduced but measurable levels of ADAMTS-13 (von Willebrand factor cleaving protease)." Haematologica 88:454-458 (2003).
Matsumoto et al. "Possible role of vascular endothelial cells in immune responses in colonic mucosa exanlined immunocytochemically in subjects with and without ulcerative colitis.", Clin Exp Immunol. 78(3): 424-430 (1989).
Middleton et al. "A comparative study of endothelial cell markers expressed in chronically inflamed human tissues: MECA-79, Duffy antigen receptor for chemokines, von Willebrand factor, CD31, CD34, CD105 and CD146.", J Pathol 206(3): 260-268 (2005).
Owczarek et al., "Decreased plasma ADAMTSl3 antigen and ADAMTSl3 activity as a risk factor for hypercoagulability in patients with ulcerative colitis.", Journal of Crohns and Colitis, 9(suppl 1):S208-9 (2015).
Papay et al. "Clinical presentation of venous thromboembolism in inflammatory bowel disease.", Jcrohns Colitis 7(9):123-729 (2013).
Paueksakon et al., "Autopsy renal pathology." Surgical Pathology 7:321-355 (2014).
Piskernik et al., "Preclinical safety of Baxter's recombinant ADAMTS13." 54th ASH Annual Meeting and Exposition (Abstract) 3381 (2012).
Plaimauer et al. "Recombinant ADAMTSl3 normalizes von Willebrand factor-cleaving activity in plasma of acquired TTP patients by overriding inhibitory antibodies." J Thrombosis and Haemostasis. 9:936-944 (2011).
Sandborn et al., "Vedolizumab as induction and maintenance therapy for Crohn's disease", N Engl J Med. 369(8):711-721 (2013).
Stevens et al., "Circulating von Willebrand factor in inflammatory bowel disease.", Gut., 33(4):502-506 (1992).
Thompson et al. "Inherited disorders of coagulation appear to protect against inflammatory bowel disease.", Gastroenterology 108(4): 1011-1015 (1995).
Violi et al. "Prevalence and Clinical Importance of Mesenteric Venous Thrombosis in the Swiss Inflammatory Bowel Disease Cohort", AJR 203(1): 62-69 (2014).
Wagner, "Cell biology of von Willebrand factor", Annual Rev Cell Biology 6:217-246 (1990).
Yao et al., "Thrombotic thrombocytopenic purpura due to anti-ADAMTSl3 antibodies in multiple myeloma." Clinical nephrology 81(3):210-215 (2014).
Zezos et al., "Elevated plasma von Willebrand factor levels in patients with active ulcerative colitis reflect endothelial perturbation due to systemic inflammation.", WJG, 11(48):7639-7645 (2005).
Ahmed et al. "Correlation of Thrombotic Thrombocytopenic Purpura Disease Activity with Von Willibrand Factor Cleaving Protease Level in Ulcerative Colitis." The American J of Medicine 116(1): 786-787 (2004).

\* cited by examiner

SEQUENCE LISTING

```
<160> NUMBER OF SEQ ID NOS: 4

<210> SEQ ID NO 1
<211> LENGTH: 4966
<212> TYPE: DNA
<213> ORGANISM: Homo sapiens

<400> SEQUENCE: 1
aaccacgatg tctttggcac agcctctcat ctgtcagatg ggagcgggga ccccggagag      60
ggagtcagcc gaggtcctgg cattccttgt gaaccccgt ctgtgggttt ctggtccagt     120
gtcccttctc cagattagat ggcttaggcc tcctctaagg gggtgggcgt gcacatccgg    180
agagctgtct ggtgtgcagg actgggctgc aggttaccct gaactgcaac catcttagag    240
caaggcccag cttgcagcag gaggagctgc aggccgccca cctagccac ggcccctgcc     300 ctggcaggaa gcttccaaga gtaaacactg cctaatcgtc ccgcccagta gtgagcaggc    360
ctgtcccatt ccatactgac cagattccca gtcaccaagg cccctctca ctccgctcca    420 ctcctcgggc tggctctcct gaggatgcac cagcgtcacc cccgggcaag atgccctccc  480
ctctgtgtgg ccggaatcct tgcctgtggc tttctcctgg gctgctgggg accctcccat   540
ttccagcaga gttgtcttca ggctttggag ccacaggccg tgtcttctta cttgagccct    600
ggtgctccct taaaaggccg ccctccttcc cctggcttcc agaggcagag gcagaggcag    660
aggcgggctg caggcggcat cctacacctg gagctgctgg tggccgtggg ccccgatgtc    720
ttccaggctc accaggagga cacagagcgc tatgtgctca ccaacctcaa catcggggca     780
gaactgcttc gggacccgtc cctgggggct cagtttcggg tgcacctggt gaagatggtc    840
attctgacag agcctgaggg tgctccaaat atcacagcca acctcacctc gtccctgctg    900
agcgtctgtg ggtggagcca gaccatcaac cctgaggacg acacggatcc tggccatgct   960
gacctggtcc tctatatcac taggtttgac ctggagttgc ctgatggtaa ccggcaggtg   1020
cggggcgtca cccagctggg cggtgcctgc tccccaacct ggagctgcct cattaccgag    1080
gacactggct tcgacctggg agtcaccatt gcccatgaga ttgggcacag cttcggcctg    1140
gagcacgacg gcgcgcccgg cagcggctgc ggccccagcg gacacgtgat ggcttcggac    1200
ggcgccgcgc cccgcgccgg cctcgcctgg tccccctgca gccgccggca gctgctgagc    1260
ctgctcagcg caggacgggc gcgctgcgtg tgggacccgc cgcggcctca acccgggtcc   1320
gcggggcacc cgccggatgc gcagcctggc ctctactaca gcgccaacga gcagtgccgc   1380
gtggccttcg gccccaaggc tgtcgcctgc accttcgcca gggagcacct ggatatgtgc   1440
caggccctct cctgccacac agaccgctg gaccaaagca gctgcagccg cctcctcgtt   1500
cctctcctgg atgggacaga atgtggcgtg gagaagtggt gctccaaggg tcgctgccgc    1560
tccctggtgg agctgacccc catagcagca gtgcatgggc gctggtctag ctggggtccc    1620
cgaagtcctt gctcccgctc ctgcggagga ggtgtggtca ccaggaggcg gcagtgcaac    1680
aaccccagac ctgcctttgg ggggcgtgca tgtgttggtg ctgacctcca ggccgagatg    1740
tgcaacactc aggcctgcga gaagaccag ctggagttca tgtcgcaaca gtgcgccagg    1800
accgacggcc agccgctgcg ctcctcccct ggcggcgcct ccttctacca ctggggtgct    1860
```

```
gctgtaccac acagccaagg ggatgctctg tgcagacaca tgtgccgggc cattggcgag    1920
agcttcatca tgaagcgtgg agacagcttc ctcgatggga cccggtgtat gccaagtggc    1980 ccccggagg  acgggaccct gagcctgtgt gtgtcgggca gctgcaggac atttggctgt    2040
gatggtagga tggactccca gcaggtatgg acaggtgcc  aggtgtgtgg tggggacaac    2100
agcacgtgca gcccacggaa gggctctttc acagctggca gagcgagaga atatgtcacg    2160
tttctgacag ttaccccaa  cctgaccagt gtctacattg ccaaccacag gcctctcttc    2220
acacacttgg cggtgaggat cggagggcgc tatgtcgtgg ctgggaagat gagcatctcc    2280
cctaacacca cctacccctc cctcctggag gatggtcgtg tcgagtacag agtggccctc    2340
accgaggacc ggctgccccg cctggaggag atccgcatct ggggacccct ccaggaagat    2400
gctgacatcc aggtttacag gcggtatggc gaggagtatg gcaacctcac ccgcccagac    2460
atcaccttca cctacttcca gcctaagcca cggcaggcct gggtgtgggc cgctgtgcgt    2520
gggccctgct cggtgagctg tggggcaggg ctgcgctggg taaactacag ctgcctggac    2580
caggccagga aggagttggt ggagactgtc cagtgccaag ggagccagca ccaccagcg    2640 tggccagagg cctgcgtgct cgaaccctgc cctccctact gggcggtggg agacttcggc    2700
ccatgcagcg cctcctgtgg gggtggcctg cgggagcggc cagtgcgctg cgtggaggcc    2760
cagggcagcc tcctgaagac attgcccccca gcccggtgca gagcaggggc ccagcagcca    2820
gctgtggcgc tggaaacctg caaccccag  ccctgccctg ccaggtggga ggtgtcagag    2880
cccagctcat gcacatcagc tggtggagca ggcctggcct tggagaacga gacctgtgtg    2940
ccaggggcag atggcctgga ggctccagtg actgaggggc ctggctccgt agatgagaag    3000
ctgcctgccc ctgagccctg tgtcgggatg tcatgtcctc caggctgggg ccatctggat    3060
gccacctctg caggggagaa ggctccctcc ccatggggca gcatcaggac gggggctcaa    3120
gctgcacacg tgtggacccc tgcggcaggg tcgtgctccg tctcctgcgg gcgaggtctg    3180
atggagctgc gtttcctgtg catggactct gccctcaggg tgcctgtcca ggaagagctg    3240
tgtggcctgg caagcaagcc tgggagccgg cgggaggtct gccaggctgt cccgtgccct    3300
gctcggtggc agtacaagct ggcggcctgc agcgtgagct gtgggagagg ggtcgtgcgg    3360
aggatcctgt attgtgcccg ggcccatggg gaggacgatg gtgaggagat cctgttggac    3420
acccagtgcc aggggctgcc tcgcccggaa ccccaggagg cctgcagcct ggagccctgc    3480
ccacctaggt ggaaagtcat gtcccttggc ccatgttcgg ccagctgtgg ccttggcact    3540
gctagacgct cggtggcctg tgtgcagctc gaccaaggcc aggacgtgga ggtggacgag    3600
gcggcctgtg cggcgctggt gcggcccgag gccagtgtcc cctgtctcat tgccgactgc    3660
acctaccgct ggcatgttgg cacctggatg gagtgctctg tttcctgtgg ggatggcatc    3720
cagcgccggc gtgacacctg cctcggaccc caggcccagg cgcctgtgcc agctgatttc    3780
tgccagcact tgcccaagcc ggtgactgtg cgtggctgct gggctgggcc ctgtgtggga    3840
cagggtacgc ccagcctggt gccccacgaa gaagccgctg ctccaggacg gaccacagcc    3900
acccctgctg gtgcctccct ggagtggtcc caggcccggg gcctgctctt ctccccggct    3960
ccccagcctc ggcggctcct gcccgggccc aggaaaaact cagtgcagtc cagtgcctgt    4020
ggcaggcagc accttgagcc aacaggaacc attgacatgc gaggcccagg gcaggcagac    4080
tgtgcagtgg ccattgggcg gcccctcggg gaggtggtga ccctccgcgt ccttgagagt    4140
tctctcaact gcagtgcggg ggacatgttg ctgctttggg gccggctcac ctggaggaag    4200
atgtgcagga agctgttgga catgactttc agctccaaga ccaacacgct ggtggtgagg    4260
```

```
cagcgctgcg ggcggccagg aggtggggtg ctgctgcggt atgggagcca gcttgctcct    4320
gaaaccttct acagagaatg tgacatgcag ctctttgggc cctggggtga atcgtgagc     4380 ccctcgctga gtccagccac gagtaatgca gggggctgcc ggctcttcat taatgtggct    4440
ccgcacgcac ggattgccat ccatgccctg ccaccaaca tgggcgctgg gaccgaggga     4500
gccaatgcca gctacatctt gatccgggac acccacagct tgaggaccac agcgttccat    4560
gggcagcagg tgctctactg ggagtcagag agcagccagg ctgagatgga gttcagcgag    4620
ggcttcctga aggctcaggc cagcctgcgg ggccagtact ggaccctcca atcatgggta    4680
ccggagatgc aggaccctca gtcctggaag ggaaaggaag gaacctgagg gtcattgaac    4740
atttgttccg tgtctggcca gccctggagg gttgacccct ggtctcagtg ctttccaatt    4800 cgaactttt ccaatcttag gtatctactt tagagtcttc tccaatgtcc aaaaggctag     4860
ggggttggag gtggggactc tggaaaagca gcccccattt cctcgggtac caataaataa    4920
aacatgcagg ctgaccggcg tttttttctt aaaaaaaaaa aaaaaa                   4966
```

<210> SEQ ID NO 2
<211> LENGTH: 1427
<212> TYPE: PRT
<213> ORGANISM: Homo sapiens

<400> SEQUENCE: 2

```
Met His Gln Arg His Pro Arg Ala Arg Cys Pro Pro Leu Cys Val Ala
1               5                   10                  15

Gly Ile Leu Ala Cys Gly Phe Leu Leu Gly Cys Trp Gly Pro Ser His
            20                  25                  30

Phe Gln Gln Ser Cys Leu Gln Ala Leu Glu Pro Gln Ala Val Ser Ser
        35                  40                  45

Tyr Leu Ser Pro Gly Ala Pro Leu Lys Gly Arg Pro Pro Ser Pro Gly
    50                  55                  60

Phe Gln Arg Gln Arg Gln Arg Gln Arg Ala Ala Gly Gly Ile Leu
65                  70                  75                  80

His Leu Glu Leu Leu Val Ala Val Gly Pro Asp Val Phe Gln Ala His
                85                  90                  95

Gln Glu Asp Thr Glu Arg Tyr Val Leu Thr Asn Leu Asn Ile Gly Ala
            100                 105                 110

Glu Leu Leu Arg Asp Pro Ser Leu Gly Ala Gln Phe Arg Val His Leu
        115                 120                 125

Val Lys Met Val Ile Leu Thr Glu Pro Glu Gly Ala Pro Asn Ile Thr
    130                 135                 140

Ala Asn Leu Thr Ser Ser Leu Leu Ser Val Cys Gly Trp Ser Gln Thr
145                 150                 155                 160

Ile Asn Pro Glu Asp Asp Thr Asp Pro Gly His Ala Asp Leu Val Leu
                165                 170                 175

Tyr Ile Thr Arg Phe Asp Leu Glu Leu Pro Asp Gly Asn Arg Gln Val
            180                 185                 190

Arg Gly Val Thr Gln Leu Gly Gly Ala Cys Ser Pro Thr Trp Ser Cys
        195                 200                 205

Leu Ile Thr Glu Asp Thr Gly Phe Asp Leu Gly Val Thr Ile Ala His
    210                 215                 220

Glu Ile Gly His Ser Phe Gly Leu Glu His Asp Gly Ala Pro Gly Ser
225                 230                 235                 240

Gly Cys Gly Pro Ser Gly His Val Met Ala Ser Asp Gly Ala Ala Pro
                245                 250                 255
```

```
Arg Ala Gly Leu Ala Trp Ser Pro Cys Ser Arg Gln Leu Ser
            260                 265                 270

Leu Leu Ser Ala Gly Arg Ala Arg Cys Val Trp Asp Pro Arg Pro
        275                 280                 285

Gln Pro Gly Ser Ala Gly His Pro Pro Asp Ala Gln Pro Gly Leu Tyr
290                 295                 300

Tyr Ser Ala Asn Glu Gln Cys Arg Val Ala Phe Gly Pro Lys Ala Val
305                 310                 315                 320

Ala Cys Thr Phe Ala Arg Glu His Leu Asp Met Cys Gln Ala Leu Ser
            325                 330                 335

Cys His Thr Asp Pro Leu Asp Gln Ser Ser Cys Ser Arg Leu Leu Val
            340                 345                 350

Pro Leu Leu Asp Gly Thr Glu Cys Gly Val Glu Lys Trp Cys Ser Lys
        355                 360                 365

Gly Arg Cys Arg Ser Leu Val Glu Leu Thr Pro Ile Ala Ala Val His
370                 375                 380

Gly Arg Trp Ser Ser Trp Gly Pro Arg Ser Pro Cys Ser Arg Ser Cys
385                 390                 395                 400

Gly Gly Gly Val Val Thr Arg Arg Gln Cys Asn Asn Pro Arg Pro
            405                 410                 415

Ala Phe Gly Gly Arg Ala Cys Val Gly Ala Asp Leu Gln Ala Glu Met
            420                 425                 430

Cys Asn Thr Gln Ala Cys Glu Lys Thr Gln Leu Glu Phe Met Ser Gln
            435                 440                 445

Gln Cys Ala Arg Thr Asp Gly Gln Pro Leu Arg Ser Ser Pro Gly Gly
        450                 455                 460

Ala Ser Phe Tyr His Trp Gly Ala Ala Val Pro His Ser Gln Gly Asp
465                 470                 475                 480

Ala Leu Cys Arg His Met Cys Arg Ala Ile Gly Glu Ser Phe Ile Met
            485                 490                 495

Lys Arg Gly Asp Ser Phe Leu Asp Gly Thr Arg Cys Met Pro Ser Gly
            500                 505                 510

Pro Arg Glu Asp Gly Thr Leu Ser Leu Cys Val Ser Gly Ser Cys Arg
        515                 520                 525

Thr Phe Gly Cys Asp Gly Arg Met Asp Ser Gln Gln Val Trp Asp Arg
530                 535                 540

Cys Gln Val Cys Gly Gly Asp Asn Ser Thr Cys Ser Pro Arg Lys Gly
545                 550                 555                 560

Ser Phe Thr Ala Gly Arg Ala Arg Glu Tyr Val Thr Phe Leu Thr Val
            565                 570                 575

Thr Pro Asn Leu Thr Ser Val Tyr Ile Ala Asn His Arg Pro Leu Phe
            580                 585                 590

Thr His Leu Ala Val Arg Ile Gly Gly Arg Tyr Val Val Ala Gly Lys
        595                 600                 605

Met Ser Ile Ser Pro Asn Thr Thr Tyr Pro Ser Leu Leu Glu Asp Gly
610                 615                 620

Arg Val Glu Tyr Arg Val Ala Leu Thr Glu Asp Arg Leu Pro Arg Leu
625                 630                 635                 640

Glu Glu Ile Arg Ile Trp Gly Pro Leu Gln Glu Asp Ala Asp Ile Gln
            645                 650                 655

Val Tyr Arg Arg Tyr Gly Glu Glu Tyr Gly Asn Leu Thr Arg Pro Asp
            660                 665                 670
```

```
Ile Thr Phe Thr Tyr Phe Gln Pro Lys Pro Arg Gln Ala Trp Val Trp
            675                 680                 685

Ala Ala Val Arg Gly Pro Cys Ser Val Ser Cys Gly Ala Gly Leu Arg
690                 695                 700

Trp Val Asn Tyr Ser Cys Leu Asp Gln Ala Arg Lys Glu Leu Val Glu
705                 710                 715                 720

Thr Val Gln Cys Gln Gly Ser Gln Pro Ala Trp Pro Glu Ala
                725                 730                 735

Cys Val Leu Glu Pro Cys Pro Tyr Trp Ala Val Gly Asp Phe Gly
                740                 745                 750

Pro Cys Ser Ala Ser Cys Gly Gly Gly Leu Arg Glu Arg Pro Val Arg
                755                 760                 765

Cys Val Glu Ala Gln Gly Ser Leu Leu Lys Thr Leu Pro Pro Ala Arg
770                 775                 780

Cys Arg Ala Gly Ala Gln Gln Pro Ala Val Ala Leu Glu Thr Cys Asn
785                 790                 795                 800

Pro Gln Pro Cys Pro Ala Arg Trp Glu Val Ser Glu Pro Ser Ser Cys
                805                 810                 815

Thr Ser Ala Gly Gly Ala Gly Leu Ala Leu Glu Asn Glu Thr Cys Val
                820                 825                 830

Pro Gly Ala Asp Gly Leu Glu Ala Pro Val Thr Glu Gly Pro Gly Ser
                835                 840                 845

Val Asp Glu Lys Leu Pro Ala Pro Glu Pro Cys Val Gly Met Ser Cys
850                 855                 860

Pro Pro Gly Trp Gly His Leu Asp Ala Thr Ser Ala Gly Glu Lys Ala
865                 870                 875                 880

Pro Ser Pro Trp Gly Ser Ile Arg Thr Gly Ala Gln Ala Ala His Val
                885                 890                 895

Trp Thr Pro Ala Ala Gly Ser Cys Ser Val Ser Cys Gly Arg Gly Leu
                900                 905                 910

Met Glu Leu Arg Phe Leu Cys Met Asp Ser Ala Leu Arg Val Pro Val
                915                 920                 925

Gln Glu Glu Leu Cys Gly Leu Ala Ser Lys Pro Gly Ser Arg Arg Glu
                930                 935                 940

Val Cys Gln Ala Val Pro Cys Pro Ala Arg Trp Gln Tyr Lys Leu Ala
945                 950                 955                 960

Ala Cys Ser Val Ser Cys Gly Arg Gly Val Val Arg Arg Ile Leu Tyr
                965                 970                 975

Cys Ala Arg Ala His Gly Glu Asp Asp Gly Glu Glu Ile Leu Leu Asp
                980                 985                 990

Thr Gln Cys Gln Gly Leu Pro Arg Pro Glu Pro Gln Glu Ala Cys Ser
                995                 1000                1005

Leu Glu Pro Cys Pro Pro Arg Trp Lys Val Met Ser Leu Gly Pro
            1010                1015                1020

Cys Ser Ala Ser Cys Gly Leu Gly Thr Ala Arg Arg Ser Val Ala
            1025                1030                1035

Cys Val Gln Leu Asp Gln Gly Gln Asp Val Glu Val Asp Glu Ala
            1040                1045                1050

Ala Cys Ala Ala Leu Val Arg Pro Glu Ala Ser Val Pro Cys Leu
            1055                1060                1065

Ile Ala Asp Cys Thr Tyr Arg Trp His Val Gly Thr Trp Met Glu
            1070                1075                1080
```

| | | | | | | | | | | |
|---|---|---|---|---|---|---|---|---|---|---|
|Cys|Ser|Val|Ser|Cys|Gly|Asp|Gly|Ile|Gln|Arg|Arg|Arg|Asp|Thr|
| |1085| | | |1090| | | |1095| |

Cys Leu Gly Pro Gln Ala Gln Ala Pro Val Pro Ala Asp Phe Cys
    1100            1105            1110

Gln His Leu Pro Lys Pro Val Thr Val Arg Gly Cys Trp Ala Gly
    1115            1120            1125

Pro Cys Val Gly Gln Gly Thr Pro Ser Leu Val Pro His Glu Glu
    1130            1135            1140

Ala Ala Ala Pro Gly Arg Thr Thr Ala Thr Pro Ala Gly Ala Ser
    1145            1150            1155

Leu Glu Trp Ser Gln Ala Arg Gly Leu Leu Phe Ser Pro Ala Pro
    1160            1165            1170

Gln Pro Arg Arg Leu Leu Pro Gly Pro Gln Glu Asn Ser Val Gln
    1175            1180            1185

Ser Ser Ala Cys Gly Arg Gln His Leu Glu Pro Thr Gly Thr Ile
    1190            1195            1200

Asp Met Arg Gly Pro Gly Gln Ala Asp Cys Ala Val Ala Ile Gly
    1205            1210            1215

Arg Pro Leu Gly Glu Val Val Thr Leu Arg Val Leu Glu Ser Ser
    1220            1225            1230

Leu Asn Cys Ser Ala Gly Asp Met Leu Leu Leu Trp Gly Arg Leu
    1235            1240            1245

Thr Trp Arg Lys Met Cys Arg Lys Leu Leu Asp Met Thr Phe Ser
    1250            1255            1260

Ser Lys Thr Asn Thr Leu Val Val Arg Gln Arg Cys Gly Arg Pro
    1265            1270            1275

Gly Gly Gly Val Leu Leu Arg Tyr Gly Ser Gln Leu Ala Pro Glu
    1280            1285            1290

Thr Phe Tyr Arg Glu Cys Asp Met Gln Leu Phe Gly Pro Trp Gly
    1295            1300            1305

Glu Ile Val Ser Pro Ser Leu Ser Pro Ala Thr Ser Asn Ala Gly
    1310            1315            1320

Gly Cys Arg Leu Phe Ile Asn Val Ala Pro His Ala Arg Ile Ala
    1325            1330            1335

Ile His Ala Leu Ala Thr Asn Met Gly Ala Gly Thr Glu Gly Ala
    1340            1345            1350

Asn Ala Ser Tyr Ile Leu Ile Arg Asp Thr His Ser Leu Arg Thr
    1355            1360            1365

Thr Ala Phe His Gly Gln Val Leu Tyr Trp Glu Ser Glu Ser
    1370            1375            1380

Ser Gln Ala Glu Met Glu Phe Ser Glu Gly Phe Leu Lys Ala Gln
    1385            1390            1395

Ala Ser Leu Arg Gly Gln Tyr Trp Thr Leu Gln Ser Trp Val Pro
    1400            1405            1410

Glu Met Gln Asp Pro Gln Ser Trp Lys Gly Lys Glu Gly Thr
    1415            1420            1425

<210> SEQ ID NO 3
<211> LENGTH: 6499
<212> TYPE: DNA
<213> ORGANISM: Homo sapiens

```
<400> SEQUENCE: 3
atcgaggtcc gcgggaggct cggagcgcgc caggcggaca ctcctctcgg ctcctcccg      60 gcagcggcgg cggctcggag cgggctccgg ggctcgggtg cagcggccag cgggcgcctg    120
gcggcgagga ttacccgggg aagtggttgt ctcctggctg gagccgcgag acgggcgctc    180
agggcgcggg gccggcggcg gcgaacgaga ggacggactc tggcggccgg gtcgttggcc    240
gcggggagcg cgggcaccgg gcgagcaggc cgcgtcgcgc tcaccatggt cagctactgg    300
gacaccgggg tcctgctgtg cgcgctgctc agctgtctgc ttctcacagg atctagttca    360
ggttcaaaat taaagatcc tgaactgagt ttaaaaggca cccagcacat catgcaagca     420
ggccagacac tgcatctcca atgcaggggg gaagcagccc ataaatggtc tttgcctgaa    480
atggtgagta aggaaagcga aaggctgagc ataactaaat ctgcctgtgg aagaaatggc    540
aaacaattct gcagtacttt aaccttgaac acagctcaag caaaccacac tggcttctac    600
agctgcaaat atctagctgt acctacttca aagaagaagg aaacagaatc tgcaatctat    660
atatttatta gtgatacagg tagacctttc gtagagatgt acagtgaaat ccccgaaatt    720
atacacatga ctgaaggaag ggagctcgtc attccctgcc gggttacgtc acctaacatc    780
actgttactt taaaaaagtt tccacttgac actttgatcc ctgatggaaa acgcataatc    840
tgggacagta gaaagggctt catcatatca aatgcaacgt acaaagaaat agggcttctg    900
acctgtgaag caacagtcaa tgggcatttg tataagacaa actatctcac acatcgacaa    960
accaatacaa tcatagatgt ccaaataagc acaccacgcc cagtcaaatt acttagaggc   1020
catactcttg tcctcaattg tactgctacc actcccttga acacgagagt tcaaatgacc   1080
tggagttacc ctgatgaaaa aaataagaga gcttccgtaa ggcgacgaat tgaccaaagc   1140
aattcccatg ccaacatatt ctacagtgtt cttactattg acaaaatgca gaacaaagac   1200
aaaggacttt atacttgtcg tgtaaggagt ggaccatcat tcaaatctgt taacacctca   1260
gtgcatatat atgataaagc attcatcact gtgaaacatc gaaaacagca ggtgcttgaa   1320
accgtagctg gcaagcggtc ttaccggctc tctatgaaag tgaaggcatt tcctcgccg    1380 gaagttgtat ggtaaaaga tgggttacct gcgactgaga atctgctcg ctatttgact    1440 cgtggctact cgttaattat caaggacgta actgaagagg atgcagggaa ttatacaatc   1500
ttgctgagca taaacagtc aaatgtgttt aaaaacctca ctgccactct aattgtcaat    1560
gtgaaacccc agatttacga aaaggccgtg tcatcgtttc cagacccggc tctctaccca   1620
ctgggcagca gacaaatcct gacttgtacc gcatatggta tccctcaacc tacaatcaag   1680
tggttctggc accctgtaa ccataatcat tccgaagcaa ggtgtgactt tgttccaat    1740 aatgaagagt cctttatcct ggatgctgac agcaacatgg aaacagaat tgagagcatc    1800 actcagcgca tggcaataat agaaggaaag aataagatgg ctagcacctt ggttgtggct   1860
gactctagaa tttctggaat ctacatttgc atagcttcca ataaagttgg gactgtggga   1920
agaaacataa gcttttatat cacagatgtg ccaaatgggt tcatgttaa cttggaaaaa    1980 atgccgacgg aaggagagga cctgaaactg tcttgcacag ttaacaagtt cttatacaga   2040
gacgttactt ggattttact gcggacagtt aataacagaa caatgcacta cagtattagc   2100
aagcaaaaaa tggccatcac taaggagcac tccatcactc ttaatcttac catcatgaat   2160 gtttcccctgc aagattcagg caactatgcc tgcagagcca ggaatgtata cacaggggaa   2220
gaaatcctcc agaagaaga aattacaatc agaggtgagc actgcaacaa aaaggctgtt   2280
ttctctcgga tctccaaatt taaaagcaca aggaatgatt gtaccacaca agtaatgta    2340
```

```
aaacattaaa ggactcatta aaaagtaaca gttgtctcat atcatcttga tttattgtca    2400
ctgttgctaa ctttcaggct cggaggagat gctcctccca aaatgagttc ggagatgata    2460
gcagtaataa tgagaccccc gggccccagc tctgggcccc ccattcaggc cgagggggct    2520
gctccggggg gccgacttgg tgcacgtttg gatttggagg atccctgcac tgccttctct    2580
gtgtttgttg ctcttgctgt tttctcctgc ctgataaaca caacttggg atgatccttt     2640 ccttccattt tgatgccaac ctcttttat ttttaagtgt tgaagctgca caaactgaat     2700
aatttaaaca aatgctggtt tctgccaaag atggacacga ataagttaat tttccagctc    2760
agaatgagta cagttgaatt tgagactctg tcggacttct gcctggtttt atttgggact    2820
atttcatctg ctcttgattt gtaaatagca cctggatagc aagttataat gcttatttat    2880
ttgaaaatgc tttttttttt tttacgttaa gcacatttat cttgaactgg agcttctaaa    2940
atgggcccca ggggtgcaag atgttggtgt aattcagaga tagtaaaggt ttatcgcagt    3000
gtgaattata agagtccatc caaatcaacg tcccctccct cctctcatgc gatccaggta    3060
attatgcagt tagtgccaca gtagactagc ctagcaaagg gtttgctcct tgctgtctct    3120
gactgcacca cacagctatt gatggcagct gaaagaaagt ggatcatgcc ttaatttaa     3180 atattcctgt cctctggtta ttatttaag gaacttcatc atgttaaaat gacagcattc     3240
aaaggtgtac cacaatcaat ttatcaagga aataaaggct attgtaacca gagatttaat    3300
gcattcttct aaatgtaaat ttaaaatttg cccctttaaaa aagtccactt tccccatatg    3360
caaatgttaa taggattttt atggggatta agaagcggca aaactacaga agcagaattc    3420
aaagtaattt aaaaaataca caccagttttt aaatcaagag aagttgtaat ctcttgtttt    3480
aagcttgcgt ttgagggaaa atgacttttt caccaattta atatgcattg ttctgttgtt    3540
tttatttatg attgatcatt atatgtgact tgcataaact atttaaaaaa aaaaactata    3600
atgaccaaaa tagccatggc tgagaaacac agtggctggg cagttcaata ggaggtgaca    3660
atatgacaac ttctcaagct tgggaactca ccagactgtt tcctcccttta ggtaacagat    3720 tctgtcccac ggctaaactt gtctttcacg tgggaattgc ttttgtcaaa cgtgaaagag    3780
taaacaatag catttcccca gaatgccagt tttatggagc cccaaatgct ctgaaaacaa    3840 ttagtaaccct ggaagttgtc agcccaaagg aaagaaaaat caattgtatc ttgaaatttt    3900
acctatggct ctttggcctg gcttctttgt tcattataag ttagtgtgtt ccttcaggaa    3960
acaatgcctt aataccatag aacatggggg ccttaatagt tgctaacatt aaaaaagcaa    4020
acagaatgat tgagggatcc ttatgaaaac aaaatggtga attggacatg cagaacctac    4080
catttccttc ccctgtttgc aattttttgtg gggaggggag gatgttagta tttacaaaag    4140
atgattttaa gaacttccaa gagatgagtt taagaattcc atagagtatt agttgttcac    4200
tgtgtaatta atccttccgg agagtctttt ttttttttt taaagaaact tttgggtggg     4260
ttttgttttt tattagttac cctagggta tgttaccctg gggtatgaag ggaggtgaag     4320
ataacggagg ggggagaaaa aaaaaaggag aaaaaaggag cctaaaatgg ggaataattg    4380
aaatggaaca gggggtgtga ggctggttcc tcagtcccca ttccaaacgg aggatagaag    4440
ctgtgtattt atgtgacctg gcagatctct ggggccataa cactgaaaag tgaaagaacc    4500
tggtgggcag ctatctttgg ctactgataa ccagcagaaa tgtctgttaa ttctgatttt    4560
ctcaatttga agggatcagc tacactgtta aattttggaa agccactacc tacttccatc    4620
aagtaactta ggtttcgaaa tatgggttca acgcacctcc cttattcaaa atgtcaaaat    4680
agattattat aatgtataaa gtaagaattg acaaaatatg attcttgggt tgattggtca    4740
```

```
tttagaaact agccaaaagt gagactttta atgtagaaca ttttcagaa atgggtacaa    4800 agaaaaatgc atattactgt atatttcaga gtgtttatgt gaaccttgta tttaattgag    4860
agtcccatgt acgttctgca gcctttttgc tgcttctatc atctgaagtt tgtgtagtac    4920
aaataaggcc tttgggattc ttaatgacat ttatgttaaa atgttctctt ctctttaaac    4980
accgttttcc aatccacctg tcagggagtc caaatcgtgt ctgtgttgat gatgctatac    5040
tttgtagcta gaaaaacaat tttagtgttg tgggctctgt attcagactt ccttttaca     5100 agaccgatgg gcagtgatag attattttat catatttaat gcatgggaaa tagtgtgctg    5160
aggaagctat taaaagtata actcagtgaa ttgggtctga gttttaaatg agatatttca    5220
aaattggctt gccactgtaa aagcgactaa ataataatat gatactgttc tttatgatct    5280
tgtcatgttt cactgatatg tttggggtct tcactatgta aaaaatgtca aaattgtaat    5340
gagcaagcat gtacaagtag tcgtaaatca aaggttttaa acaggactgc attttcaatt    5400
aggaaaagct gtttggcaga tagcatccaa tgcaaaaaca gaaatatcgt aacgttctgc    5460
ttagtgggca agataagata ggaaagacat gctcaaagag gcaaagaat cattgctatc      5520 attcattcta cactagttg aagaagtttt tgtacatcag agcacttcct tcagcacact      5580
tttttgcctt cagatttcat tttttataaa atgagaagac taatgataaa ctgtagaaat    5640
caaaatttat tgagaaatct gtttctccta acagatagta accctgccat gatatactac    5700
ttcaacaatg ttataaaatt tatgtgataa tatacatttt aacctgggat ttctaaattg    5760
ctttaacaaa tgctaatcct gagagttgcc ctgcaggact caaaagggaa aggttttggg    5820
acgtggcaga accctgcagg gacatggaat taaggccatt gcaatgtatc atctttgtag    5880
cattgtcatc actcctaagc tgccttcaca gttttagtac actaagatga ggaaatcgaa    5940
aatgggcaga gaaagctcat actgtataat tgaagacagt gacagagaac gtgtcagtta    6000 tgccaaaaact cttttgattt ctgttccagg atttccaaca agagggggaaa ggaatgactt   6060 gggagggtgg gaaagacatt aggagttgtt tttatttttt accttggaag ctttagctac    6120
caatccagta ccctcctaac tagaatgtat acacatcagc aggactgact gactacttca    6180
ttagagatat actgtactca ttgggggcct tgggggtact gctgttctta tgtgggattt    6240
taatgttgta atgtattgca tcttaatgta ttgaattcat tttgttgtac tatattggtt    6300
ggcattttat taaataaat tgtattgtat catatttgta tgttttaaga gaaaataata     6360
taaaatacaa tatttgtact attatatagt gcaaaaacta caaatctgtg cctctgcctc    6420
ttgaattaat tctttggttg cttgcatttg ggaagggaat ggagaaagga aagaaccaat    6480
aaagctttca aagttcaag                                                 6499
```

<210> SEQ ID NO 4
<211> LENGTH: 687
<212> TYPE: PRT
<213> ORGANISM: Homo sapiens

<400> SEQUENCE: 4

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60
```

```
Glu Met Val Ser Lys Glu Ser Glu Arg Leu Ser Ile Thr Lys Ser Ala
 65                  70                  75                  80

Cys Gly Arg Asn Gly Lys Gln Phe Cys Ser Thr Leu Thr Leu Asn Thr
                 85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
            275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
            355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
            435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480
```

-continued

```
Asp Phe Cys Ser Asn Asn Glu Glu Ser Phe Ile Leu Asp Ala Asp Ser
            485                 490                 495
Asn Met Gly Asn Arg Ile Glu Ser Ile Thr Gln Arg Met Ala Ile Ile
            500                 505                 510
Glu Gly Lys Asn Lys Met Ala Ser Thr Leu Val Val Ala Asp Ser Arg
            515                 520                 525
Ile Ser Gly Ile Tyr Ile Cys Ile Ala Ser Asn Lys Val Gly Thr Val
            530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
            565                 570                 575
Cys Thr Val Asn Lys Phe Leu Tyr Arg Asp Val Thr Trp Ile Leu Leu
            580                 585                 590
Arg Thr Val Asn Asn Arg Thr Met His Tyr Ser Ile Ser Lys Gln Lys
            595                 600                 605
Met Ala Ile Thr Lys Glu His Ser Ile Thr Leu Asn Leu Thr Ile Met
            610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
            645                 650                 655
Gly Glu His Cys Asn Lys Lys Ala Val Phe Ser Arg Ile Ser Lys Phe
            660                 665                 670
Lys Ser Thr Arg Asn Asp Cys Thr Thr Gln Ser Asn Val Lys His
            675                 680                 685
```

METHODS RELATING TO THE DIAGNOSIS AND TREATMENT OF PREECLAMPSIA COMPRISING ADMINISTRATION OF ADAMTS13 POLYPEPTIDES

CROSS-REFERENCE TO RELATED APPLICATIONS

This application is a 35 U.S.C. § 371 National Phase Entry Application of International Application No. PCT/US16/032305 filed May 13, 2016, which designates the U.S. and claims benefit under 35 U.S.C. § 119(e) of U.S. Provisional Application No. 62/162,151 filed May 15, 2015, the contents of which are incorporated herein by reference in their entiretyies.

GOVERNMENT SUPPORT

This invention was made with government support under Grant Nos. R01HL102101 awarded by the National Heart, Lung, and Blood Institute of the National Institutes of Health. The U.S. government has certain rights in the invention.

SEQUENCE LISTING

The instant application contains a Sequence Listing which has been submitted electronically in ASCII format and is hereby incorporated by reference in its entirety. Said ASCII copy, created on May 10, 2016, is named 701039-084711-PCT_SL.txt and is 33,708 bytes in size

TECHNICAL FIELD

The technology described herein relates to the diagnosis, prognosis, and treatment of thrombotic microangiopathy.

BACKGROUND

Thrombotic microangiopathies (TMAs) are a heterogeneous group of life-threatening disorders characterized by thrombocytopenia, schistocytosis, hemolytic anemia, microvascular thrombosis and end-organ damage affecting the kidney and brain. Among the major subtypes of TMAs are thombocytopenic purpura (TTP) and hemolytic uremic syndrome (HUS). TMAs may also be pregnancy-related: either as a facet of preeclampsia, characterized by hypertension and proteinuria, or as part of the HELLP syndrome (Hemolysis, Elevated Liver enzymes and Low Platelet count). HELLP syndrome is a severe complication of preeclampsia, occurring in 0.5% to 0.9% of all pregnancies. Acquired TMAs are also observed after solid organ transplants and/or are related to certain drugs, advanced malignancies, severe hypertension or infections. Administration of VEGF inhibitors can lead to TMA but risk factors for VEGF inhibitor-related TMA remain unknown.

SUMMARY

As demonstrated herein, the inventors have found that a deficiency of the enzyme ADAMTS13 can contribute to the development of TMA. Accordingly, provided herein are methods of diagnosis, prognosis, and treatment relating to the role of ADAMTS13 in the pathology of TMA and preeclampsia.

In one aspect, described herein is a method of treating or preventing thrombotic microangiopathy in a subject being treated with a VEGF inhibitor, the method comprising administering to the subject an agonist of ADAMTS13. In one aspect, described herein is a method of treating or preventing thrombotic microangiopathy (TMA) in a subject in need of treatment therefor, the method comprising administering to the subject an agonist of ADAMTS13. In one aspect, described herein is a method of treating or preventing preeclampsia or a complication thereof in a subject in need of treatment therefor, the method comprising administering to the subject an agonist of ADAMTS13; wherein the complication is selected from the group consisting of: TMA; eclampsia; and Hemolysis, Elevated Liver enzymes and Low Platelet count syndrome (HELLP). In some embodiments, the subject has an elevated level of circulating soluble VEGF receptor 1 (soluble fms-like tyrosine kinase 1; sFlt-1). In one aspect, described herein is a method of treating or preventing thrombotic microangiopathy in a subject in need of treatment for preeclampsia, the method comprising administering to the subject an agonist of ADAMTS13. In some embodiments, the subject has a condition selected from the group consisting of preeclampsia; VEGF-inhibitor associated TMA; TMA; thrombotic thrombocytic purpura (TPP); hemolytic uremic syndrome (HUS); HELLP syndrome; drug induced thrombotic microangiopathy; TMA induced by cyclosprorine or tacrolimus; solid organ transplant; infection; hypertension; and cancer. In one aspect, described herein is a method of treating cancer, the method comprising administering to a subject in need of treatment for cancer: a VEGF inhibitor; and an agonist of ADAMTS13. In some embodiments, the subject is a subject at risk or at increased risk of developing thrombotic microangiopathy. In one aspect, described herein is a method of treating or preventing thrombotic microangiopathy in a subject in need of treatment for cancer, the method comprising administering to the subject: a VEGF inhibitor; and an agonist of ADAMTS13.

In some embodiments, the VEGF inhibitor is selected from the group consisting of: bevacizumab; sunitinib; aflibercept; pazopanib; axitinib; sorafenib; vandetanib; regorafenib; and ramucirumab. In some embodiments, the agonist of ADAMTS13 is selected from the group consisting of an ADAMTS13 polypeptide or functional fragment thereof; a recombinant ADAMTS13 polypeptide or functional fragment thereof; a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors. In some embodiments, the thrombotic microangiopathy is selected from the group consisting of: thrombotic thrombocytic purpura (TPP); hemolytic uremic syndrome (HUS); and Hemolysis, Elevated Liver enzymes and Low Platelet count syndrome (HELLP). In some embodiments, the thrombotic microangiopathy is thrombotic thrombocytic purpura (TPP). In some embodiments, the thrombotic microangiopathy is Hemolysis, Elevated Liver enzymes and Low Platelet count syndrome (HELLP). In some embodiments, the subject is a subject determined to have an elevated level of expression of soluble VEGF receptor 1 (soluble fms-like tyrosine kinase 1; sFlt-1). In some embodiments, the subject is a subject determined to have a reduced level of expression and/or activity of ADAMTS13.

In one aspect, described herein is a method of reducing blood pressure or treating or preventing renal damage in a subject in need thereof, the method comprising administering to the subject an agonist of ADAMTS13. In some embodiments, the subject is a subject who is receiving or has received administration of a VEGF inhibitor. In some embodiments, the VEGF inhibitor is selected from the group consisting of: bevacizumab; sunitinib; aflibercept; pazopanib; axitinib; sorafenib vandetanib; regorafenib; and ramucirumab. In some embodiments, the subject has a condition selected from the group consisting of: Preeclampsia; VEGF-inhibitor associated TMA; TMA; thrombotic thrombocytic purpura (TPP); hemolytic uremic syndrome (HUS); Hemolysis, Elevated Liver enzymes and Low Platelet count syndrome (HELLP); drug induced thrombotic microangiopathy (e.g., TMA induced by cyclosprorine or tacrolimus); solid organ transplant; infection; hypertension; and cancer. In some embodiments, the agonist of ADAMTS13 is selected from the group consisting of: an ADAMTS13 polypeptide or functional fragment thereof; a recombinant ADAMTS13 polypeptide or functional fragment thereof; a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors. In some embodiments, the subject is a subject determined to have an elevated level of expression of soluble VEGF receptor 1 (soluble fms-like tyrosine kinase 1; sFlt-1). In some embodiments, the subject is a subject determined to have a reduced level of expression and/or activity of ADAMTS13.

In one aspect, described herein is an assay comprising: measuring the level of expression or activity of ADAMTS13 in a test sample obtained from a subject; wherein a decrease in the level relative to a reference level indicates the subject has a higher risk of having or developing thrombotic microangiopathy (TMA). In one aspect, described herein is a method of identifying a subject in need of treatment for thrombotic microangiopathy (TMA), the method comprising: measuring the level or activity of ADAMTS13 in a test sample obtained from a subject; and identifying the subject as being in need of treatment for thrombotic microangiopathy (TMA) when the level of ADAMTS13 is decreased relative to a reference level. In one aspect, described herein is a method of determining if a subject is at risk for thrombotic microangiopathy (TMA), the method comprising: measuring the level or activity of ADAMTS13 in a test sample obtained from a subject; comparing the level of level or activity of ADAMTS13 in the sample to a reference level; determining that the subject is at risk for thrombotic microangiopathy (TMA) when the level is decreased relative to a reference level; and determining that the subject is not at risk for thrombotic microangiopathy (TMA) when the level is not decreased relative to a reference level. In one aspect, described herein is a method of determining the efficacy of a treatment for thrombotic microangiopathy (TMA), the method comprising: a) measuring the level or activity of ADAMTS13 in a test sample obtained from a subject before administration of the treatment; b) measuring the level or activity of ADAMTS13 in a test sample obtained from a subject after administration of the treatment; c) determining that the treatment is efficacious when the level determined in step (b) is not decreased relative to the level determined in step (a); and d) determining that the treatment is not efficacious when the level determined in step (b) is decreased relative to the level determined in step (a). In one aspect, described herein is a method of treatment for thrombotic microangiopathy (TMA) comprising; measuring the level or activity of ADAMTS13 in a test sample obtained from a subject; and treating the subject for TMA when the level is decreased relative to a reference level. In one aspect, described herein is a method of treatment for thrombotic microangiopathy (TMA) comprising; administering a treatment for TMA to a subject determined to have a level or activity of ADAMTS13 which is decreased relative to a reference level. In some embodiments, the agonist of ADAMTS13 is selected from the group consisting of: an ADAMTS13 polypeptide or functional fragment thereof; a recombinant ADAMTS13 polypeptide or functional fragment thereof; a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors. In some embodiments, the subject is a subject determined to have an elevated level of expression of soluble VEGF receptor 1 (soluble fms-like tyrosine kinase 1; sFlt-1). In some embodiments, the subject is a subject determined to have a reduced level of expression and/or activity of ADAMTS13. In some embodiments, the thrombotic microangiopathy is selected from the group consisting of: thrombotic thrombocytic purpura (TPP); hemolytic uremic syndrome (HUS); and Hemolysis, Elevated Liver enzymes and Low Platelet count syndrome (HELLP). In some embodiments, the subject is a subject who is receiving or has received administration of a VEGF inhibitor. In some embodiments, the VEGF inhibitor is selected from the group consisting of: bevacizumab; sunitinib; aflibercept; pazopanib; axitinib; sorafenib; vandetanib; regorafenib; and ramucirumab. In some embodiments, the subject has a condition selected from the group consisting of preeclampsia; VEGF-inhibitor associated TMA; TMA; thrombotic thrombocytic purpura (TPP); hemolytic uremic syndrome (HUS); Hemolysis, Elevated Liver enzymes and Low Platelet count syndrome (HELLP); drug induced thrombotic microangiopathy (e.g., TMA induced by cyclosprorine or tacrolimus); solid organ transplant; infection; hypertension; and cancer. In some embodiments, the subject is a subject determined to have an elevated level of expression of soluble VEGF receptor 1 (soluble fms-like tyrosine kinase 1; sFlt-1.

In some embodiments, the level of ADAMTS13 is determined by measuring the level of a nucleic acid. In some embodiments, the level of ADAMTS13 is determined by measuring the level of ADAMTS13 RNA transcript. In some embodiments, the level of the nucleic acid is determined using a method selected from the group consisting of: RT-PCR; quantitative RT-PCR; Northern blot; microarray based expression analysis; next-generation sequencing; and RNA in situ hybridization. In some embodiments, the level of ADAMTS13 is determined by measuring the level of ADAMTS13 polypeptide. In some embodiments, the polypeptide level is measured using immunochemistry. In some embodiments, the antibody reagent is detectably labeled or generates a detectable signal. In some embodiments, the level of the polypeptide is determined using a method selected from the group consisting of: Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay. In some embodiments, the expression level of ADAMTS13 is normalized relative to the expression level of one or more reference genes or reference proteins. In some embodiments, the reference level of ADAMTS13 is the expression level of ADAMTS13 in a prior sample obtained from the subject. In some embodiments, the sample comprises blood; serum; urine; or plasma.

In some embodiments, the assay or method further comprises the step of administering to the subject a treatment selected from the group consisting of: an agonist of ADAMTS13; an ADAMTS13 polypeptide or functional fragment thereof; a recombinant ADAMTS13 polypeptide or functional fragment thereof; a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors.

In one aspect, described herein is a method of treating or preventing thrombotic microangiopathy in a subject being treated with a VEGF inhibitor, the method comprising administering to the subject an agonist of ADAMTS13. In one aspect, described herein is a method of treating or preventing thrombotic microangiopathy (TMA) in a subject in need of treatment therefor, the method comprising administering to the subject an agonist of ADAMTS13. In one aspect, described herein is a method of treating or preventing preeclampsia or a complication thereof in a subject in need of treatment therefor, the method comprising administering to the subject an agonist of ADAMTS13; wherein the complication is selected from the group consisting of: TMA; eclampsia; and Hemolysis, Elevated Liver enzymes and Low Platelet count syndrome (HELLP). In some embodiments, the subject has an elevated level of circulating soluble VEGF receptor 1 (soluble fms-like tyrosine kinase 1; sFlt-1). In one aspect, described herein is a method of treating or preventing thrombotic microangiopathy in a subject in need of treatment for preeclampsia, the method comprising administering to the subject an agonist of ADAMTS13. In some embodiments, the subject has a condition selected from the group consisting of: preeclampsia; VEGF-inhibitor associated TMA; TMA; thrombotic thrombocytic purpura (TPP); hemolytic uremic syndrome (HUS); HELLP syndrome; drug induced thrombotic microangiopathy; TMA induced by cyclosprorine or tacrolimus; solid organ transplant; infection; hypertension; and cancer. In one aspect, described herein is a method of treating cancer, the method comprising administering to a subject in need of treatment for cancer: a VEGF inhibitor; and an agonist of ADAMTS13. In some embodiments, the subject is a subject at risk or at increased risk of developing thrombotic microangiopathy. In one aspect, described herein is a method of treating or preventing thrombotic microangiopathy in a subject in need of treatment for cancer, the method comprising administering to the subject: a VEGF inhibitor; and an agonist of ADAMTS13. In some embodiments, the VEGF inhibitor is selected from the group consisting of: bevacizumab; sunitinib; aflibercept; pazopanib; axitinib; sorafenib; vandetanib; regorafenib; and ramucirumab. In some embodiments, the agonist of ADAMTS13 is selected from the group consisting of: an ADAMTS13 polypeptide or functional fragment thereof, a recombinant ADAMTS13 polypeptide or functional fragment thereof, a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors. In some embodiments, the thrombotic microangiopathy is selected from the group consisting of: thrombotic thrombocytic purpura (TPP); hemolytic uremic syndrome (HUS); and Hemolysis, Elevated Liver enzymes and Low Platelet count syndrome (HELLP). In some embodiments, the thrombotic microangiopathy is thrombotic thrombocytic purpura (TPP). In some embodiments, the thrombotic microangiopathy is Hemolysis, Elevated Liver enzymes and Low Platelet count syndrome (HELLP). In some embodiments, the subject is a subject determined to have an elevated level of expression of soluble VEGF receptor 1 (soluble fms-like tyrosine kinase 1; sFlt-1). In some embodiments, the subject is a subject determined to have a reduced level of expression and/or activity of ADAMTS13.

BRIEF DESCRIPTION OF THE DRAWINGS

FIG. 1C demonstrates that reticulocyte counts were strongly elevated by day 10 in the ADAMTS13−/− Ad-sFlt-1 mice but also increased in the WT Ad-sFlt-1 mice. (n=7-13 for FIGS. 1A-1C). FIG. 1D demonstrates that representative blood smears appear normal in the WT Ad-sFlt-1 and ADAMTS13−/− Ad-null mice but show shistocytosis, polychromasia and anisocytosis in the ADAMTS13−/− Ad-sFlt-1 mice. Scale bars: 10 μm. FIG. 1E demonstrates that hemoglobin was decreased in the ADAMTS13−/− Ad-sFlt-1 mice at day 7, indicating hemolytic anemia (n=7-13). FIG. 1F depicts VWF plasma levels measured on day 7 after virus injection. Levels were compared to those of pooled untreated WT plasma or pooled untreated ADAMTS13−/− plasma, depending on the mouse genotype. Only WT mice injected with Ad-sFlt-1 showed an increase in plasma VWF levels (n=7-10). *P<0.05; P<0.01; *P<0.001, ****P<0.0001.

FIG. 3A demonstrates that proteinuria, determined as albumin/creatinine-ratio, showed a dramatic increase in the ADAMTS13−/− Ad-sFlt-1 mice by day 7. In WT Ad-sFlt-1 mice, albumin-creatinine ratios increased significantly on day 7 but overall stayed low (n=4-13). FIG. 3B depicts systolic blood pressure measured non-invasively by the tail-cuff method. Both WT Ad-sFlt-1 and ADAMTS13−/− Ad-sFlt-1 mice had significant increases in their systolic blood pressure. However, blood pressure reached higher values in the ADAMTS13−/− mice under Ad-sFlt-1 overexpression (n=5-20). FIG. 3C Upper panel: H&E micrographs of representative kidney glomeruli show normal size and open capillary loops (some of them filled with erythrocytes) in the WT Ad-sFlt-1 and the ADAMTS13−/− Ad-null mice but enlarged glomeruli and vascular loop occlusion in the ADAMTS13−/− Ad-sFlt-1 group. Scale bar: 20 µm. FIG. 3C Lower panel: Electron microscopy images at 5000× also show increased glomerular size and obstructed capillary loops in the ADAMTS13−/− Ad-sFlt-1 mice, due to endothelial cell swelling. Asterisks indicate to open capillary loops, which are visible either as white space or filled with light-grey erythrocytes. Scale bar: 4 µm. FIG. 3D depicts quantification of open capillary volume by ImageJ in H&E micrographs reveals a strong reduction of open capillary loops only in ADAMTS13−/− Ad-sFlt-1 mice. FIG. 3E demonstrates that glomerular area was increased in ADAMTS13−/− mice after Ad-sFlt-1-injection (n=5-6 for D,E). *$P<0.05$; $P<0.01$; *$P<0.001$, ****$P<0.0001$.

FIG. 4E demonstrates that upon rhADAMTS13 treatment, VWF plasma levels increased significantly in ADAMTS13−/− sFlt-1 mice compared to vehicle-treated mice (n=6-8). FIG. 4F depicts representative blood smears demonstrating schistocytes and an increased number of reticulocytes in the ADAMTS13−/− Ad-sFlt-1 mice treated with PBS but appear normal in the group that received treatment with rhADAMTS13. Scale bar: 10 µm. FIG. 4G depicts results of immunohistochemistry demonstrating that VWF-rich thrombi (brown, arrowheads) are mostly lacking in mice treated with rhADAMTS13 at day 7 after injection of Ad-sFlt-1. Scale bar: 100 µm. Arrowheads indicate VWF-positive thrombi. *$P<0.05$; $P<0.01$; *$P<0.001$, ****$P<0.0001$.

FIG. 5A depicts representative H&E micrographs (upper panel) and EM pictures (lower panel) at 5000× show that treatment of ADAMTS13−/− Ad-sFlt-1 mice with rhADATMS 13 from day 4 to day 7 after Ad-sFlt-1 injection improved kidney histology with smaller glomeruli and less capillary occlusion, compared to ADAMTS13−/− Ad-sFlt-1 mice that had received only PBS. Mice were sacrificed at day 7 after Ad-sFlt-1 injection. Scale bars: 20 and 4 µm, respectively. Asterisks indicate open capillary loops in the EM pictures. FIG. 5B depicts quantification of open capillary volume and FIG. 5C glomerular area corroborated the improvement in kidney structure in the rhADAMTS13-treated ADAMTS13−/− Ad-sFlt-1 mice compared to vehicle-treated mice (n=5-8 for FIGS. 5B, 5C). FIGS. 5D and 5E demonstrate that (FIG. 5D) Proteinuria (n=4-9) and (FIG. 5E) blood pressure (n=3-6) improved in ADAMTS13−/− Ad-sFlt-1 mice upon rhADAMTS13 treatment. Blood pressure was also normalized in the rhADAMTS13-treated WT mice overexpressing sFlt-1. *$P<0.05$; **$P<0.01$.

FIG. 11A depicts a graph of percent of original body weight lost in WT and ADAMTS13−/− mice. ADAMTS13−/− mice had significantly more weight loss on days 9-10 when their disease was most severe. FIG. 11B depicts a graph demonstrating that ADAMTS13−/− mice have a more severe colitis phenotype based on clinical colitis scores on days 8-10. FIG. 11C depicts a graph demonstrating that hemoglobin concentration in WT and ADAMTS13−/− mice without colitis is not significantly different at baseline. With colitis, both WT and ADAMTS13−/− mice became anemic but the ADAMTS13−/− mice became more anemic suggesting more severe disease. FIG. 11D depicts a graph demonstrating that colon length was slightly shorter in ADAMTS13−/− mice than WT at baseline. With colitis, ADAMTS13−/− mice had shorter colons than WT suggesting more edema and inflammation. FIG. 11E depicts a graph demonstrating that spleen weight did not differ at baseline between ADAMTS13−/− and WT but significantly increased in both genotypes with colitis. FIG. 11C depicts histologic scoring of H+E stained colon sections from WT and ADAMTS13−/− mice, demonstrating more severe disease in ADAMTS13−/− mice. FIG. 11G-11J depict graphs demonstrating that circulating total leukocytes and subsets were measured at baseline and on day 10 of colitis. FIG. 11G: Leukocyte counts did not differ at baseline but decreased more in ADAMTS13−/− mice with colitis. FIG. 11H Neutrophils increased in WT mice with DSS colitis but did not in ADAMTS13−/− mice with colitis. FIG. 11I: Lymphocytes did not differ between genotypes at baseline or with colitis. FIG. 11J: Monocytes increased in both genotypes with colitis. In all graphs, mean and SEM are shown. *$P<0.05$, $P<0.005$, *$P<0.0005$.

FIG. 12A depicts a graph of demonstrating that platelet counts for WT and ADAMTS13−/− mice without colitis did not differ. With colitis, there was significant thrombocytosis in WT mice while in ADAMTS13−/− mice platelet count varied more widely but had a similar mean to baseline. FIG. 12B depicts a graph of demonstrating that platelet counts trended to be lower in mice with more weight loss, an indicator of worse colitis, and tended to decrease more in ADAMTS13−/− mice with colitis (slopes P=0.12). FIG. 12C depicts a graph of increased VWF expression in wildtype mice, mostly within the vessel wall with likely some VWF positive platelets in the lumen. In contrast, in most ADAMTS13−/− mice we found a completely occlusive VWF rich thrombus in a submucosal vessel. Entire Swiss rolled sections of colon were inspected for thrombi. We found one or more VWF rich thrombi in most ADAMTS13−/− colon sections and none in WT colons with colitis. In FIGS. 12A and 12C, mean and SEM are shown. *P<0.05, P<0.005, *P<0.0005.

FIG. 13A demonstrates that WT (n=13) and ADAMTS13−/− (n=9) mice had increased plasma VWF with colitis. The plot displays the fold increase over genotype mean without and with DSS treatment. In FIG. 13B, Image J software was used to quantify VWF immunofluorescence intensity divided by DNA area (to represent colon tissue area captured on the image). Higher VWF intensity was observed in ADAMTS13−/− mice with colitis compared to ADAMTS13−/− without colitis. Furthermore, ADAMTS13−/− mice with colitis had significantly more VWF staining intensity compared to WT mice with colitis. Notably, there was no difference in WT and ADAMTS13−/− VWF signal intensity at baseline. There was a tendency for VWF intensity to increase with colitis in WT mice. Mean and SEM are shown. **P<0.005.

FIG. 14A depicts a graph of percent of original body weight in WT mice with DSS treated with vehicle (squares) or rhADAMTS13 (circles). There was significantly less weight loss in rhADAMTS13 treated mice on days 7-10 when colitis is most severe. FIG. 14B demonstrates that colitis scores are more severe on days 8 and 9 in vehicle treated compared rhADAMTS13 treated mice. FIG. 14C demonstrates that plasma hemoglobin decreases with colitis in both vehicle and rhADAMTS13 treated mice. However, there is no significant difference in hemoglobin concentration between the treatment groups. FIG. 14D demonstrates that platelet count increased in both groups with colitis but tended to be lower in the rhADAMTS13 treatment group. Five of seven mice in each group developed bloody diarrhea by day 5 and all mice in both groups by day 6. FIG. 14E demonstrates that there was no difference in the onset of bloody diarrhea in rhADAMTS13 or vehicle treated mice with DSS colitis. FIG. 14F demonstrates that plasma IL-6, a pro-inflammatory and prothrombotic cytokine was lower in rhADAMTS13 treated compared to vehicle treated DSS colitic mice. IL-6 also increased with colitis in vehicle treated mice but did not differ from baseline in rhADAMTS13 treated mice. In all graphs, mean and SEM are shown. *P<0.05, P<0.005, *P<0.0005.

DETAILED DESCRIPTION

Figure 1A:
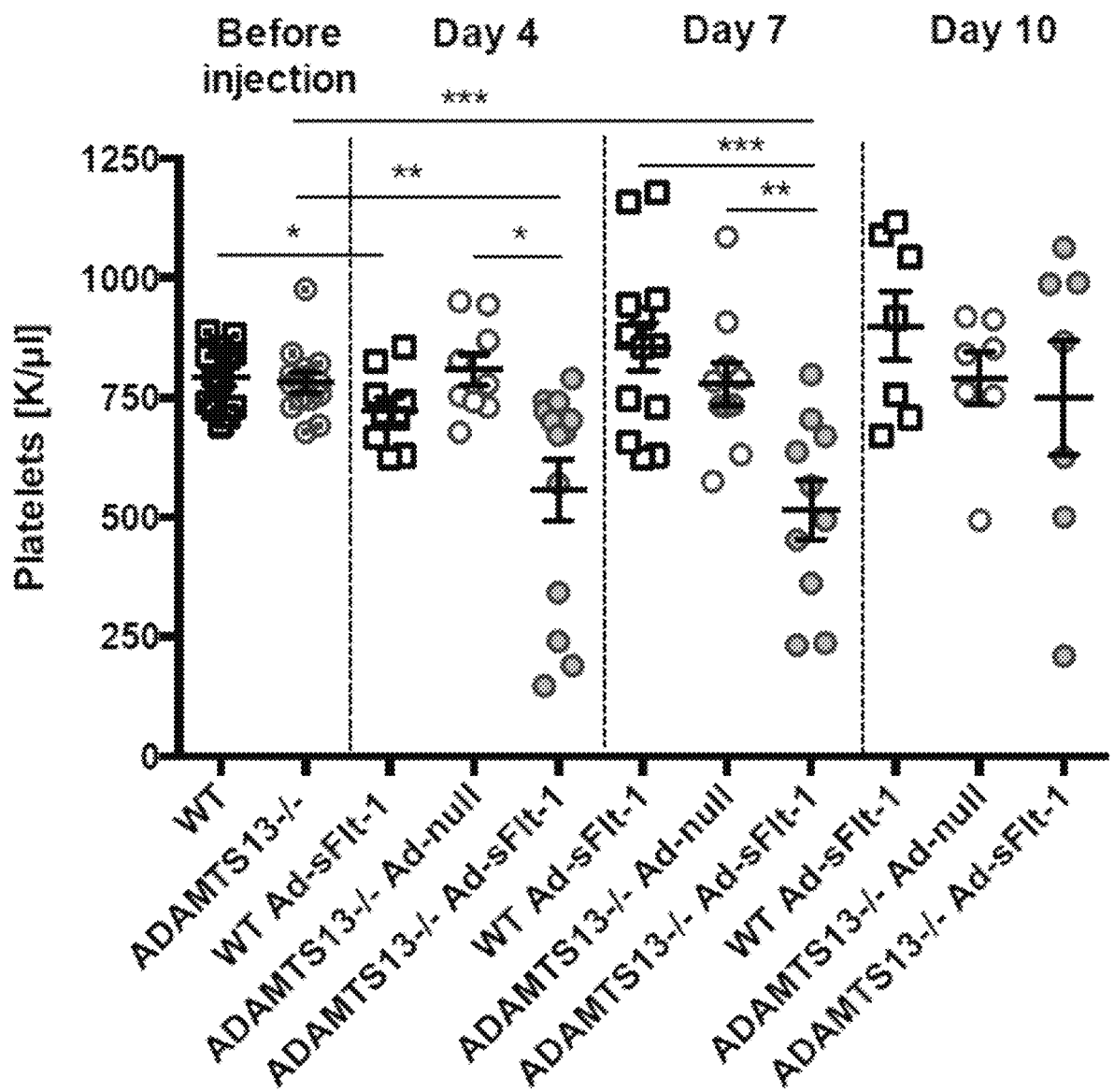
FIGS. 1A-1F demonstrate that lack of ADAMTS13 exacerbates the development of TMA under anti-VEGF-treatment with sFlt-1. Blood parameters were measured before as well as 4, 7 and 10 days after Ad-sFlt-1 or Ad-null injection in WT and ADAMTS13−/− mice. Platelet counts (FIG. 1A) and presence of schistocytes in peripheral blood smears (FIG. 1B) reveal thrombocytopenia and schistocytosis in the ADAMTS13−/− Ad-sFlt-1 mice with a maximum on day 7.

As described herein, decreased activity and/or levels of ADAMTS13 can contribute to the development of thrombotic microangiopathy (TMA). As used herein, "thrombotic microangiopathy" or "TMA" refers to a group of conditions characterized by thrombosis in capillaries and/or arterioles, e.g. as a result of endothelial injury. TMA is typically triggered by vascular injury, e.g. due to viruses, toxins, antibodies, drugs, congenital conditions, and/or deficiencies in the factors necessary for coagulation. Non-limiting examples of TMAs can include thrombotic thrombocytic purpura (TPP); hemolytic uremic syndrome (HUS); and Hemolysis, Elevated Liver enzymes and Low Platelet count syndrome (HELLP). In some embodiments, the TMA can be thrombotic thrombocytic purpura (TPP). In some embodiments, the thrombotic microangiopathy can be Hemolysis, Elevated Liver enzymes and Low Platelet count syndrome (HELLP). In some embodiments, the TMA can be a VEGF inhibitor-induced TMA, e.g. a TMA induced by the administration of a VEGF inhibitor (e.g. in a cancer patient). The various subtypes of TMA, their symptoms, diagnosis, and causes are described in the art, e.g. in Ruggenenti et al. Kidney International 2001 60:831-846; Moake NEJM 2002 347:589-600; and Kerstin et al. Curr Opin Nephrology and Hypertension 2010 19:242-247; each of which is incorporated herein by reference in its entirety.

In one aspect, described herein is a method of treating cancer, the method comprising administering to a subject in need of treatment for cancer: a VEGF inhibitor; and an agonist of ADAMTS13. In one aspect, described herein is a method of treating or preventing thrombotic microangiopathy in a subject in need of treatment for cancer, the method comprising administering to the subject: a VEGF inhibitor; and an agonist of ADAMTS13. In one aspect, described herein is a method of treating or preventing thrombotic microangiopathy in a subject in need of treatment for preeclampsia, the method comprising administering to the subject an agonist of ADAMTS13. In one aspect, described herein is a method of treating or preventing thrombotic microangiopathy (TMA) in a subject in need of treatment therefor, the method comprising administering to the subject an agonist of ADAMTS13. In one aspect, described herein is a method of reducing blood pressure or treating or preventing renal damage in a subject in need thereof, the method comprising administering to the subject an agonist of ADAMTS13. In some embodiments of the foregoing aspects, the subject can be one who is receiving or has received administration of a VEGF inhibitor. In some embodiments of the foregoing aspects, the subject is at risk of having or developing a TMA.

As used herein, "ADAMTS13" or "a disintegrin and metalloproteinase with a thrombospondin type 1 motif, member 13" refers to a zinc-containing metalloprotease that cleaves von Willebrand factor (vWf), degrading large vWf multimers in the blood and thereby inhibiting blood clotting. ADAMTS13 is also known in the art as von Willebrand factor-cleaving protease (VWFCP). The sequences of ADAMTS13 for several species are known in the art, e.g. human ADAMTS13 (NCBI Gene ID: 11093) nucleic acid (NCBI Ref Seq: NM_139025; SEQ ID NO: 1) and amino acid (NCBI Ref Seq: NP_620594; SEQ ID NO: 2) sequences.

As used herein, an agonist refers to any agent that increases the level and/or activity of the target, e.g, of ADAMTS13. As used herein, the term "agonist" refers to an agent which increases the expression and/or activity of the target by at least 10% or more, e.g. by 10% or more, 50% or more, 100% or more, 200% or more, 500% or more, or 1000% or more. The efficacy of an agonist of, for example, ADAMTS13, e.g. its ability to increase the level and/or activity of ADAMTS13 can be determined, e.g. by measuring the level of an expression product of ADAMTS13 and/or the activity of ADAMTS13. Methods for measuring the level of a given mRNA and/or polypeptide are known to one of skill in the art, e.g. RTPCR with primers can be used to determine the level of RNA, and Western blotting with an antibody (e.g. an anti-ADAMTS13 antibody, e.g. Cat No. ab90786 Abcam; Cambridge, Mass.) can be used to determine the level of a polypeptide. The activity of, e.g. ADAMTS13 can be determined using methods known in the art see, e.g., Crist and Rogers. Lab Medicine 2009 40:232-235; which is incorporated by reference herein in its entirety, for descriptions of commercial and non-commerical ADAMTS13 activity assays. Commercially available assays can include ADAMTS-13 Activity Assay (GTI, Waukesha, Wis.) and the Technozym ADAMTS-13 ELISA kit (Technoclone, Vienna, Austria).

Non-limiting examples of agonists of ADAMTS13 can include ADAMTS13 polypeptides or fragments thereof and nucleic acids encoding a ADAMTS13 polypeptide, e.g. a polypeptide comprising the sequence SEQ ID NO: 2 or a nucleic acid comprising the sequence of SEQ ID NO: 1 or variants thereof. In some embodiments, the agonist of ADAMTS13 can be an ADAMTS13 polypeptide. In some embodiments, the agonist of ADAMTS13 can be an engineered and/or recombinant polypeptide. In some embodiments, the agonist of ADAMTS13 can be a nucleic acid encoding ADAMTS13, e.g. a functional fragment thereof. Further non-limiting examples of agonists of ADAMTS13 can include an antibody reagent that targets the A1 domain of von Willebrand factor (VWF); an aptamer that targets the A1 domain of von Willebrand factor (VWF); and N-acetylcyteine (NAC); GPIβα-Ig chimera; functional fragments of GPIβα and/or mimetics thereof, and Weibel-Palade body secretion inhibitors. GPIβα is a receptor of VWF, in particular, the extracellular domain of GPIβα binds to the A1 domain of VWF. Antibodies targeting the A1 domain of von Willebrand factor as well as epitopes located in the A1 domain of vWf are known in the art. For more discussion of targeting of the A1 domain of vWf see, e.g. Tan et al. Thromb Res 2008 121:519-526 and Depraetere et al. Blood 1998; each of which is incorporated by reference herein in its entirety. The interaction of GPIβα and VWF, as well as GpIβα-derived inhibitors are described in the art, see, e.g. Aponte-Santamaria et al. Biophys J 2015 108:2312-21; Brill et al. Blood 2011 117:1400-1407; each of which is incorporated by reference herein in their entireies. Non-limiting examples of Weibel-Palade body secretion can include colchicine; nocodazole; and TAT-NSF700.

As used herein, "VEGF inhibitor" refers to an inhibitor of VEGF levels and/or activity. VEGF activity can be inhibited by, e.g. agents that bind VEGF itself, thereby preventing interaction with its receptors. Such agents can include, e.g. antibody reagents (e.g. monoclonal antibodies) that bind specifically to VEGF and/or exogenous agents comprising the extracellular domain of a VEGF receptor. VEGF activity can also be inhibited by, e.g., inhibiting the activity of VEGF receptors, e.g. by a) antibody reagents that bind specifically to a VEGF receptor; b) tyrosine kinase inhibitors or c) receptor tyrosine kinase inhibitors. Non-limiting examples of VEGF inhibitors can include bevacizumab; sunitinib; aflibercept; pazopanib; axitinib; sorafenib; vandetanib; regorafenib; and ramucirumab. As used herein, the term "inhibitor" refers to an agent which can decrease the expression and/or activity of the targeted expression product (e.g. VEGF), e.g. by at least 10% or more, e.g. by 10% or more, 50% or more, 70% or more, 80% or more, 90% or more, 95% or more, or 98% or more. The efficacy of an inhibitor of, for example, VEGF, e.g. its ability to decrease the level and/or activity of VEGF can be determined, e.g. by measuring the level of an expression product of VEGF and/or the activity of VEGF. Methods for measuring the level of a given mRNA and/or polypeptide are known to one of skill in the art, e.g. RT-PCR with primers can be used to determine the level of RNA and Western blotting with an antibody (e.g. an anti-VEGF antibody, e.g. Cat No. ab1316; Abcam; Cambridge, Mass.) can be used to determine the level of a polypeptide. The activity of, e.g. VEGF can be determined using methods known in the art, e.g. using commercially available kits for VEGF activity (e.g. Cat No. PAHS-091Z; Qiagen, Valencia, Calif.). In some embodiments, the inhibitor can be an inhibitory nucleic acid; an aptamer; an antibody reagent; an antibody; or a small molecule.

In some embodiments of any of the aspects described herein, the subject can be a subject having a condition or diagnosed as having a condition selected from the group consisting of preeclampsia; VEGF-inhibitor associated TMA; TMA; thrombotic thrombocytic purpura (TPP); hemolytic uremic syndrome (HUS); Hemolysis, Elevated Liver enzymes and Low Platelet count syndrome (HELLP); drug induced thrombotic microangiopathy (e.g., TMA induced by cyclosprorine or tacrolimus); solid organ transplant; infection; hypertension; and cancer.

In some embodiments of any of the aspects described herein, the subject can be a subject at risk or at increased risk of developing a TMA. In some embodiments of any of the aspects described herein, the subject at risk or at increased risk of developing a TMA can be a subject having a condition or diagnosed as having a condition selected from the group consisting of preeclampsia; drug induced thrombotic microangiopathy (e.g., TMA induced by cyclosprorine or tacrolimus); solid organ transplant; infection; hypertension; and cancer. In some embodiments of any of the aspects described herein, the subject at risk or at increased risk of developing a TMA can be a subject determined to have an elevated level of expression of soluble VEGF receptor 1 (soluble fms-like tyrosine kinase 1; sFlt-1). In some embodiments of any of the aspects described herein, the subject at risk or at increased risk of developing a TMA can be a subject determined to have a reduced level of expression and/or activity of ADAMTS13.

In some embodiments of any of the aspects described herein, the subject can be a subject determined to have an elevated level of expression of soluble VEGF receptor 1 (soluble fms-like tyrosine kinase 1; sFlt-1). As used herein, "soluble VEGF receptor 1," "soluble fms-like tyrosine kinase 1," or "sFlt-1" refers to a splice variant of the VEGF receptor that disables pro-angiogenic factors in the blood. Sequences of sFlt-1 for a variety of species are known, e.g. human sFlt-1 (NCBI Gene ID: 2321) mRNA (NCBI Ref Seq: NM_001159920; SEQ ID NO: 3) and polypeptide (NCBI Ref Seq: NP_001153392; SEQ ID NO:4) sequences.

In some embodiments of any of the aspects described herein, the subject can be a subject determined to have a reduced level of expression and/or activity of ADAMTS13. In some embodiments, a subject with a reduced level of expression and/or activity of ADAMTS13 is a subject with a level of expression and/or activity of ADAMTS13 that is 50% or less of a reference level, e.g. 50% or less, 40% or less, 30% or less, 20% or less, or 10% or less. In some embodiments, a subject with a reduced level of expression and/or activity of ADAMTS13 is a subject with a level of expression and/or activity of ADAMTS13 that is 60% or less of a reference level, e.g. 60% or less, 50% or less, 40% or less, 30% or less, 20% or less, or 10% or less. In some embodiments, a subject with a reduced level of expression and/or activity of ADAMTS13 is a subject with a level of expression and/or activity of ADAMTS13 that is 70% or less of a reference level, e.g. 70% or less, 60% or less, 50% or less, 40% or less, 30% or less, 20% or less, or 10% or less.

As described herein, decreased ADAMTS13 levels and/or activity can exacerbate intestinal inflammation, e.g, in IBD models. Furthermore, treating subjects with intestinal inflammation can both treat the intestinal inflammation itself and reduce and/or prevent thrombotic events which such subjects are more likely to experience. Accordingly in one aspect, described herein is a method of treating intestinal inflammation in a subject in need thereof, the method comprising administering an agonist of ADAMTS13 to the subject. In one aspect, described herein is a method of treating or preventing thrombosis in a subject with intestinal inflammation, the method comprising administering an agonist of ADAMTS13 to the subject.

Furthermore, subjects with intestinal inflammation who have low ADAMTS13 levels and/or activity can benefit from treatment with an anticoagulant. In one aspect, described herein is a method of treating intestinal inflammation in a subject in need thereof, the method comprising administering an anticoagulant to a subject determined to have a reduced level of expression and/or activity of ADAMTS13. In some embodiments, the subject can be further administered an agonist of ADAMTS13.

In some embodiments, intestinal inflammation can be inflammatory bowel disease (IBD) or colitis. In some embodiments, a subject in need of treatment for intestinal inflammation can be a subject at risk or at increased risk of developing thrombosis. In some embodiments, the thrombosis can be deep vein thrombosis, pulmonary embolism, or an arterial thrombosis. In one aspect, described herein is an assay comprising: measuring the level of expression or activity of ADAMTS13 in a test sample obtained from a subject; wherein an decrease in the level relative to a reference level indicates the subject has a higher risk of having or developing thrombotic microangiopathy (TMA). In one aspect, described herein is a method of identifying a subject in need of treatment for thrombotic microangiopathy (TMA), the method comprising measuring the level or activity of ADAMTS13 in a test sample obtained from a subject; and identifying the subject as being in need of treatment for thrombotic microangiopathy (TMA) when the level of ADAMTS13 is decreased relative to a reference level. In one aspect, described herein is a method of determining if a subject is at risk for thrombotic microangiopathy (TMA), the method comprising: measuring the level or activity of ADAMTS13 in a test sample obtained from a subject; comparing the level of level or activity of ADAMTS13 in the sample to a reference level; determining that the subject is at risk for thrombotic microangiopathy (TMA) when the level is decreased relative to a reference level; and determining that the subject is not at risk for thrombotic microangiopathy (TMA) when the level is not decreased relative to a reference level.

In some embodiments, measurement of the level of a target, e.g. of an ADAMTS13 expression product can comprise a transformation. As used herein, the term "transforming" or "transformation" refers to changing an object or a substance, e.g., biological sample, nucleic acid or protein, into another substance. The transformation can be physical, biological or chemical. Exemplary physical transformation includes, but is not limited to, pre-treatment of a biological sample, e.g., from whole blood to blood serum by differential centrifugation. A biological/chemical transformation can involve the action of at least one enzyme and/or a chemical reagent in a reaction. For example, a DNA sample can be digested into fragments by one or more restriction enzymes, or an exogenous molecule can be attached to a fragmented DNA sample with a ligase. In some embodiments, a DNA sample can undergo enzymatic replication, e.g., by polymerase chain reaction (PCR).

Transformation, measurement, and/or detection of a target molecule, e.g. a ADAMTS13 mRNA or polypeptide can comprise contacting a sample obtained from a subject with a reagent (e.g. a detection reagent) which is specific for the target, e.g., an ADAMTS13-specific reagent. In some embodiments, the target-specific reagent is detectably labeled. In some embodiments, the target-specific reagent is capable of generating a detectable signal. In some embodiments, the target-specific reagent generates a detectable signal when the target molecule is present.

Methods to measure ADAMTS13 gene expression products are known to a skilled artisan. Such methods to measure gene expression products, e.g., protein level, include ELISA (enzyme linked immunosorbent assay), western blot, immunoprecipitation, and immunofluorescence using detection reagents such as an antibody or protein binding agents. Alternatively, a peptide can be detected in a subject by introducing into a subject a labeled anti-peptide antibody and other types of detection agent. For example, the antibody can be labeled with a detectable marker whose presence and location in the subject is detected by standard imaging techniques.

For example, antibodies for ADAMTS13 are commercially available and can be used for the purposes of the invention to measure protein expression levels, e.g. anti-ADAMTS13 (Cat. No. ab90786; Abcam, Cambridge Mass.). Alternatively, since the amino acid sequences for ADAMTS13 are known and publically available at NCBI website, one of skill in the art can raise their own antibodies against these polypeptides of interest for the purpose of the invention.

The amino acid sequences of the polypeptides described herein, e.g. ADAMTS13 have been assigned NCBI accession numbers for different species such as human, mouse and rat. In particular, the NCBI accession numbers for the amino acid sequence of human ADAMTS13 is included herein, e.g. SEQ ID NO: 2.

In some embodiments, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of an antibody, wherein the antibodies are used to specifically target molecules inside or on the surface of cells. The antibody typically contains a marker that will undergo a biochemical reaction, and thereby experience a change of color, upon encountering the targeted molecules. In some instances, signal amplification can be integrated into the particular protocol, wherein a secondary antibody, that includes the marker stain or marker signal, follows the application of a primary specific antibody.

In some embodiments, the assay can be a Western blot analysis. Alternatively, proteins can be separated by two-dimensional gel electrophoresis systems. Two-dimensional gel electrophoresis is well known in the art and typically involves iso-electric focusing along a first dimension followed by SDS-PAGE electrophoresis along a second dimension. These methods also require a considerable amount of cellular material. The analysis of 2D SDS-PAGE gels can be performed by determining the intensity of protein spots on the gel, or can be performed using immune detection. In other embodiments, protein samples are analyzed by mass spectroscopy.

Immunological tests can be used with the methods and assays described herein and include, for example, competitive and non-competitive assay systems using techniques such as Western blots, radioimmunoassay (RIA), ELISA (enzyme linked immunosorbent assay), "sandwich" immunoassays, immunoprecipitation assays, immunodiffusion assays, agglutination assays, e.g. latex agglutination, complement-fixation assays, immunoradiometric assays, fluorescent immunoassays, e.g. FIA (fluorescence-linked immunoassay), chemiluminescence immunoassays (CLIA), electrochemiluminescence immunoassay (ECLIA, counting immunoassay (CIA), lateral flow tests or immunoassay (LFIA), magnetic immunoassay (MIA), and protein A immunoassays. Methods for performing such assays are known in the art, provided an appropriate antibody reagent is available. In some embodiments, the immunoassay can be a quantitative or a semi-quantitative immunoassay.

An immunoassay is a biochemical test that measures the concentration of a substance in a biological sample, typically a fluid sample such as urine, using the interaction of an antibody or antibodies to its antigen. The assay takes advantage of the highly specific binding of an antibody with its antigen. For the methods and assays described herein, specific binding of the target polypeptides with respective proteins or protein fragments, or an isolated peptide, or a fusion protein described herein occurs in the immunoassay to form a target protein/peptide complex. The complex is then detected by a variety of methods known in the art. An immunoassay also often involves the use of a detection antibody.

Enzyme-linked immunosorbent assay, also called ELISA, enzyme immunoassay or EIA, is a biochemical technique used mainly in immunology to detect the presence of an antibody or an antigen in a sample. The ELISA has been used as a diagnostic tool in medicine and plant pathology, as well as a quality control check in various industries.

In one embodiment, an ELISA involving at least one antibody with specificity for the particular desired antigen (e.g., ADAMTS13 as described herein) can also be performed. A known amount of sample and/or antigen is immobilized on a solid support (usually a polystyrene micro titer plate). Immobilization can be either non-specific (e.g., by adsorption to the surface) or specific (e.g. where another antibody immobilized on the surface is used to capture antigen or a primary antibody). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In another embodiment, a competitive ELISA is used. Purified antibodies that are directed against a target polypeptide or fragment thereof are coated on the solid phase of multi-well plate, i.e., conjugated to a solid surface. A second batch of purified antibodies that are not conjugated on any solid support is also needed. These non-conjugated purified antibodies are labeled for detection purposes, for example, labeled with horseradish peroxidase to produce a detectable signal. A sample (e.g., a blood sample) from a subject is mixed with a known amount of desired antigen (e.g., a known volume or concentration of a sample comprising a target polypeptide) together with the horseradish peroxidase labeled antibodies and the mixture is then are added to coated wells to form competitive combination. After incubation, if the polypeptide level is high in the sample, a complex of labeled antibody reagent-antigen will form. This complex is free in solution and can be washed away. Washing the wells will remove the complex. Then the wells are incubated with TMB (3,3',5,5'-tetramethylbenzidene) color development substrate for localization of horseradish peroxidase-conjugated antibodies in the wells. There will be no color change or little color change if the target polypeptide level is high in the sample. If there is little or no target polypeptide present in the sample, a different complex in formed, the complex of solid support bound antibody reagents-target polypeptide. This complex is immobilized on the plate and is not washed away in the wash step. Subsequent incubation with TMB will produce significant color change. Such a competitive ELSA test is specific, sensitive, reproducible and easy to operate.

There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; and Oellerich, M. 1984, J. Clin. Chem. Clin. Biochem. 22:895-904. These references are hereby incorporated by reference in their entirety.

In one embodiment, the levels of a polypeptide in a sample can be detected by a lateral flow immunoassay test (LFIA), also known as the immunochromatographic assay, or strip test. LFIAs are a simple device intended to detect the presence (or absence) of antigen, e.g. a polypeptide, in a fluid sample. There are currently many LFIA tests used for medical diagnostics, either for home testing, point of care testing, or laboratory use. LFIA tests are a form of immunoassay in which the test sample flows along a solid substrate via capillary action. After the sample is applied to the test strip it encounters a colored reagent (generally comprising antibody specific for the test target antigen) bound to microparticles which mixes with the sample and transits the substrate encountering lines or zones which have been pretreated with another antibody or antigen. Depending upon the level of target polypeptides present in the sample the colored reagent can be captured and become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water, and/or homogenized tissue samples etc. Strip tests are also known as dip stick tests, the name bearing from the literal action of "dipping" the test strip into a fluid sample to be tested. LFIA strip tests are easy to use, require minimum training and can easily be included as components of point-of-care test (POCT) diagnostics to be use on site in the field. LFIA tests can be operated as either competitive or sandwich assays. Sandwich LFIAs are similar to sandwich ELISA. The sample first encounters colored particles which are labeled with antibodies raised to the target antigen. The test line will also contain antibodies to the same target, although it may bind to a different epitope on the antigen. The test line will show as a colored band in positive samples. In some embodiments, the lateral flow immunoassay can be a double antibody sandwich assay, a competitive assay, a quantitative assay or variations thereof. Competitive LFIAs are similar to competitive ELISA. The sample first encounters colored particles which are labeled with the target antigen or an analogue. The test line contains antibodies to the target/its analogue. Unlabelled antigen in the sample will block the binding sites on the antibodies preventing uptake of the colored particles. The test line will show as a colored band in negative samples. There are a number of variations on lateral flow technology. It is also possible to apply multiple capture zones to create a multiplex test.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Examples of patents that describe the use of "dip stick" technology to detect soluble antigens via immunochemical assays include, but are not limited to U.S. Pat. Nos. 4,444,880; 4,305,924; and 4,135,884; which are incorporated by reference herein in their entireties. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teachings of this "dip stick" technology for the detection of polypeptides using antibody reagents as described herein.

Other techniques can be used to detect the level of a polypeptide in a sample. One such technique is the dot blot, and adaptation of Western blotting (Towbin et at., Proc. Nat. Acad. Sci. 76:4350 (1979)). In a Western blot, the polypeptide or fragment thereof can be dissociated with detergents and heat, and separated on an SDS-PAGE gel before being transferred to a solid support, such as a nitrocellulose or PVDF membrane. The membrane is incubated with an antibody reagent specific for the target polypeptide or a fragment thereof. The membrane is then washed to remove unbound proteins and proteins with non-specific binding. Detectably labeled enzyme-linked secondary or detection antibodies can then be used to detect and assess the amount of polypeptide in the sample tested. The intensity of the signal from the detectable label corresponds to the amount of enzyme present, and therefore the amount of polypeptide. Levels can be quantified, for example by densitometry.

In some embodiments, the level of, e.g., ADAMTS13, can be measured, by way of non-limiting example, by Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy and/or immunoelectrophoresis assay.

In certain embodiments, the gene expression products as described herein can be instead determined by determining the level of messenger RNA (mRNA) expression of the genes described herein, e.g. ADAMTS13. Such molecules can be isolated, derived, or amplified from a biological sample, such as a blood sample. Techniques for the detection of mRNA expression is known by persons skilled in the art, and can include but not limited to, PCR procedures, RT-PCR, quantitative RT-PCR Northern blot analysis, differential gene expression, RNAse protection assay, microarray based analysis, next-generation sequencing; hybridization methods, etc.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments, the level of an mRNA can be measured by a quantitative sequencing technology, e.g. a quantitative next-generation sequence technology. Methods of sequencing a nucleic acid sequence are well known in the art. Briefly, a sample obtained from a subject can be contacted with one or more primers which specifically hybridize to a single-strand nucleic acid sequence flanking the target gene sequence and a complementary strand is synthesized. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g. by determining the location and pattern of the hybridization of probes, or measuring one or more characteristics of a single molecule as it passes through a sensor (e.g. the modulation of an electrical field as a nucleic acid molecule passes through a nanopore). Exemplary methods of sequencing include, but are not limited to, Sanger sequencing, dideoxy chain termination, high-throughput sequencing, next generation sequencing, 454 sequencing, SOLiD sequencing, polony sequencing, Illumina sequencing, Ion Torrent sequencing, sequencing by hybridization, nanopore sequencing, Helioscope sequencing, single molecule real time sequencing, RNAP sequencing, and the like. Methods and protocols for performing these sequencing methods are known in the art, see, e.g. "Next Generation Genome Sequencing" Ed. Michal Janitz, Wiley-VCH; "High-Throughput Next Generation Sequencing" Eds. Kwon and Ricke, Humanna Press, 2011; and Sambrook et al., Molecular Cloning: A Laboratory Manual (4 ed.), Cold Spring Harbor Laboratory Press, Cold Spring Harbor, N.Y., USA (2012); which are incorporated by reference herein in their entireties.

The nucleic acid sequences of the genes described herein, e.g., ADAMTS13, have been assigned NCBI accession numbers for different species such as human, mouse and rat. For example, the human ADAMTS13 mRNA (e.g. SEQ ID NO: 1) is known. Accordingly, a skilled artisan can design an appropriate primer based on the known sequence for determining the mRNA level of the respective gene.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In some embodiments, detecting decreased activity and/or expression of ADAMTS13 can comprise detecting the present of an ADAMTS13-dampening mutation, i.e. a mutation the decreases the activity and/or level of ADAMTS13. A number of such mutations are known in the art, e.g. associated with congenital diseases or predisposition to conditions described herein. Non-limiting examples of such mutations can comprise, e.g. c.1308G>C; c.428T>C (p.Ile143Thr); c.1709A>G (p.Tyr570Cys); C1213Y, W1245del; and K1256FS; pR1060W; pR193W; p.A250V; pR268S; p.C508Y; 9.I673F; p.C908Y; p.R1123C; p.Q449X; c.4143_4144insA; C.106_107delAG; p.P475S; p.P618A; p.Q448E; and p.R1336W. Further discussion of such mutations can be found in the art, e.g., Perez-Rodriguez et al. Thromb Res 2014 134:1171-5; Metin et al. Pediatr Blood Cancer 2014 61:558-561; Zhou et al. Thromb Res 2009 124:323-7; and Lotta et al., J Thromb Heamost 2013 11:1228-1239; each of which is incorporated by reference herein in its entirety.

In some embodiments, the assays and methods can relate to detecting the presence of a mutation, e.g. a ADAMTS13 dampening mutation in a sample obtained from a subject. In some embodiments, the presence of the mutation can be determined using an assay selected from the group consisting of: hybridization; sequencing; exome capture; PCR; high-throughput sequencing; allele-specific probe hybridization; allele-specific primer extension, allele-specific amplification; 5' nuclease digestion; molecular beacon assay; oligonucleotide ligation assay; size analysis; single-stranded conformation polymorphism; real-time quantitative PCR, and any combinations thereof.

In some embodiments, the presence and/or absence of a mutation can be detected by determining the sequence of a genomic locus and/or an mRNA transcript. Such molecules can be isolated, derived, or amplified from a biological sample, such as a tumor sample. Nucleic acid (e.g. DNA) and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; and proteinase K extraction can be used to obtain nucleic acid from blood (Roiff, A et al. PCR: Clinical Diagnostics and Research, Springer (1994)).

In some embodiments, the nucleic acid sequence of a target gene (e.g. ADAMTS13) in a sample obtained from a subject can be determined and compared to a reference sequence to determine if a mutation is present in the subject. In some embodiments, the sequence of the target gene can be determined by sequencing the target gene (e.g. the genomic sequence and/or the mRNA transcript thereof). Methods of sequencing a nucleic acid sequence are well known in the art. Briefly, a sample obtained from a subject can be contacted with one or more primers which specifically hybridize to a single-strand nucleic acid sequence flanking the target gene sequence and a complementary strand is synthesized. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g. by determining the location and pattern of the hybridization of probes, or measuring one or more characteristics of a single molecule as it passes through a sensor (e.g. the modulation of an electrical field as a nucleic acid molecule passes through a nanopore). Exemplary methods of sequencing include, but are not limited to, Sanger sequencing, dideoxy chain termination, high-throughput sequencing, next generation sequencing, 454 sequencing, SOLiD sequencing, polony sequencing, Illumina sequencing, Ion Torrent sequencing, sequencing by hybridization, nanopore sequencing, Helioscope sequencing, single molecule real time sequencing, RNAP sequencing, and the like. Methods and protocols for performing these sequencing methods are known in the art, see, e.g. "Next Generation Genome Sequencing" Ed. Michal Janitz, Wiley-VCH; "High-Throughput Next Generation Sequencing" Eds. Kwon and Ricke, Humanna Press, 2011; and Sambrook et al., Molecular Cloning: A Laboratory Manual (3 ed.), Cold Spring Harbor Laboratory Press, Cold Spring Harbor, N.Y., USA (2001); which are incorporated by reference herein in their entireties.

In some embodiments, sequencing can comprise exome sequencing (i.e. targeted exome capture). Exome sequencing comprises enriching for an exome(s) of interest and then sequencing the nucleic acids comprised by the enriched sample. Sequencing can be according to any method known in the art, e.g. those described above herein. Methods of enrichment can include, e.g. PCR, molecular inversion probes, hybrid capture, and in solution capture. Exome capture methodologies are well known in the art, see, e.g. Sulonen et al. Genome Biology 2011 12:R94; and Teer and Mullikin. Hum Mol Genet 2010 19:R2; which are incorporated by reference herein in their entireties. Kits for performing exome capture are available commercially, e.g. the TRUSEQ™ Exome Enrichment Kit (Cat. No. FC-121-1008; Illumnia, San Diego, Calif.). Exome capture methods can also readily be adapted by one of skill in the art to enrich specific exomes of interest.

In some embodiments, the presence of a mutation can be determined using a probe that is specific for the mutation. In some embodiments, the probe can be detectably labeled. In some embodiments, a detectable signal can be generated by the probe when a mutation is present.

In some embodiments, the probe specific for the mutation can be a probe in a hybridization assay, i.e. the probe can specifically hybridize to a nucleic acid comprising a mutation (as opposed to a wild-type nucleic acid sequence) and the hybridization can be detected, e.g. by having the probe and or the target nucleic acid be detectably labeled. Hybridization assays are well known in the art and include, e.g. northern blots and Southern blots.

In some embodiments, the probe specific for the mutation can be a probe in a PCR assay, i.e. a primer. In general, the PCR procedure describes a method of gene amplification which is comprised of (i) sequence-specific hybridization of primers to specific genes within a nucleic acid sample or library, (ii) subsequent amplification involving multiple rounds of annealing, elongation, and denaturation using a thermostable DNA polymerase, and optionally, (iii) screening the PCR products for a band or product of the correct size. The primers used are oligonucleotides of sufficient length and appropriate sequence to provide initiation of polymerization, i.e. each primer is specifically designed to be complementary to a strand of the genomic locus to be amplified. In an alternative embodiment, the presence of a mutation in an mRNA transcript can be determined by reverse-transcription (RT) PCR and by quantitative RT-PCR (QRT-PCR) or real-time PCR methods. Methods of RT-PCR and QRT-PCR are well known in the art. In some embodiments, the PCR product can be labeled, e.g. the primers can comprise a detectable label, or a label can be incorporated and/or bound to the PCR product, e.g. EtBr detection methods. Other non-limiting detection methods can include the detection of a product by mass spectroscopy or MALDI-TOF.

In some embodiments, one or more of the reagents (e.g. an antibody reagent and/or nucleic acid probe) described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is label with a fluorescent compound. When the fluorescently labeled reagent is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6 carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments, a detectable label can be a radiolabel including, but not limited to $^3$H, $^{125}$I, $^{35}$S, $^{14}$C, $^{32}$P, and $^{33}$P. In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments, a detectable label is a chemiluminescent label, including, but not limited to lucigenin, luminol, luciferin, isoluminol, theromatic acridinium ester, imidazole, acridinium salt and oxalate ester. In some embodiments, a detectable label can be a spectral colorimetric label including, but not limited to colloidal gold or colored glass or plastic (e.g., polystyrene, polypropylene, and latex) beads.

In some embodiments, detection reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i.e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e.g. from DAKO; Carpinteria, Calif. A reagent can also be detectably labeled using fluorescence emitting metals such as $^{152}$Eu, or others of the lanthanide series. These metals can be attached to the reagent using such metal chelating groups as diethylenetriaminepentaacetic acid (DTPA) or ethylenediaminetetraacetic acid (EDTA).

A level which is less than a reference level can be a level which is less by at least about 10%, at least about 20%, at least about 50%, at least about 60%, at least about 80%, at least about 90%, or less than the reference level. In some embodiments, a level which is less than a reference level can be a level which is statistically significantly less than the reference level. In some embodiments, the reference can be a level of ADAMTS13 in a population of subjects who do not have or are not diagnosed as having, and/or do not exhibit signs or symptoms of a TMA. In some embodiments, the reference can also be a level of expression of ADAMTS13 in a control sample, a pooled sample of control individuals or a numeric value or range of values based on the same. In some embodiments, the reference can be the level of ADAMTS13 in a sample obtained from the same subject at an earlier point in time, e.g., the methods described herein can be used to determine if a subject's risk or likelihood of developing a TMA is increasing.

In some embodiments, the level of expression products of no more than 200 other genes is determined. In some embodiments, the level of expression products of no more than 100 other genes is determined. In some embodiments, the level of expression products of no more than 20 other genes is determined. In some embodiments, the level of expression products of no more than 10 other genes is determined.

In some embodiments of the foregoing aspects, the expression level of a given gene, e.g., ADAMTS13, can be normalized relative to the expression level of one or more reference genes or reference proteins.

The term "sample" or "test sample" as used herein denotes a sample taken or isolated from a biological organism, e.g., a blood or plasma sample from a subject. Exemplary biological samples include, but are not limited to, a biofluid sample; serum; plasma; urine; saliva; and/or tissue sample etc. The term also includes a mixture of the above-mentioned samples. The term "test sample" also includes untreated or pretreated (or pre-processed) biological samples. In some embodiments, a test sample can comprise cells from a subject. In some embodiments, the test sample can be blood; plasma; urine, or serum.

The test sample can be obtained by removing a sample from a subject, but can also be accomplished by using a previously isolated sample (e.g. isolated at a prior timepoint and isolated by the same or another person).

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

In some embodiments, the methods, assays, and systems described herein can further comprise a step of obtaining a test sample from a subject. In some embodiments, the subject can be a human subject. In some embodiments, the subject can be a subject in need of treatment for (e.g. having or diagnosed as having) a TMA or a subject at risk of or at increased risk of developing a TMA as described elsewhere herein.

In one aspect, described herein is a method of determining the efficacy of a treatment for thrombotic microangiopathy (TMA), the method comprising a) measuring the level or activity of ADAMTS13 in a test sample obtained from a subject before administration of the treatment; b) measuring the level or activity of ADAMTS13 in a test sample obtained from a subject after administration of the treatment; c) determining that the treatment is efficacious when the level determined in step (b) is not decreased relative to the level determined in step (a); and d) determining that the treatment is not efficacious when the level determined in step (b) is decreased relative to the level determined in step (a).

In one aspect, described herein is a method of treatment for thrombotic microangiopathy (TMA) comprising; measuring the level or activity of ADAMTS13 in a test sample obtained from a subject; and treating the subject for TMA when the level is decreased relative to a reference level. In one aspect, described herein is a method of treatment for thrombotic microangiopathy (TMA) comprising; administering a treatment for TMA to a subject determined to have a level or activity of ADAMTS13 which is decreased relative to a reference level.

In some embodiments, a treatment for a TMA can be selected from the group consisting of an agonist of ADAMTS13; an ADAMTS13 polypeptide or functional fragment thereof; a recombinant ADAMTS13 polypeptide or functional fragment thereof; an engineered ADAMTS13 polypeptide or functional fragment thereof; a nucleic acid encoding an ADAMTS13 polypeptide or functional fragment thereof; a recombinant nucleic acid encoding an ADAMTS13 polypeptide or functional fragment thereof; an engineered nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC); GPIβα-Ig chimera; functional fragments of GPIβα and/or mimetics thereof; and Weibel-Palade body secretion inhibitors. In some embodiments, a method or assay described herein can further comprise the step of administering a treatment for a TMA.

In some embodiments, the methods described herein relate to treating a subject having or diagnosed as having TMA with an agonist of ADAMTS13. Subjects having TMA can be identified by a physician using current methods of diagnosing TMA. Symptoms and/or complications of TMA which characterize these conditions and aid in diagnosis are well known in the art and include but are not limited to, fever, renal failure, thrombocytopenia, neurological manifestations, and microangiopathic hemolytic anemia. Tests that may aid in a diagnosis of, e.g. TMA include, but are not limited to, blood smears and blood tests. A family history of TMA, or exposure to risk factors for TMA (e.g. VEGF inhibitors, preeclampsia, or solid organ transplant) can also aid in determining if a subject is likely to have TMA or in making a diagnosis of TMA.

The compositions and methods described herein can be administered to a subject having or diagnosed as having a condition described herein, e.g. TMA, cancer, or preeclampsia. In some embodiments, the methods described herein comprise administering an effective amount of compositions described herein, e.g. an agonist of ADAMTS13 to a subject in order to alleviate a symptom of a condition. As used herein, "alleviating a symptom" is ameliorating any condition or symptom associated with a condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of, e.g., an agonist of ADAMTS13 needed to alleviate at least one or more symptom of the disease or disorder, and relates to a sufficient amount of pharmacological composition to provide the desired effect. The term "therapeutically effective amount" therefore refers to an amount of a compound that is sufficient to provide a particular therapeutic effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for ADAMTS13 levels among others. The dosage can be determined by a physician and adjusted, as necessary, to suit observed effects of the treatment.

In some embodiments, the technology described herein relates to a pharmaceutical composition comprising an agonist of ADAMTS13 as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. an agonist of ADAMTS13 as described herein.

In some embodiments, the pharmaceutical composition comprising an agonist of ADAMTS13 as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of an agonist of ADAMTS13 as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a compound as disclosed herein can also be incorporated into the parenteral dosage forms of the disclosure, including conventional and controlled-release parenteral dosage forms.

Pharmaceutical compositions comprising an agonist of ADAMTS13 can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the agonist of ADAMTS13 can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. Agents and/or treatment appropriate for the various conditions described herein are known in the art. For example, non-limiting examples of a second agent and/or treatment for cancer can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide;

mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

In certain embodiments, an effective dose of a composition comprising an agonist of ADAMTS13 as described herein can be administered to a patient once. In certain embodiments, an effective dose of a composition comprising an agonist of ADAMTS13 can be administered to a patient repeatedly. For systemic administration, subjects can be administered a therapeutic amount of a composition comprising an agonist of ADAMTS13, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more. For systemic administration, subjects can be administered a therapeutic amount of a composition comprising an ADAMTS13 polypeptide (e.g. a recombinant ADAMTS13 polypeptide), such as, e.g. about 1000-5000 U/kg/day, about 2000-4500 U/kg/day, about 3000-4000 U/kg/day, or about 3500 U/kg/day. For systemic administration, subjects can be administered a therapeutic amount of a composition comprising an ADAMTS13 polypeptide (e.g. a recombinant ADAMTS13 polypeptide), such as, e.g. 1000-5000 U/kg/day, 2000-4500 U/kg/day, 3000-4000 U/kg/day, or 3500 U/kg/day.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the agonist of ADAMTS13. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an agonist of ADAMTS13 can be administered over a period of time, such as over a 5 minute, 10 minute, 15 minute, 20 minute, or 25 minute period.

The dosage ranges for the administration of, e.g., an agonist of ADAMTS13, according to the methods described herein depend upon, for example, the form of an agonist of ADAMTS13, its potency, and the extent to which symptoms, markers, or indicators of a condition described herein are desired to be reduced, for example the percentage increase of ADAMTS13 levels, or the extent to which, for example, symptoms of TMA are desired to be reduced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an agonist of ADAMTS13 in, e.g. the treatment of a condition described herein, or to induce a response as described herein (e.g. an increase in ADAMTS13 expression and/or activity levels) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. ADAMTS13 levels. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. symptoms of TMA and/or ADAMTS13 levels). It is well within the ability of one skilled in the art to monitor efficacy of administration and/or treatment by measuring any one of such parameters, or any combination of parameters. Efficacy can be assessed in animal models of a condition described herein, for example treatment of mouse models of TMA. When using an experimental animal model, efficacy of treatment is evidenced when a statistically significant change in a marker is observed, e.g. ADAMTS13 levels.

In vitro and animal model assays are provided herein which allow the assessment of a given dose of an agonist of ADAMTS13. By way of non-limiting example, the effects of a dose of an agonist of ADAMTS13 can be assessed by administering the agonist to ADAMTS12−/− mice, e.g. with or without secondary TMA-inducing factors (e.g. the administration of a sFlt-1 overexpression adenovirus). The agonist can be administered, e.g. by intravenous injection. Efficacy can be measured by, e.g., blood pressure measurements, blood smears to detect schistocytes and reticulocytes, VWF levels, glomerular area and open capillary volume analysis of tissues, and determination of albumin and cretatinine urine levels.

In one aspect, described herein is a kit for performing any of the assays and/or methods described herein. In some embodiments, the kit can comprise a ADAMTS13-specific reagent.

A kit is any manufacture (e.g., a package or container) comprising at least one reagent, e.g., an antibody reagent(s) or nucleic acid probe, for specifically detecting, e.g., a ADAMTS13 expression product or fragment thereof, the manufacture being promoted, distributed, or sold as a unit for performing the methods or assays described herein. When the kits, and methods described herein are used for diagnosis and/or treatment of TMA in patients, the reagents (e.g., detection probes) or systems can be selected such that a positive result is obtained in at least about 20%, at least about 40%, at least about 60%, at least about 80%, at least about 90%, at least about 95%, at least about 99% or in 100% of subjects having or developing a TMA.

In some embodiments, described herein is a kit for the detection of a ADAMTS13 expression product in a sample, the kit comprising at least a first ADAMTS13-specific reagent as described herein which specifically binds the ADAMTS13 expression product, on a solid support and comprising a detectable label. The kits described herein include reagents and/or components that permit assaying the level of an expression product in a sample obtained from a subject (e.g., a biological sample obtained from a subject). The kits described herein can optionally comprise additional components useful for performing the methods and assays described herein.

A kit can further comprise devices and/or reagents for concentrating an expression product (e.g, a polypeptide) in a sample, e.g. a plasma sample. Thus, ultrafiltration devices permitting, e.g., protein concentration from plasma can also be included as a kit component.

Preferably, a diagnostic or prognostic kit for use with the methods and assays disclosed herein contains detection reagents for ADAMTS13 expression products. Such detection reagents comprise in addition to ADAMTS13-specific reagents, for example, buffer solutions, labels or washing liquids etc. Furthermore, the kit can comprise an amount of a known nucleic acid and/or polypeptide, which can be used for a calibration of the kit or as an internal control. A diagnostic kit for the detection of an expression product can also comprise accessory ingredients like secondary affinity ligands, e.g., secondary antibodies, detection dyes and any other suitable compound or liquid necessary for the performance of a expression product detection method known to the person skilled in the art. Such ingredients are known to the person skilled in the art and may vary depending on the detection method carried out. Additionally, the kit may comprise an instruction leaflet and/or may provide information as to the relevance of the obtained results.

In some aspects, the invention described herein is directed to systems (and computer readable media for causing computer systems) for obtaining data from at least one sample obtained from at least one subject, the system comprising 1) a measuring module configured to receive the at least one sample and perform at least one analysis on the at least one sample to determine the level (e.g. expression level and/or activity level) of ADAMTS13 in the sample; 2) a storage device configured to store data output from the determination module; and 3) a display module for displaying a content based in part on the data output from the determination module, wherein the content comprises a signal indicative of the level (e.g. expression level and/or activity level) of ADAMTS13.

Figure 8:
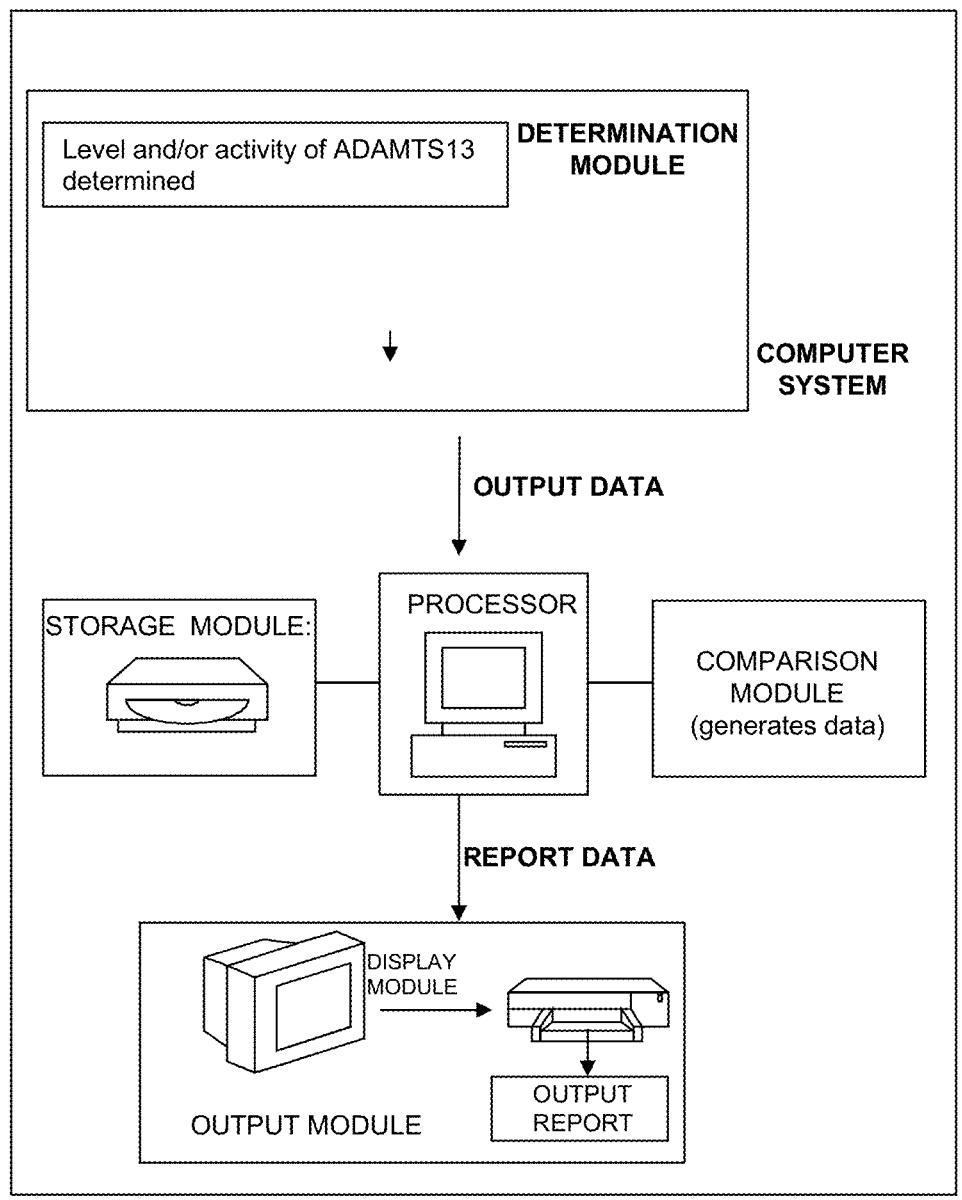
FIG. 8 is a diagram of an exemplary embodiment of a system for performing an assay for determining the level of ADAMTS13 in a sample obtained from a subject.

In one embodiment, provided herein is a system comprising: (a) at least one memory containing at least one computer program adapted to control the operation of the computer system to implement a method that includes a measuring module configured to measure the level of ADAMTS13 in a test sample obtained from a subject; a storage module configured to store output data from the determination module; a comparison module adapted to compare the data stored on the storage module with a reference level, and to provide a retrieved content, and a display module for displaying whether the sample comprises a level of ADAMTS13 which is significantly decreases relative to the reference expression level and/or displaying the relative level of ADAMTS13 and (b) at least one processor for executing the computer program (see FIG. 8).

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super minicomputer; a mini-computer; a workstation; a micro-computer; a server; an interactive television; a hybrid combination of a computer and an interactive television; a tablet; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip. The term a "computer system" may refer to a system having a computer, where the computer comprises a computer-readable medium embodying software to operate the computer. The term "software" is used interchangeably herein with "program" and refers to prescribed rules to operate a computer. Examples of software include: software; code segments; instructions; computer programs; and programmed logic.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The functional modules of certain embodiments of the invention include at minimum a measuring module, a storage module, a computing module, and a display module. The functional modules can be executed on one, or multiple, computers, or by using one, or multiple, computer networks. The measuring module has computer executable instructions to provide e.g., levels of expression products etc in computer readable form.

The measuring module can comprise any system for detecting a signal elicited from an assay to determine the level and/or activity of ADAMTS13 described above herein. In some embodiments, such systems can include an instrument, e.g., AU2700 (Beckman Coulter Brea, Calif.) as described herein for quantitative measurement of polypeptides or e.g., a real time PCR machine, e.g. a LIGHTCYCLER™ (Roche). In some embodiments, the measuring module can measure the intensity of a detectable signal from an assay indicating the level of ADAMTS13 polypeptide in the test sample. In some embodiments, the assay can be an immunoassay. In some embodiments, the measuring module can measure the intensity of a detectable signal from a RT-PCR assay indicating the level of ADAMTS13 RNA transcript in the test sample.

The information determined in the determination system can be read by the storage module. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon, for example, sample name, biomolecule assayed and the level of said biomolecule. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In some embodiments of any of the systems described herein, the storage module stores the output data from the determination module. In additional embodiments, the storage module stores reference information such as levels of ADAMTS13 in healthy subjects and/or a population of healthy subjects.

Figure 9:
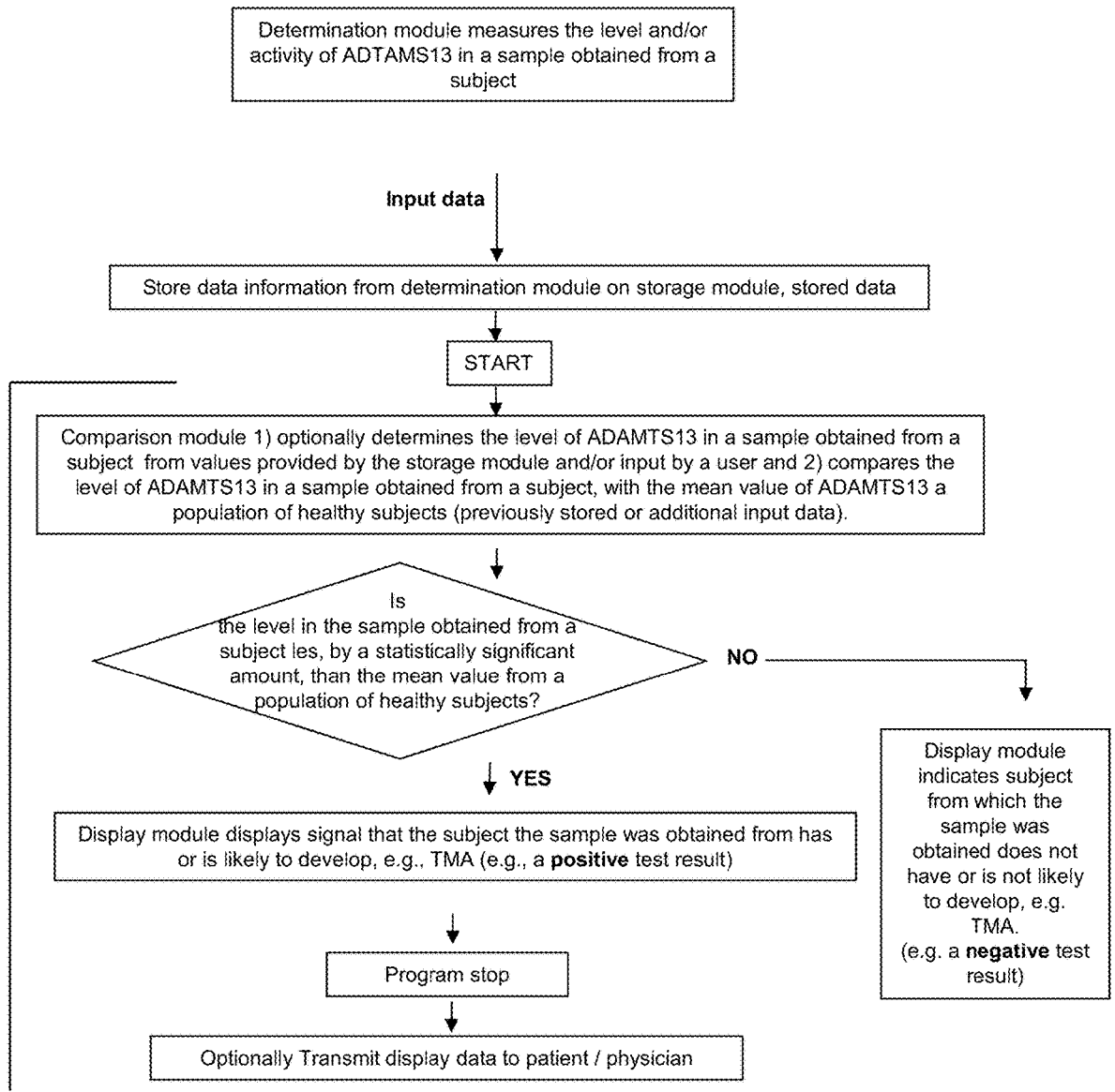
FIG. 9 is a diagram of an exemplary embodiment of a comparison module as described herein.

The "computing module" can use a variety of available software programs and formats for computing the level of ADAMTS13. Such algorithms are well established in the art. A skilled artisan is readily able to determine the appropriate algorithms based on the size and quality of the sample and type of data. The data analysis tools and equations described herein can be implemented in the computing module of the invention. In one embodiment, the computing module further comprises a comparison module, which compares the level of ADAMTS13 in a sample obtained from a subject as described herein with the mean value of ADAMTS13 in a population of healthy subjects (FIG. 9). By way of an example, when the value of ADAMTS13 in a sample obtained from a subject is measured, a comparison module can compare or match the output data with the mean value of ADAMTS13 in a population of healthy subjects. In certain embodiments, the mean value of ADAMTS13 in a population of healthy subjects can be pre-stored in the storage module. In various embodiments, the comparison module can be configured using existing commercially-available or freely-available software for comparison purpose, and may be optimized for particular data comparisons that are conducted.

Figure 10:
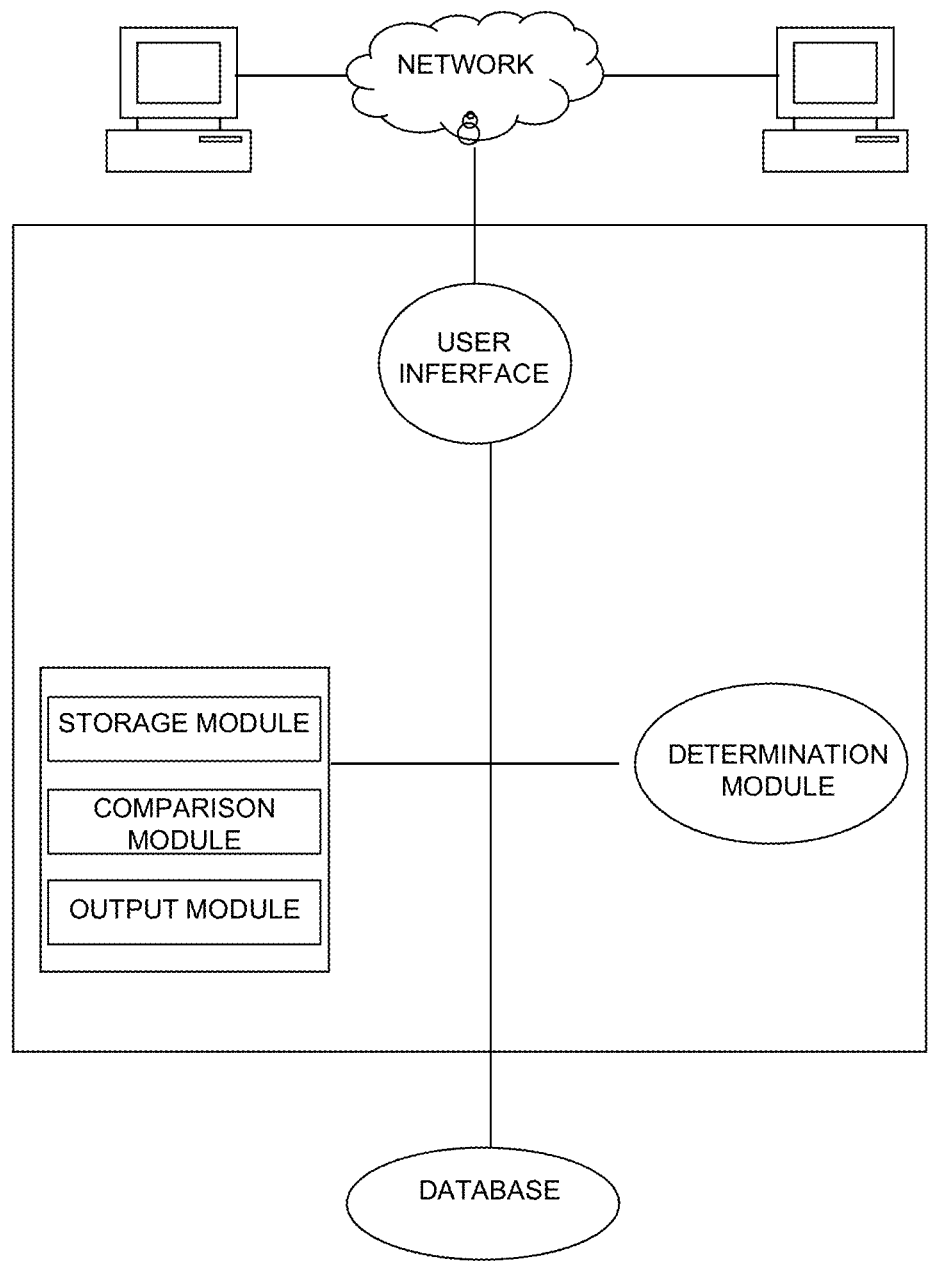
FIG. 10 is a diagram of an exemplary embodiment of an operating system and applications for a computing system as described herein.

The computing and/or comparison module, or any other module of the invention, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). In some embodiments users can directly access data (via Hypertext links for example) residing on Internet databases using a HTML interface provided by Web browsers and Web servers (FIG. 10).

The computing and/or comparison module provides a computer readable comparison result that can be processed in computer readable form by predefined criteria, or criteria defined by a user, to provide content based in part on the comparison result that may be stored and output as requested by a user using an output module, e.g., a display module.

In some embodiments, the content displayed on the display module can be the level of ADAMTS13 in the sample obtained from a subject. In some embodiments, the content displayed on the display module can be the relative level of ADAMTS13 in the sample obtained from a subject as compared to the mean level of ADAMTS13 in a population of healthy subjects. In some embodiments, if the computing module determines that the level of ADAMTS13 in the test sample obtained from a subject is less by a statistically significant amount than the reference level, the display module displays a signal indicating that the levels in the sample obtained from a subject are less than those of the reference level. In some embodiments, the signal indicates the subject is in need of treatment for TMA. In some embodiments, the signal indicates the degree to which the level of ADAMTS13 in the sample obtained from a subject varies from the reference level. In some embodiments, the content displayed on the display module can indicate whether the subject has an increased likelihood of having or developing TMA. In some embodiments, the content displayed on the display module can be a numerical value indicating one of these risks or probabilities. In such embodiments, the probability can be expressed in percentages or a fraction. For example, higher percentage or a fraction closer to 1 indicates a higher likelihood of a subject having or developing TMA. In some embodiments, the content displayed on the display module can be single word or phrases to qualitatively indicate a risk or probability. For example, a word "unlikely" can be used to indicate a lower risk for having or developing TMA, while "likely" can be used to indicate a high risk for having or developing TMA.

In one embodiment of the invention, the content based on the computing and/or comparison result is displayed on a computer monitor. In one embodiment of the invention, the content based on the computing and/or comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the computing/comparison result. It should be understood that other modules of the invention can be adapted to have a web browser interface. Through the Web browser, a user can construct requests for retrieving data from the computing/comparison module. Thus, the user will typically point and click to user interface elements such as buttons, pull down menus, scroll bars and the like conventionally employed in graphical user interfaces.

Systems and computer readable media described herein are merely illustrative embodiments of the invention for determining the level and/or activity of ADAMTS13 in a sample obtained from a subject, and therefore are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of, e.g. thrombotic microangiopathy. A subject can be male or female.

A subject can be one who has been previously diagnosed with or identified as suffering from or having a condition in need of treatment (e.g. TMA) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, "preeclampsia" refers to a condition occurring during pregnancy that is characterized by high blood pressure and high proteinuremia. Preeclampsia can progress to, e.g. low platelet counts, red cell defiencies, liver and/or kidney disfunction, fluid in the lungs, and/or seizures.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs. Hemopoietic cancers, such as leukemia, are able to out-compete the normal hemopoietic compartments in a subject, thereby leading to hemopoietic failure (in the form of anemia, thrombocytopenia and neutropenia) ultimately causing death. A subject with cancer, e.g. a tumor or solid tumor, can benefit from the inhibition of angiogenesis, as formation of new blood vessels is required for the formation, growth, and/or maintenance of tumors.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm.; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice. See, e.g., Freshney, CULTURE ANIMAL CELLS: MANUAL BASIC TECH. (3rd ed., 1994).

As used herein, "engineered" refers to the aspect of having been manipulated by the hand of man. For example, a ADAMTS13 polypeptide is considered to be "engineered" when the sequence of the polypeptide and/or encoding nucleic acid sequence manipulated by the hand of man to differ from the sequence of an polypeptide as it exists in nature. As is common practice and is understood by those in the art, progeny and copies of an engineered polynucleotide and/or polypeptide are typically still referred to as "engineered" even though the actual manipulation was performed on a prior entity.

As used herein, "recombinant" refers to a cell, tissue or organism that has undergone transformation with a new combination of genes or DNA. When used in reference to nucleic acid molecules, "recombinant" refers to a combination of nucleic acid molecules that are joined together using recombinant DNA technology into a progeny nucleic acid molecule, and/or a heterologous nucleic acid sequence introduced into a cell, tissue, or organism. When used in reference to a polypeptide, "recombinant" refers to a polypeptide which is the expression product of a recombinant nucleic acid, and can be such a polypeptide as produced by a recombinant cell, tissue, or organisms. The nucleic acid molecule can be stably integrated into the genome of the host or the nucleic acid molecule can also be present as an extrachromosomal molecule. Such an extrachromosomal molecule can be auto-replicating. Recombinant viruses, cells, and organisms are understood to encompass not only the end product of a transformation process, but also recombinant progeny thereof.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, a particular "polypeptide", e.g. an ADAMTS13 polypeptide can include the human polypeptide (e.g., SEQ ID NO: 2); as well as homologs from other species, including but not limited to bovine, dog, cat chicken, murine, rat, porcine, ovine, turkey, horse, fish, baboon and other primates. The terms also refer to fragments or variants of the native polypeptide that maintain at least 50% of the activity or effect of the native full length polypeptide, e.g. as measured in an appropriate animal model. Conservative substitution variants that maintain the activity of wildtype polypeptides will include a conservative substitution as defined herein. The identification of amino acids most likely to be tolerant of conservative substitution while maintaining at least 50% of the activity of the wildtype is guided by, for example, sequence alignment with homologs or paralogs from other species. Amino acids that are identical between homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants can be tested for activity, for example, by administering the variant to an appropriate animal model of TMA as described herein, e.g., the ADAMTS13−/− animal model administered anti-VEGF agents.

In some embodiments, a polypeptide, e.g., an ADAMTS13 polypeptide, can be a variant of a sequence described herein, e.g. a variant of an ADAMTS13 polypeptide comprising the amino acid sequence of SEQ ID NO: 2. In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein, e.g., at least 50% of the wildtype reference protein. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of wildtype, e.g. 110%, 125%, 150%, 175%, 200%, 500%, 1000% or more.

One method of identifying amino acid residues which can be substituted is to align, for example, the human polypeptide to a homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. The variant amino acid or DNA sequence can be at least 90%, at least 95%, at least 96%, at least 97%, at least 98%, at least 99%, or more, identical to a native or reference sequence, e.g. SEQ ID NO: 2 or a nucleic acid encoding that amino acid sequence. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp (available on the world wide web at http://blast.ncbi.nlm.nih.gov), with default parameters set.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gin and Asn). Other such conservative substitutions, e.g., substitutions of entire regions having similar hydrophobicity characteristics, are known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure. Typically conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments, a polypeptide, e.g., an ADAMTS13 polypeptide, administered to a subject can comprise one or more amino acid substitutions or modifications. In some embodiments, the substitutions and/or modifications can prevent or reduce proteolytic degradation and/or prolong half-life of the polypeptide in the subject. In some embodiments, a polypeptide can be modified by conjugating or fusing it to other polypeptide or polypeptide domains such as, by way of non-limiting example, transferrin (WO006096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a polypeptide, e.g., an ADAMTS13 polypeptide, as described herein can comprise at least one peptide bond replacement. A single peptide bond or multiple peptide bonds, e.g. 2 bonds, 3 bonds, 4 bonds, 5 bonds, or 6 or more bonds, or all the peptide bonds can be replaced. An isolated peptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, a polypeptide, e.g., an ADAMTS13 polypeptide, as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, an ADAMTS13 polypeptide as described herein can comprise alternative amino acids. Non-limiting examples of alternative amino acids include D-amino acids, beta-amino acids, homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, a polypeptide, e.g. an ADAMTS13 polypeptide, can be modified, e.g. by addition of a moiety to one or more of the amino acids comprising the peptide. In some embodiments, a polypeptide as described herein can comprise one or more moiety molecules, e.g. 1 or more moiety molecules per peptide, 2 or more moiety molecules per peptide, 5 or more moiety molecules per peptide, 10 or more moiety molecules per peptide or more moiety molecules per peptide. In some embodiments, a polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties. The half-life of a polypeptide can be increased by the addition of moieties, e.g. PEG or albumin.

In some embodiments, the polypeptide administered to the subject (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. In some embodiments, a polypeptide as described herein can be chemically synthesized and mutations can be incorporated as part of the chemical synthesis process.

In some embodiments, a polypeptide, e.g., an ADAMTS13 polypeptide, as described herein can be formulated as a pharmaceutically acceptable prodrug. As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* II, 345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J Pharm. Sci.* 4: 49-59 (1996); Gangwar et al., "Pro-drug, molecular structure and percutaneous delivery", *Des. Biopharm. Prop. Prodrugs Analogs*, [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al.

"Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.,* 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), which are incorporated by reference herein in their entireties.

In some embodiments, a polypeptide as described herein can be a pharmaceutically acceptable solvate. The term "solvate" refers to a peptide as described herein in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The peptides of the present invention can be synthesized by using well known methods including recombinant methods and chemical synthesis. Recombinant methods of producing a peptide through the introduction of a vector including nucleic acid encoding the peptide into a suitable host cell is well known in the art, such as is described in Sambrook et al., Molecular Cloning: A Laboratory Manual, 2d Ed, Vols 1 to 8, Cold Spring Harbor, N.Y. (1989); M. W. Pennington and B. M. Dunn, Methods in Molecular Biology: Peptide Synthesis Protocols, Vol 35, Humana Press, Totawa, N.J. (1994), contents of both of which are herein incorporated by reference. Peptides can also be chemically synthesized using methods well known in the art. See for example, Merrifield et al., J. Am. Chem. Soc. 85:2149 (1964); Bodanszky, M., Principles of Peptide Synthesis, Springer-Verlag, New York, N.Y. (1984); Kimmerlin, T. and Seebach, D. J. Pept. Res. 65:229-260 (2005); Nilsson et al., Annu. Rev. Biophys. Biomol. Struct. (2005) 34:91-118; W. C. Chan and P. D. White (Eds.) Fmoc Solid Phase Peptide Synthesis: A Practical Approach, Oxford University Press, Cary, N.C. (2000); N. L. Benoiton, Chemistry of Peptide Synthesis, CRC Press, Boca Raton, Fla. (2005); J. Jones, Amino Acid and Peptide Synthesis, $2^{nd}$ Ed, Oxford University Press, Cary, N.C. (2002); and P. Lloyd-Williams, F. Albericio, and E. Giralt, Chemical Approaches to the synthesis of peptides and proteins, CRC Press, Boca Raton, Fla. (1997), contents of all of which are herein incorporated by reference. Peptide derivatives can also be prepared as described in U.S. Pat. Nos. 4,612,302; 4,853,371; and 4,684,620, and U.S. Pat. App. Pub. No. 2009/0263843, contents of all which are herein incorporated by reference.

In some embodiments, the technology described herein relates to a nucleic acid encoding a polypeptide (e.g. an ADAMTS13 polypeptide) as described herein. As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the nucleic acid is DNA. In another aspect, the nucleic acid is RNA. Suitable nucleic acid molecules are DNA, including genomic DNA or cDNA. Other suitable nucleic acid molecules are RNA, including mRNA. The nucleic acid molecule can be naturally occurring, as in genomic DNA, or it may be synthetic, i.e., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

In some embodiments, a nucleic acid encoding a polypeptide as described herein (e.g. an ADAMTS13 polypeptide) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding encoding a polypeptide as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In some embodiments, an inhibitor of a given polypeptide can be an antibody reagent specific for that polypeptide. As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to e.g., vWf.

As used herein, "expression level" refers to the number of mRNA molecules and/or polypeptide molecules encoded by a given gene that are present in a cell or sample. Expression levels can be increased or decreased relative to a reference level.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. thrombotic microangiopathy. The term "treating" includes reducing or alleviating at least one adverse effect or symptom of a condition, disease or disorder associated with a condition. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating or preventing thrombotic microangiopathy in a subject being treated with a VEGF inhibitor, the method comprising administering to the subject an agonist of ADAMTS13.
2. A method of treating or preventing thrombotic microangiopathy (TMA) in a subject in need of treatment therefor, the method comprising administering to the subject an agonist of ADAMTS13.
3. A method of treating or preventing preeclampsia or a complication thereof in a subject in need of treatment therefor, the method comprising administering to the subject an agonist of ADAMTS13;
   wherein the complication is selected from the group consisting of:
   TMA; eclampsia; and Hemolysis, Elevated Liver enzymes and Low Platelet count syndrome (HELLP).
4. The method of paragraph 3, wherein the subject has an elevated level of circulating soluble VEGF receptor 1 (soluble fms-like tyrosine kinase 1; sFlt-1).
5. A method of treating or preventing thrombotic microangiopathy in a subject in need of treatment for preeclampsia, the method comprising administering to the subject an agonist of ADAMTS13.
6. The method of any of paragraphs 1-5, wherein the subject has a condition selected from the group consisting of:
   Preeclampsia; VEGF-inhibitor associated TMA; TMA; thrombotic thrombocytic purpura (TPP); hemolytic uremic syndrome (HUS); HELLP syndrome; drug induced thrombotic microangiopathy; TMA induced by cyclosprorine or tacrolimus; solid organ transplant; infection; hypertension; and cancer.
7. A method of treating cancer, the method comprising administering to a subject in need of treatment for cancer:
   a VEGF inhibitor; and
   an agonist of ADAMTS13.
8. The method of paragraph 7, wherein the subject is a subject at risk or at increased risk of developing thrombotic microangiopathy.
9. A method of treating or preventing thrombotic microangiopathy in a subject in need of treatment for cancer, the method comprising administering to the subject:
   a VEGF inhibitor; and
   an agonist of ADAMTS13.
10. The method of any of paragraphs 1-9, wherein the VEGF inhibitor is selected from the group consisting of:
    bevacizumab; sunitinib; aflibercept; pazopanib; axitinib; sorafenib; vandetanib; regorafenib; and ramucirumab.
11. The method of any of paragraphs 1-10, wherein the agonist of ADAMTS13 is selected from the group consisting of:
    an ADAMTS13 polypeptide or functional fragment thereof; a recombinant ADAMTS13 polypeptide or functional fragment thereof; a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors.
12. The method of any of paragraphs 1-11, wherein the thrombotic microangiopathy is selected from the group consisting of:
    thrombotic thrombocytic purpura (TPP); hemolytic uremic syndrome (HUS); and Hemolysis, Elevated Liver enzymes and Low Platelet count syndrome (HELLP).
13. The method of any of paragraphs 1-12, wherein the thrombotic microangiopathy is thrombotic thrombocytic purpura (TPP).
14. The method of any of paragraphs 1-12, wherein the thrombotic microangiopathy is Hemolysis, Elevated Liver enzymes and Low Platelet count syndrome (HELLP).
15. The method of any of paragraphs 1-14, wherein the subject is a subject determined to have an elevated level of expression of soluble VEGF receptor 1 (soluble fms-like tyrosine kinase 1; sFlt-1).
16. The method of any of paragraphs 1-15, wherein the subject is a subject determined to have a reduced level of expression and/or activity of ADAMTS13.
17. A method of reducing blood pressure or treating or preventing renal damage in a subject in need thereof, the method comprising administering to the subject an agonist of ADAMTS13.
18. The method of paragraph 17, wherein the subject is a subject who is receiving or has received administration of a VEGF inhibitor.
19. The method of any of paragraphs 17-18, wherein the VEGF inhibitor is selected from the group consisting of:
    bevacizumab; sunitinib; aflibercept; pazopanib; axitinib; sorafenib vandetanib; regorafenib; and ramucirumab.

20. The method of any of paragraphs 17-19, wherein the subject has a condition selected from the group consisting of:
Preeclampsia; VEGF-inhibitor associated TMA; TMA; thrombotic thrombocytic purpura (TPP); hemolytic uremic syndrome (HUS); Hemolysis, Elevated Liver enzymes and Low Platelet count syndrome (HELLP); drug induced thrombotic microangiopathy (e.g., TMA induced by cyclosprorine or tacrolimus); solid organ transplant; infection; hypertension; and cancer.

21. The method of any of paragraphs 17-20, wherein the agonist of ADAMTS13 is selected from the group consisting of:
an ADAMTS13 polypeptide or functional fragment thereof; a recombinant ADAMTS13 polypeptide or functional fragment thereof; a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors.

22. The method of any of paragraphs 17-21, wherein the subject is a subject determined to have an elevated level of expression of soluble VEGF receptor 1 (soluble fms-like tyrosine kinase 1; sFlt-1).

23. The method of any of paragraphs 17-22, wherein the subject is a subject determined to have a reduced level of expression and/or activity of ADAMTS13.

24. An assay comprising:
measuring the level of expression or activity of ADAMTS13 in a test sample obtained from a subject;
wherein a decrease in the level relative to a reference level indicates the subject has a higher risk of having or developing thrombotic microangiopathy (TMA).

25. A method of identifying a subject in need of treatment for thrombotic microangiopathy (TMA), the method comprising:
measuring the level or activity of ADAMTS13 in a test sample obtained from a subject; and
identifying the subject as being in need of treatment for thrombotic microangiopathy (TMA) when the level of ADAMTS13 is decreased relative to a reference level.

26. A method of determining if a subject is at risk for thrombotic microangiopathy (TMA), the method comprising:
measuring the level or activity of ADAMTS13 in a test sample obtained from a subject; comparing the level of level or activity of ADAMTS13 in the sample to a reference level;
determining that the subject is at risk for thrombotic microangiopathy (TMA) when the level is decreased relative to a reference level; and
determining that the subject is not at risk for thrombotic microangiopathy (TMA) when the level is not decreased relative to a reference level.

27. A method of determining the efficacy of a treatment for thrombotic microangiopathy (TMA), the method comprising:
(a) measuring the level or activity of ADAMTS13 in a test sample obtained from a subject before administration of the treatment;
(b) measuring the level or activity of ADAMTS13 in a test sample obtained from a subject after administration of the treatment;
(c) determining that the treatment is efficacious when the level determined in step (b) is not decreased relative to the level determined in step (a); and
(d) determining that the treatment is not efficacious when the level determined in step (b) is decreased relative to the level determined in step (a).

28. A method of treatment for thrombotic microangiopathy (TMA) comprising;
measuring the level or activity of ADAMTS13 in a test sample obtained from a subject; and treating the subject for TMA when the level is decreased relative to a reference level.

29. A method of treatment for thrombotic microangiopathy (TMA) comprising;
administering a treatment for TMA to a subject determined to have a level or activity of ADAMTS13 which is decreased relative to a reference level.

30. The method of any of paragraphs 24-29, wherein the treatment comprises a treatment selected from the group consisting of:
An agonist of ADAMTS13; an ADAMTS13 polypeptide or functional fragment thereof; a recombinant ADAMTS13 polypeptide or functional fragment thereof; a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors.

31. The assay or method of any of paragraphs 24-30, wherein the thrombotic microangiopathy is selected from the group consisting of:
thrombotic thrombocytic purpura (TPP); hemolytic uremic syndrome (HUS); and
Hemolysis, Elevated Liver enzymes and Low Platelet count syndrome (HELLP).

32. The assay or method of any of paragraphs 24-31, wherein the subject is a subject who is receiving or has received administration of a VEGF inhibitor.

33. The method of paragraph 32, wherein the VEGF inhibitor is selected from the group consisting of:
bevacizumab; sunitinib; aflibercept; pazopanib; axitinib; sorafenib; vandetanib; regorafenib; and ramucirumab.

34. The assay or method of any of paragraphs 24-33, wherein the subject has a condition selected from the group consisting of:
Preeclampsia; VEGF-inhibitor associated TMA; TMA; thrombotic thrombocytic purpura (TPP); hemolytic uremic syndrome (HUS); Hemolysis, Elevated Liver enzymes and Low Platelet count syndrome (HELLP); drug induced thrombotic microangiopathy (e.g., TMA induced by cyclosprorine or tacrolimus); solid organ transplant; infection; hypertension; and cancer.

35. The assay or method of any of paragraphs 24-34, wherein the subject is a subject determined to have an elevated level of expression of soluble VEGF receptor 1 (soluble fms-like tyrosine kinase 1; sFlt-1.

36. The assay or method of any of paragraphs 24-35, wherein the level of ADAMTS13 is determined by measuring the level of a nucleic acid.

37. The assay or method of paragraph 36, wherein the level of ADAMTS13 is determined by measuring the level of ADAMTS13 RNA transcript.
38. The assay or method of any of paragraphs 36-37, wherein the level of the nucleic acid is determined using a method selected from the group consisting of: RT-PCR; quantitative RT-PCR; Northern blot; microarray based expression analysis; next-generation sequencing; and RNA in situ hybridization.
39. The assay or method of any of paragraphs 24-38, wherein the level of ADAMTS13 is determined by measuring the level of ADAMTS13 polypeptide.
40. The assay or method of paragraph 39, wherein the polypeptide level is measured using immunochemistry.
41. The assay or method of paragraph 40, wherein the antibody reagent is detectably labeled or generates a detectable signal.
42. The assay or method of paragraph 39-41, wherein the level of the polypeptide is determined using a method selected from the group consisting of:
Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay.
43. The assay or method of any of paragraphs 24-42, wherein the expression level of ADAMTS13 is normalized relative to the expression level of one or more reference genes or reference proteins.
44. The assay or method of any of paragraphs 24-43, wherein the reference level of ADAMTS13 is the expression level of ADAMTS13 in a prior sample obtained from the subject.
45. The assay or method of any of paragraphs 24-44, wherein the activity or expression level of ADAMTS13 is determined to be reduced relative to a reference if an ADAMTS13 dampening mutation is detected in the sample.
46. The assay or method of paragraph 45, wherein the mutation is selected from the group consisting of:
c. 1308G>C; c.428T>C (p.Ile143Thr); c. 1709A>G (p.Tyr570Cys); C1213Y, W1245del; and K1256FS; pR1060W; pR193W; p.A250V; pR268S; p.C508Y; 9.I673F; p.C908Y; p.R1123C; p.Q449X; c.4143_4144insA; C.106_107delAG; p.P475S; p.P618A; p.Q448E; and p.R1336W
47. The assay or method of any of paragraphs 24-46, wherein the sample comprises blood; serum; urine; or plasma.
48. The assay or method of any of paragraphs 24-47, further comprising the step of administering to the subject a treatment selected from the group consisting of:
an agonist of ADAMTS13; an ADAMTS13 polypeptide or functional fragment thereof; a recombinant ADAMTS13 polypeptide or functional fragment thereof; a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors.

49. The use of an agonist of ADAMTS13 to reduced blood pressure treat renal damage in a subject in need thereof, the use comprising administering to the subject an agonist of ADAMTS13.
50. The use of paragraph 49, wherein the subject is a subject who is receiving or has received administration of a VEGF inhibitor.
51. The use of any of paragraphs 49-50, wherein the VEGF inhibitor is selected from the group consisting of:
bevacizumab; sunitinib; aflibercept; pazopanib; axitinib; sorafenib vandetanib; regorafenib; and ramucirumab.
52. The use of any of paragraphs 49-51, wherein the subject has a condition selected from the group consisting of:
Preeclampsia; VEGF-inhibitor associated TMA; TMA; thrombotic thrombocytic purpura (TPP); hemolytic uremic syndrome (HUS); Hemolysis, Elevated Liver enzymes and Low Platelet count syndrome (HELLP); drug induced thrombotic microangiopathy (e.g., TMA induced by cyclosprorine or tacrolimus); solid organ transplant; infection; hypertension; and cancer.
53. The use of any of paragraphs 49-52, wherein the agonist of ADAMTS13 is selected from the group consisting of:
an ADAMTS13 polypeptide or functional fragment thereof; a recombinant ADAMTS13 polypeptide or functional fragment thereof; a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors.
54. The use of any of paragraphs 49-53, wherein the subject is a subject determined to have an elevated level of expression of soluble VEGF receptor 1 (soluble fms-like tyrosine kinase 1; sFlt-1).
55. The use of any of paragraphs 49-54, wherein the subject is a subject determined to have a reduced level of expression and/or activity of ADAMTS13.
56. The use of an agonist of ADAMTS13 for treating or preventing thrombotic microangiopathy in a subject being treated with a VEGF inhibitor, the use comprising administering to the subject an agonist of ADAMTS13.
57. The use of an agonist of ADAMTS13 for treating or preventing thrombotic microangiopathy (TMA) in a subject in need of treatment therefor, the use comprising administering to the subject an agonist of ADAMTS13.
58. The use of an agonist of ADAMTS13 for treating or preventing preeclampsia or a complication thereof in a subject in need of treatment therefor, the use comprising administering to the subject an agonist of ADAMTS13;
wherein the complication is selected from the group consisting of:
TMA; eclampsia; and Hemolysis, Elevated Liver enzymes and Low Platelet count syndrome (HELLP).

59. The use of paragraph 58, wherein the subject has an elevated level of circulating soluble VEGF receptor 1 (soluble fms-like tyrosine kinase 1; sFlt-1).

60. The use of an agonist of ADAMTS13 for treating or preventing thrombotic microangiopathy in a subject in need of treatment for preeclampsia, the use comprising administering to the subject an agonist of ADAMTS13.

61. The use of any of paragraphs 56-60, wherein the subject has a condition selected from the group consisting of:
Preeclampsia; VEGF-inhibitor associated TMA; TMA; thrombotic thrombocytic purpura (TPP); hemolytic uremic syndrome (HUS); HELLP syndrome; drug induced thrombotic microangiopathy; TMA induced by cyclosprorine or tacrolimus; solid organ transplant; infection; hypertension; and cancer.

62. The use of an agonist of ADAMTS13 for treating cancer, the use comprising administering to a subject in need of treatment for cancer:
a VEGF inhibitor; and
an agonist of ADAMTS13.

63. The use of paragraph 62, wherein the subject is a subject at risk or at increased risk of developing thrombotic microangiopathy.

64. The use of an agonist of ADAMTS13 for treating or preventing thrombotic microangiopathy in a subject in need of treatment for cancer, the use comprising administering to the subject:
a VEGF inhibitor; and
an agonist of ADAMTS13.

65. The use of any of paragraphs 56-64, wherein the VEGF inhibitor is selected from the group consisting of:
bevacizumab; sunitinib; aflibercept; pazopanib; axitinib; sorafenib; vandetanib; regorafenib; and ramucirumab.

66. The use of any of paragraphs 56-65, wherein the agonist of ADAMTS13 is selected from the group consisting of:
an ADAMTS13 polypeptide or functional fragment thereof; a recombinant ADAMTS13 polypeptide or functional fragment thereof; a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors.

67. The use of any of paragraphs 56-66, wherein the thrombotic microangiopathy is selected from the group consisting of:
thrombotic thrombocytic purpura (TPP); hemolytic uremic syndrome (HUS); and Hemolysis, Elevated Liver enzymes and Low Platelet count syndrome (HELLP).

68. The use of any of paragraphs 56-67, wherein the thrombotic microangiopathy is thrombotic thrombocytic purpura (TPP).

69. The use of any of paragraphs 56-68, wherein the thrombotic microangiopathy is Hemolysis, Elevated Liver enzymes and Low Platelet count syndrome (HELLP).

70. The use of any of paragraphs 56-69, wherein the subject is a subject determined to have an elevated level of expression of soluble VEGF receptor 1 (soluble fms-like tyrosine kinase 1; sFlt-1).

71. The use of any of paragraphs 56-70, wherein the subject is a subject determined to have a reduced level of expression and/or activity of ADAMTS13.

Some embodiments of the technology described herein can be defined according to any of the following numbered paragraphs:

1. A method of treating or preventing thrombotic microangiopathy in a subject being treated with a VEGF inhibitor, the method comprising administering to the subject an agonist of ADAMTS13.

2. A method of treating or preventing thrombotic microangiopathy (TMA) in a subject in need of treatment therefor, the method comprising administering to the subject an agonist of ADAMTS13.

3. A method of treating or preventing preeclampsia or a complication thereof in a subject in need of treatment therefor, the method comprising administering to the subject an agonist of ADAMTS13;
wherein the complication is selected from the group consisting of:
TMA; eclampsia; and Hemolysis, Elevated Liver enzymes and Low Platelet count syndrome (HELLP).

4. The method of paragraph 3, wherein the subject has an elevated level of circulating soluble VEGF receptor 1 (soluble fms-like tyrosine kinase 1; sFlt-1).

5. A method of treating or preventing thrombotic microangiopathy in a subject in need of treatment for preeclampsia, the method comprising administering to the subject an agonist of ADAMTS13.

6. The method of any of paragraphs 1-5, wherein the subject has a condition selected from the group consisting of:
Preeclampsia; VEGF-inhibitor associated TMA; TMA; thrombotic thrombocytic purpura (TPP); hemolytic uremic syndrome (HUS); HELLP syndrome; drug induced thrombotic microangiopathy; TMA induced by cyclosprorine or tacrolimus; solid organ transplant; infection; hypertension; and cancer.

7. A method of treating cancer, the method comprising administering to a subject in need of treatment for cancer:
a VEGF inhibitor; and
an agonist of ADAMTS13.

8. The method of paragraph 7, wherein the subject is a subject at risk or at increased risk of developing thrombotic microangiopathy.

9. A method of treating or preventing thrombotic microangiopathy in a subject in need of treatment for cancer, the method comprising administering to the subject:
a VEGF inhibitor; and
an agonist of ADAMTS13.

10. The method of any of paragraphs 1-9, wherein the VEGF inhibitor is selected from the group consisting of:
bevacizumab; sunitinib; aflibercept; pazopanib; axitinib; sorafenib; vandetanib; regorafenib; and ramucirumab.

11. A method of treating intestinal inflammation in a subject in need thereof, the method comprising administering an agonist of ADAMTS13 to the subject.

12. The method of paragraph 11, wherein the intestinal inflammation is inflammatory bowel disease (IBD) or colitis.

13. The method of any of paragraphs 11-12, wherein the subject is a subject at risk or at increased risk of developing thrombosis.
14. The method of paragraph 13, wherein the thrombosis is deep vein thrombosis, pulmonary embolism, or an arterial thrombosis.
15. The method of any of paragraphs 1-14, wherein the agonist of ADAMTS13 is selected from the group consisting of:
    an ADAMTS13 polypeptide or functional fragment thereof; a recombinant ADAMTS13 polypeptide or functional fragment thereof; a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors.
16. The method of any of paragraphs 1-15, wherein the thrombotic microangiopathy is selected from the group consisting of:
    thrombotic thrombocytic purpura (TPP); hemolytic uremic syndrome (HUS); and
    Hemolysis, Elevated Liver enzymes and Low Platelet count syndrome (HELLP).
17. The method of any of paragraphs 1-16, wherein the thrombotic microangiopathy is thrombotic thrombocytic purpura (TPP).
18. The method of any of paragraphs 1-16, wherein the thrombotic microangiopathy is Hemolysis, Elevated Liver enzymes and Low Platelet count syndrome (HELLP).
19. The method of any of paragraphs 1-18, wherein the subject is a subject determined to have an elevated level of expression of soluble VEGF receptor 1 (soluble fms-like tyrosine kinase 1; sFlt-1).
20. The method of any of paragraphs 1-19, wherein the subject is a subject determined to have a reduced level of expression and/or activity of ADAMTS13.
21. A method of reducing blood pressure or treating or preventing renal damage in a subject in need thereof, the method comprising administering to the subject an agonist of ADAMTS13.
22. The method of paragraph 21, wherein the subject is a subject who is receiving or has received administration of a VEGF inhibitor.
23. The method of any of paragraphs 21-22, wherein the VEGF inhibitor is selected from the group consisting of:
    bevacizumab; sunitinib; aflibercept; pazopanib; axitinib; sorafenib vandetanib; regorafenib; and ramucirumab.
24. The method of any of paragraphs 21-23, wherein the subject has a condition selected from the group consisting of:
    Preeclampsia; VEGF-inhibitor associated TMA; TMA; thrombotic thrombocytic purpura (TPP); hemolytic uremic syndrome (HUS); Hemolysis, Elevated Liver enzymes and Low Platelet count syndrome (HELLP); drug induced thrombotic microangiopathy (e.g., TMA induced by cyclosprorine or tacrolimus); solid organ transplant; infection; hypertension; and cancer.
25. The method of any of paragraphs 21-24, wherein the agonist of ADAMTS13 is selected from the group consisting of:
    an ADAMTS13 polypeptide or functional fragment thereof; a recombinant ADAMTS13 polypeptide or functional fragment thereof; a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors.
26. The method of any of paragraphs 21-25, wherein the subject is a subject determined to have an elevated level of expression of soluble VEGF receptor 1 (soluble fms-like tyrosine kinase 1; sFlt-1).
27. The method of any of paragraphs 21-26, wherein the subject is a subject determined to have a reduced level of expression and/or activity of ADAMTS13.
28. A method of treating intestinal inflammation in a subject in need thereof, the method comprising administering an anticoagulant to a subject determined to have a reduced level of expression and/or activity of ADAMTS13.
29. The method of paragraph 28, wherein the intestinal inflammation is inflammatory bowel disease (IBD) or colitis.
30. The method of any of paragraphs 28-29, wherein the subject is a subject at risk or at increased risk of developing thrombosis.
31. The method of paragraph 30, wherein the thrombosis is deep vein thrombosis, pulmonary embolism, or an arterial thrombosis.
32. The method of any of paragraphs 28-31, wherein the subject is further administered an agonist of ADAMTS13.
33. An assay comprising:
    measuring the level of expression or activity of ADAMTS13 in a test sample obtained from a subject;
    wherein a decrease in the level relative to a reference level indicates the subject has a higher risk of having or developing thrombotic microangiopathy (TMA).
34. A method of identifying a subject in need of treatment for thrombotic microangiopathy (TMA), the method comprising:
    measuring the level or activity of ADAMTS13 in a test sample obtained from a subject; and
    identifying the subject as being in need of treatment for thrombotic microangiopathy (TMA) when the level of ADAMTS13 is decreased relative to a reference level.
35. A method of determining if a subject is at risk for thrombotic microangiopathy (TMA), the method comprising:
    measuring the level or activity of ADAMTS13 in a test sample obtained from a subject; comparing the level of level or activity of ADAMTS13 in the sample to a reference level;
    determining that the subject is at risk for thrombotic microangiopathy (TMA) when the level is decreased relative to a reference level; and
    determining that the subject is not at risk for thrombotic microangiopathy (TMA) when the level is not decreased relative to a reference level.

36. A method of determining the efficacy of a treatment for thrombotic microangiopathy (TMA), the method comprising:
   (a) measuring the level or activity of ADAMTS13 in a test sample obtained from a subject before administration of the treatment;
   (b) measuring the level or activity of ADAMTS13 in a test sample obtained from a subject after administration of the treatment;
   (c) determining that the treatment is efficacious when the level determined in step (b) is not decreased relative to the level determined in step (a); and
   (d) determining that the treatment is not efficacious when the level determined in step (b) is decreased relative to the level determined in step (a).

37. A method of treatment for thrombotic microangiopathy (TMA) comprising; measuring the level or activity of ADAMTS13 in a test sample obtained from a subject; and treating the subject for TMA when the level is decreased relative to a reference level.

38. A method of treatment for thrombotic microangiopathy (TMA) comprising;

39. administering a treatment for TMA to a subject determined to have a level or activity of ADAMTS13 which is decreased relative to a reference level. The method of any of paragraphs 33-38, wherein the treatment comprises a treatment selected from the group consisting of:
   An agonist of ADAMTS13; an ADAMTS13 polypeptide or functional fragment thereof; a recombinant ADAMTS13 polypeptide or functional fragment thereof; a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors.

40. The assay or method of any of paragraphs 33-39, wherein the thrombotic microangiopathy is selected from the group consisting of:
   thrombotic thrombocytic purpura (TPP); hemolytic uremic syndrome (HUS); and
   Hemolysis, Elevated Liver enzymes and Low Platelet count syndrome (HELLP).

41. The assay or method of any of paragraphs 33-40, wherein the subject is a subject who is receiving or has received administration of a VEGF inhibitor.

42. The method of paragraph 41, wherein the VEGF inhibitor is selected from the group consisting of:
   bevacizumab; sunitinib; aflibercept; pazopanib; axitinib; sorafenib; vandetanib; regorafenib; and ramucirumab.

43. The assay or method of any of paragraphs 33-42, wherein the subject has a condition selected from the group consisting of:
   Preeclampsia; VEGF-inhibitor associated TMA; TMA; thrombotic thrombocytic purpura (TPP); hemolytic uremic syndrome (HUS); Hemolysis, Elevated Liver enzymes and Low Platelet count syndrome (HELLP); drug induced thrombotic microangiopathy (e.g., TMA induced by cyclosprorine or tacrolimus); solid organ transplant; infection; hypertension; and cancer.

44. The assay or method of any of paragraphs 33-43, wherein the subject is a subject determined to have an elevated level of expression of soluble VEGF receptor 1 (soluble fms-like tyrosine kinase 1; sFlt-1.

45. The assay or method of any of paragraphs 1-44, wherein the level of ADAMTS13 is determined by measuring the level of a nucleic acid.

46. The assay or method of paragraph 45, wherein the level of ADAMTS13 is determined by measuring the level of ADAMTS13 RNA transcript.

47. The assay or method of any of paragraphs 45-46, wherein the level of the nucleic acid is determined using a method selected from the group consisting of: RT-PCR; quantitative RT-PCR; Northern blot; microarray based expression analysis; next-generation sequencing; and RNA in situ hybridization.

48. The assay or method of any of paragraphs 1-47, wherein the level of ADAMTS13 is determined by measuring the level of ADAMTS13 polypeptide.

49. The assay or method of paragraph 48, wherein the polypeptide level is measured using immunochemistry.

50. The assay or method of paragraph 49, wherein the antibody reagent is detectably labeled or generates a detectable signal.

51. The assay or method of paragraph 48-50, wherein the level of the polypeptide is determined using a method selected from the group consisting of:
   Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay.

52. The assay or method of any of paragraphs 1-51, wherein the expression level of ADAMTS13 is normalized relative to the expression level of one or more reference genes or reference proteins.

53. The assay or method of any of paragraphs 1-52, wherein the reference level of ADAMTS13 is the expression level of ADAMTS13 in a prior sample obtained from the subject.

54. The assay or method of any of paragraphs 1-53, wherein the activity or expression level of ADAMTS13 is determined to be reduced relative to a reference if an ADAMTS13 dampening mutation is detected in the sample.

55. The assay or method of paragraph 54 wherein the mutation is selected from the group consisting of:
   c. 1308G>C; c.428T>C (p.Ile143Thr); c. 1709A>G (p.Tyr570Cys); C1213Y, W1245del; and K1256FS; pR1060W; pR193W; p.A250V; pR268S; p.C508Y; 9.I673F; p.C908Y; p.R1123C; p.Q449X; c.4143_4144insA; C.106_107delAG; p.P475S; p.P618A; p.Q448E; and p.R1336W 56. The assay or method of any of paragraphs 1-55, wherein the sample comprises blood; serum; urine; or plasma.

57. The assay or method of any of paragraphs 1-56, further comprising the step of administering to the subject a treatment selected from the group consisting of:
   an agonist of ADAMTS13; an ADAMTS13 polypeptide or functional fragment thereof; a recombinant ADAMTS13 polypeptide or functional fragment thereof; a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors.

58. The use of an agonist of ADAMTS13 to reduce blood pressure treat renal damage in a subject in need thereof, the use comprising administering to the subject an agonist of ADAMTS13.

59. The use of paragraph 49, wherein the subject is a subject who is receiving or has received administration of a VEGF inhibitor.

60. The use of any of paragraphs 49-50, wherein the VEGF inhibitor is selected from the group consisting of:
bevacizumab; sunitinib; aflibercept; pazopanib; axitinib; sorafenib vandetanib; regorafenib; and ramucirumab.

61. The use of any of paragraphs 49-51, wherein the subject has a condition selected from the group consisting of:
Preeclampsia; VEGF-inhibitor associated TMA; TMA; thrombotic thrombocytic purpura (TPP); hemolytic uremic syndrome (HUS); Hemolysis, Elevated Liver enzymes and Low Platelet count syndrome (HELLP); drug induced thrombotic microangiopathy (e.g., TMA induced by cyclosprorine or tacrolimus); solid organ transplant; infection; hypertension; and cancer.

62. The use of an agonist of ADAMTS13 to treat intestinal inflammation, the use comprising administering the agonist of ADAMTS13 to a subject in need thereof.

63. The use of paragraph 62, wherein the intestinal inflammation is inflammatory bowel disease (IBD) or colitis.

64. The use of any of paragraphs 62-63, wherein the subject is a subject at risk or at increased risk of developing thrombosis.

65. The method of paragraph 64, wherein the thrombosis is deep vein thrombosis, pulmonary embolism, or an arterial thrombosis 66. The use of any of paragraphs 58-65, wherein the agonist of ADAMTS13 is selected from the group consisting of:
an ADAMTS13 polypeptide or functional fragment thereof; a recombinant ADAMTS13 polypeptide or functional fragment thereof; a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors.

67. The use of any of paragraphs 58-66, wherein the subject is a subject determined to have an elevated level of expression of soluble VEGF receptor 1 (soluble fms-like tyrosine kinase 1; sFlt-1).

68. The use of any of paragraphs 58-67, wherein the subject is a subject determined to have a reduced level of expression and/or activity of ADAMTS13.

69. The use of an agonist of ADAMTS13 for treating or preventing thrombotic microangiopathy in a subject being treated with a VEGF inhibitor, the use comprising administering to the subject an agonist of ADAMTS13.

70. The use of an agonist of ADAMTS13 for treating or preventing thrombotic microangiopathy (TMA) in a subject in need of treatment therefor, the use comprising administering to the subject an agonist of ADAMTS13.

71. The use of an agonist of ADAMTS13 for treating or preventing preeclampsia or a complication thereof in a subject in need of treatment therefor, the use comprising administering to the subject an agonist of ADAMTS13;
wherein the complication is selected from the group consisting of:
TMA; eclampsia; and Hemolysis, Elevated Liver enzymes and Low Platelet count syndrome (HELLP).

72. The use of paragraph 71, wherein the subject has an elevated level of circulating soluble VEGF receptor 1 (soluble fms-like tyrosine kinase 1; sFlt-1).

73. The use of an agonist of ADAMTS13 for treating or preventing thrombotic microangiopathy in a subject in need of treatment for preeclampsia, the use comprising administering to the subject an agonist of ADAMTS13.

74. The use of any of paragraphs 69-73, wherein the subject has a condition selected from the group consisting of:
Preeclampsia; VEGF-inhibitor associated TMA; TMA; thrombotic thrombocytic purpura (TPP); hemolytic uremic syndrome (HUS); HELLP syndrome; drug induced thrombotic microangiopathy; TMA induced by cyclosprorine or tacrolimus; solid organ transplant; infection; hypertension; and cancer.

75. The use of an agonist of ADAMTS13 for treating cancer, the use comprising administering to a subject in need of treatment for cancer:
a VEGF inhibitor; and
an agonist of ADAMTS13.

76. The use of paragraph 75, wherein the subject is a subject at risk or at increased risk of developing thrombotic microangiopathy.

77. The use of an agonist of ADAMTS13 for treating or preventing thrombotic microangiopathy in a subject in need of treatment for cancer, the use comprising administering to the subject:
a VEGF inhibitor; and
an agonist of ADAMTS13.

78. The use of any of paragraphs 69-77, wherein the VEGF inhibitor is selected from the group consisting of:
bevacizumab; sunitinib; aflibercept; pazopanib; axitinib; sorafenib; vandetanib; regorafenib; and ramucirumab.

79. The use of any of paragraphs 69-78, wherein the agonist of ADAMTS13 is selected from the group consisting of:
an ADAMTS13 polypeptide or functional fragment thereof; a recombinant ADAMTS13 polypeptide or functional fragment thereof; a nucleic acid encoding an ADAMTS13 polypeptide or functional fragment thereof; an antibody reagent that targets the A1 domain of von Willebrand factor (VWF); an aptamer that targets the A1 domain of von Willebrand factor (VWF); N-acetylcyteine (NAC): GPIβα-Ig chimera; functional fragments of GPIβα and/or mimetics thereof; and Weibel-Palade body secretion inhibitors.

80. The use of any of paragraphs 69-79, wherein the thrombotic microangiopathy is selected from the group consisting of:
   thrombotic thrombocytic purpura (TPP); hemolytic uremic syndrome (HUS); and Hemolysis, Elevated Liver enzymes and Low Platelet count syndrome (HELLP).
81. The use of any of paragraphs 69-80, wherein the thrombotic microangiopathy is thrombotic thrombocytic purpura (TPP).
82. The use of any of paragraphs 69-81, wherein the thrombotic microangiopathy is Hemolysis, Elevated Liver enzymes and Low Platelet count syndrome (HELLP).
83. The use of any of paragraphs 69-82, wherein the subject is a subject determined to have an elevated level of expression of soluble VEGF receptor 1 (soluble fms-like tyrosine kinase 1; sFlt-1).
84. The use of any of paragraphs 69-83, wherein the subject is a subject determined to have a reduced level of expression and/or activity of ADAMTS13.

EXAMPLES

Example 1: ADAMTS13 Protects Against Thrombotic Microangiopathy in Mice Receiving VEGF Inhibitor Thrombotic microangiopathy (TMA) is a life-threatening condition that affects some, but not all, recipients of vascular endothelial growth factor (VEGF) inhibitors given as part of cancer therapy. TMA is also a complication of preeclampsia, a disease characterized by excess production of the VEGF-scavenging soluble VEGF receptor 1 (soluble fms-like tyrosine kinase 1; sFlt-1). Risk factors for VEGF inhibitor-related TMA remain unknown. Described herein is the exploration of the hypothesis that deficiency of the VWF-cleaving enzyme ADAMTS13 contributes to the development of VEGF inhibitor-related TMA. ADAMTS13-/- mice overexpressing sFlt-1 presented all hallmarks of TMA, including thrombocytopenia, schistocytosis, anemia and VWF-positive microthrombi in multiple organs. Similar to VEGF inhibitor-related TMA in humans, these mice exhibited severely impaired kidney function and hypertension. In contrast, wild-type mice overexpressing sFlt-1 developed modest hypertension but no other features of TMA. Recombinant ADAMTS13 therapy ameliorated all symptoms of TMA in ADAMTS13-/- mice overexpressing sFlt-1 and normalized blood pressure in wild-type mice. ADAMTS13 activity may thus be a critical determinant for the development of TMA secondary to VEGF inhibition. Administration of recombinant ADAMTS13 can serve as a therapeutic approach to treat or prevent thrombotic complications of VEGF inhibition.

Thrombotic microangiopathies (TMAs) are a heterogeneous group of life-threatening disorders characterized by thrombocytopenia, schistocytosis, hemolytic anemia, microvascular thrombosis and end-organ damage affecting the kidney and brain.[1] Among the major subtypes of TMAs are thombocytopenic purpura (TTP) and hemolytic uremic syndrome (HUS).[1] TMAs may also be pregnancy-related: either as a facet of preeclampsia, characterized by hypertension and proteinuria, or as part of the HELLP syndrome (Hemolysis, Elevated Liver enzymes and Low Platelet count).[2,3] HELLP syndrome is a severe complication of preeclampsia, occurring in 0.5% to 0.9% of all pregnancies. Acquired TMAs are also observed after solid organ transplants or are related to certain drugs, advanced malignancies, severe hypertension or infections.[2]

The pathological mechanisms underlying TMAs are diverse. Typical HUS is usually caused by an infection with shiga-like-toxin-producing bacteria.[1] TTP, on the other hand, is associated with a marked deficiency in the metalloprotease ADAMTS13 with under 5% of its normal activity.[5,6] This deficiency can be caused by a genetic defect in the ADAMTS13 gene (hereditary TTP) or by autoantibodies against the enzyme (acquired TTP).[7] In healthy individuals, ADAMTS13 is responsible for the cleavage of large multimers of VWF, which are released from endothelial Weibel-Palade bodies or from platelets upon stimulation.[8] ADAMTS13 deficiency leads to an accumulation of highly thrombogenic ultra-large VWF (UL-VWF) that serves as a nidus for pathological thrombus formation. Intriguingly, even patients with severe ADAMTS13 deficiency may remain asymptomatic for years, suggesting that a second hit is needed to provoke clinical manifestations.[6] Known triggers of TTP are cancer, infection, pregnancy and certain medications,[9] such as some antineoplastic therapies.[10] Both preeclampsia/HELLP syndrome and atypical HUS can be associated with a decrease in ADAMTS13 concentration or activity, implying a more general role of this enzyme in TMAs.[11,12] Chemotherapies that inhibit VEGF or VEGF signaling—e.g., bevacizumab,[13] sunitinib[14,15] and aflibercept[16]—have been shown to induce TMA.[10] While TMA is the most severe adverse consequence of anti-VEGF therapy, the spectrum of toxicities includes proteinuria and hypertension, issues that are believed to arise from renal microvascular injury.[13,14,17-20] To date, there are no reliable means to predict whether a patient is likely to develop TMA, apart from the observation that patients with previous kidney damage seem to be more susceptible to renal TMA.[17]

The search for TMA risk factors is of additional interest because preeclampsia—an obstetric complication affecting 1 in 20 pregnancies worldwide-represents a natural state that mimics iatrogenic VEGF inhibition in critical ways: (1) affected women develop high circulating concentrations of the endogenous anti-VEGF protein sFlt-1; (2) clinical manifestations range from proteinuria and hypertension to severe microthrombotic end-organ damage in ~1% of cases; and (3) excess sFlt-1 suffices to recapitulate these manifestations in otherwise healthy animals.[3,19,21,22] Finally, identifying a mechanistic and modifiable risk factor for VEGF-related TMA (iatrogenic or pregnancy-related) could lead to first-in-kind therapeutic options. We performed experiments in genetic mouse models to test whether ADAMTS13 links the anti-VEGF state to TMA.

Results sFlt-1 Overexpression Induces Thrombocytopenia and Schistocytosis in ADAMTS13-/- Mice.

To determine whether sFlt-1 overexpression can induce TMA in mice lacking ADAMTS13, ADAMTS13-/- mice were injected with Ad-sFlt-1. Overexpression of sFlt-1 has been widely used in both mice and rats as a model of preeclampsia, as high levels of sFlt-1 can induce the classic symptoms of hypertension and proteinuria in a dose-dependent manner in rodents.[21,23] Expression of sFlt-1 levels in the plasma reaches a maximum 7 days after injection of the Ad-sFlt-1 virus and subsequently sFlt-1 expression declines.[24,25] As controls, WT mice were treated with identical amounts of Ad-sFlt-1 as the ADAMTS13-/- Ad-sFlt-1 mice or ADAMTS13-/- received equivalent amounts of Ad-null virus. The mice were then monitored for pathological and clinical signs of TMA.

To exclude effects due to possible differences in the sFlt-1 expression levels in the ADAMTS13−/− mice as compared to WT mice, sFlt-1 levels were measured at day 7 and day 10 (Table 1). At both time points, sFlt-1 levels did not differ between WT and ADAMTS13−/− mice. To evaluate whether ADAMTS13 regulates sFlt-1 levels, endogenous sFlt-1 levels were measured in wild type mice and ADAMTS13−/− mice and no differences were found (0.442 ng/ml+/−0.059 SEM for the WT mice and 0.462+/−0.167 ng/ml for the ADAMTS13−/− mice; n=5 and 3, respectively, P=0.856).

Figure 6:
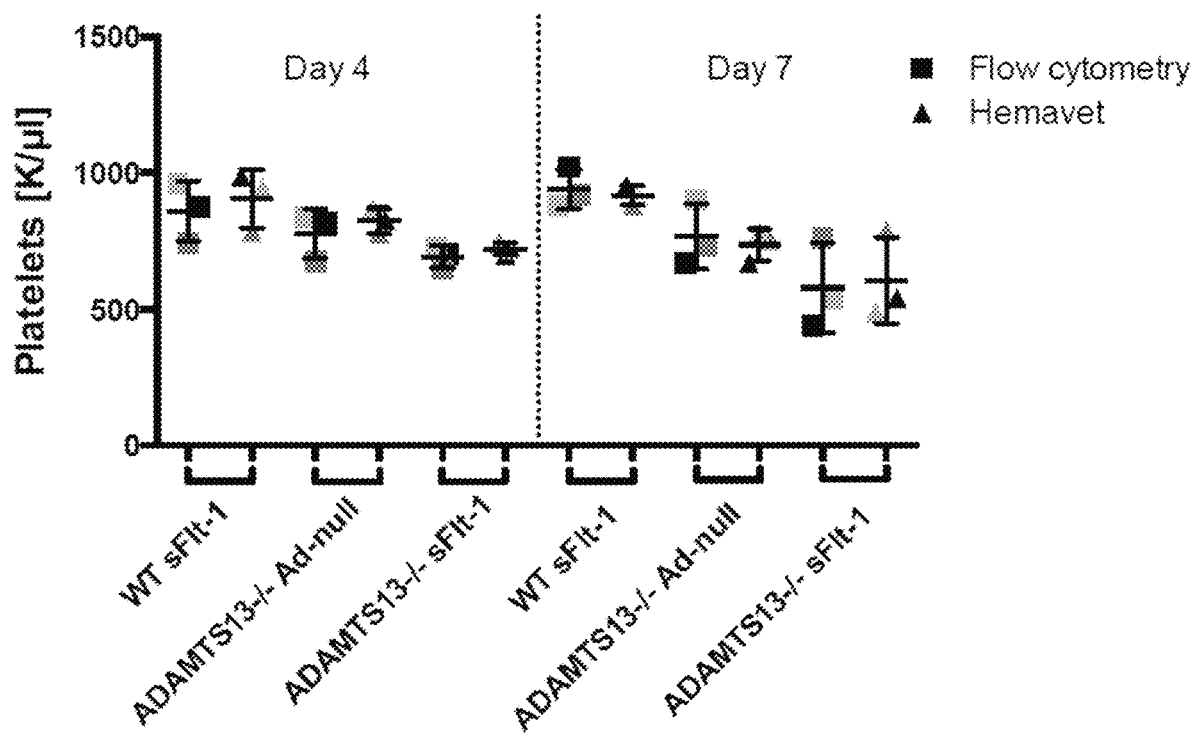
FIG. 6 demonstrates that the measurement of platelet counts by flow cytometry and hemavet shows very similar results. Platelet counts in WT and ADAMTS13−/− mice that had been injected with Ad-sFlt-1 or Ad-null were measured at day 4 and day 7. Platelet counts from the same mouse were determined either by flow cytometry (squares) or by hemavet (triangles), corresponding measurements for one treatment group are indicated by brackets underneath the x-axis. Within one treatment group individual mice are color-coded; n=3 for each treatment and time-point.

As one of the principal symptoms of TMAs is thrombocytopenia, platelet counts were analyzed on day 4, 7 and 10 (FIG. 1A). The Ad-sFlt-1 WT mice showed a minor but significant drop in platelet count on day 4 from which they recovered by day 7. The ADAMTS13−/− Ad-null mice had no significant alterations in their platelet counts throughout the observation period. On the other hand, ADAMTS13−/− Ad-sFlt-1 mice experienced a significant drop in platelet counts as early as day 4, which became even more pronounced by day 7. On day 10, platelet counts of ADAMTS13−/− Ad-sFlt-1 mice were no longer significantly different from untreated ADAMTS13−/− mice or the control groups. Alternative platelet measurements by flow cytometry were initially also used to exclude artifacts such as changes in platelet size that might lead to erroneous results in hemavet platelet count determination (FIG. 6).

Figure 1B:
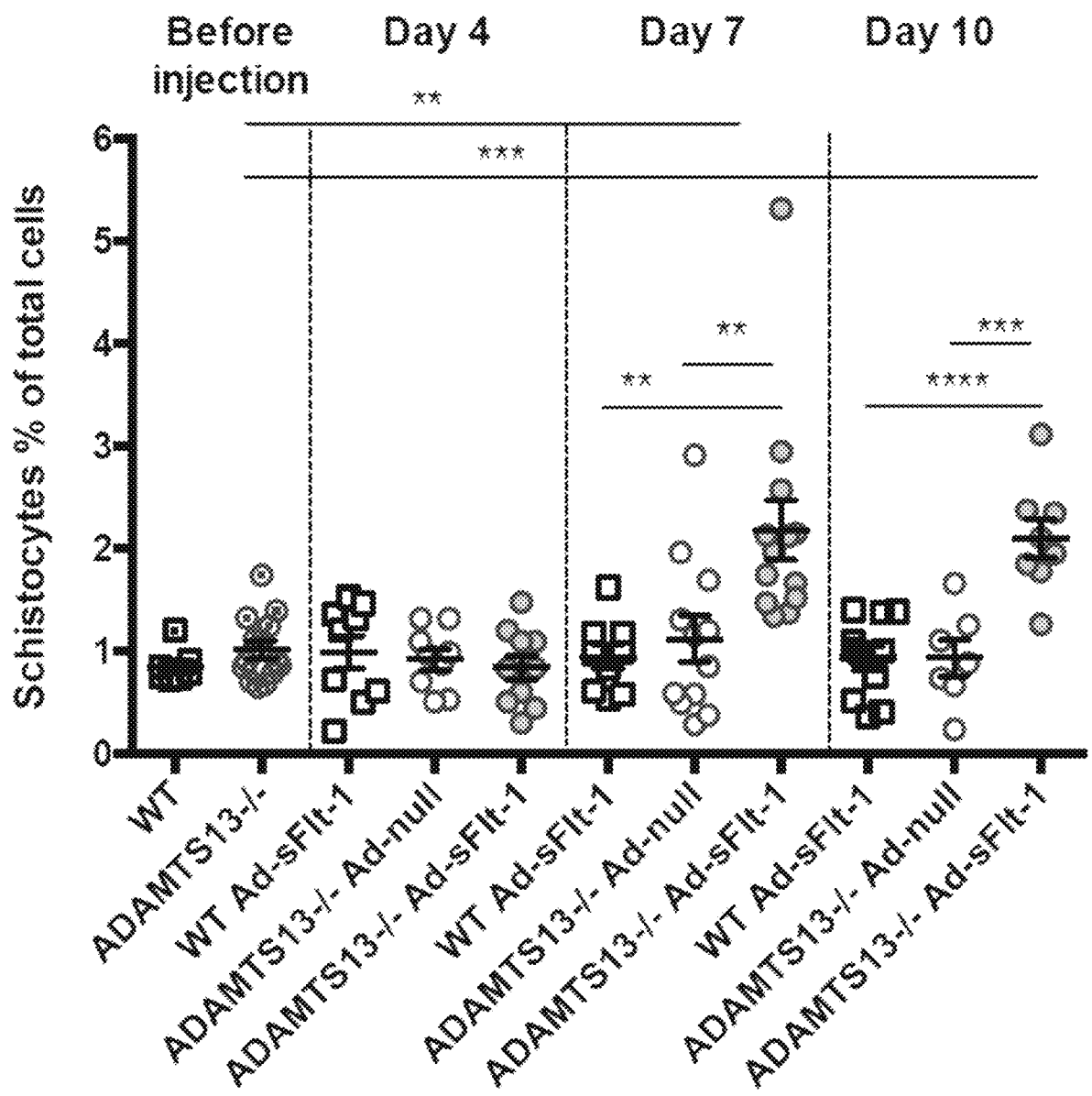
Figure 1C:
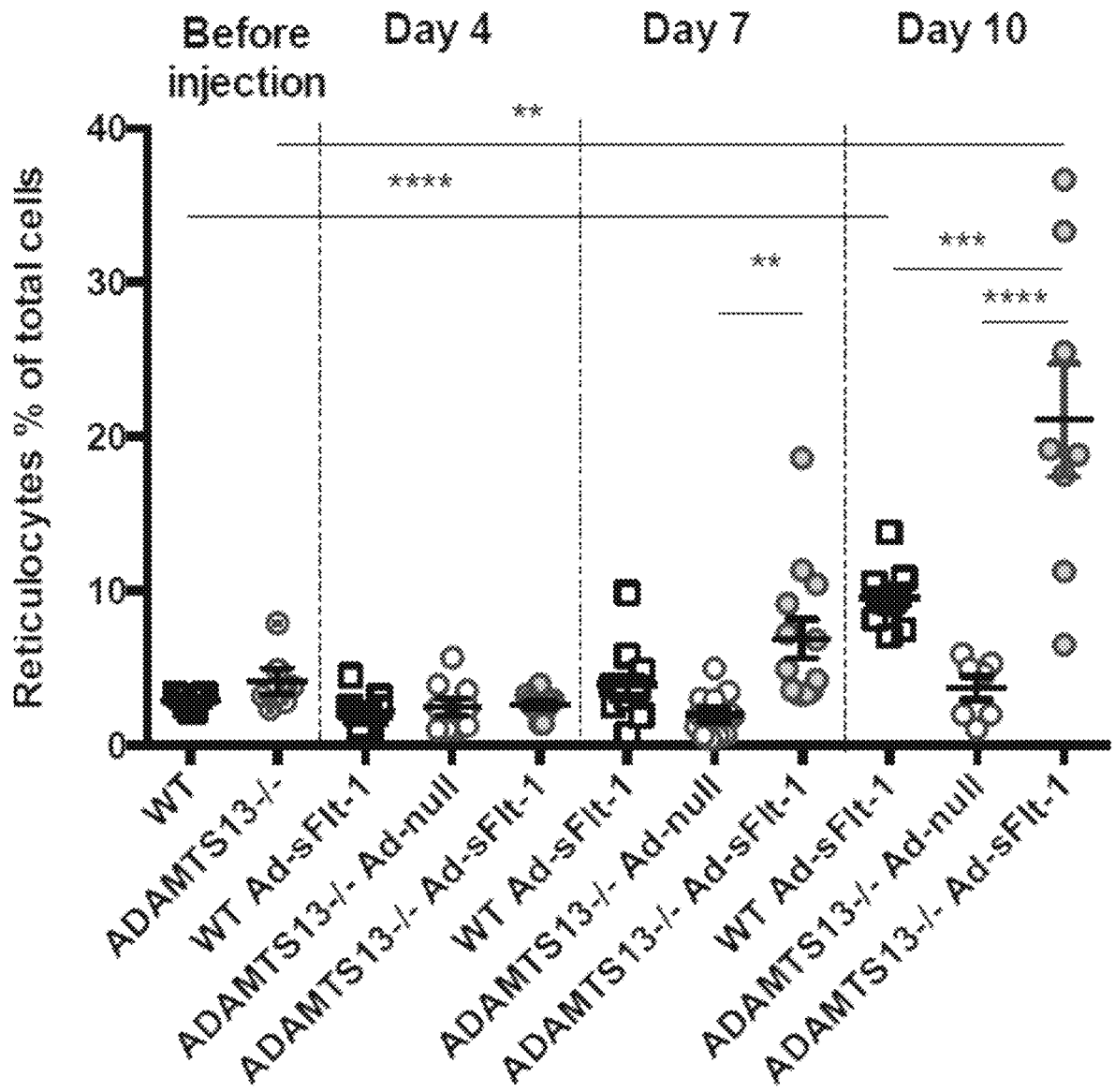
Figure 1D:
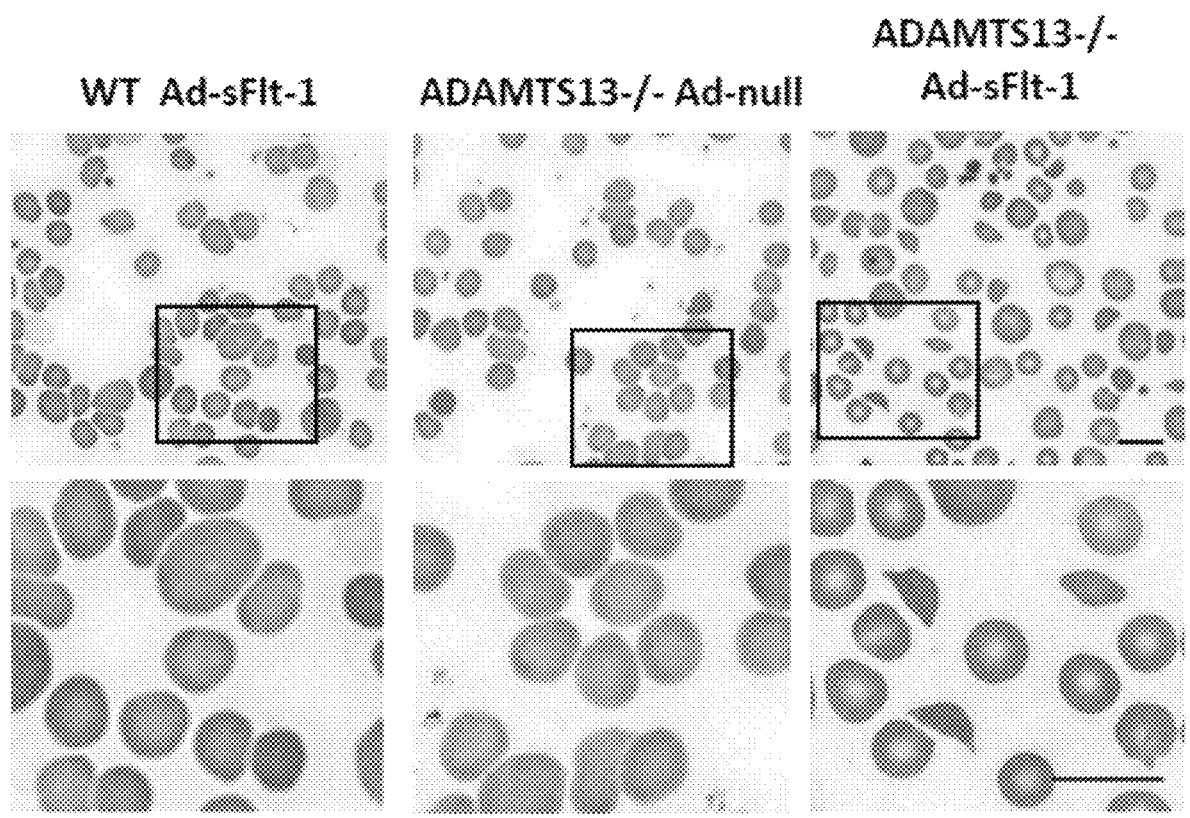

As pronounced thrombocytopenia noted with sFlt-1 overexpression in the absence of ADAMTS13 suggested an induction of TMA, the number of schistocytes in blood smears, an important characteristic of TMAs, was analyzed (FIG. 1B). At day 4, schistocyte counts did not differ from those of untreated mice in any group. However, by day 7, ADAMTS13−/− mice overexpressing sFlt-1 showed an almost 2-fold increase in schistocytes, together with anisocytosis (strong variation in the size of red blood cells) and polychromasia (variations in the staining behavior of erythrocytes; FIGS. 1B and 1D). Schistocytosis still persisted at day 10 in the ADAMTS13−/− Ad-sFlt-1 group. As a severe destruction of red blood cells would be expected to lead to a compensatory rise in reticulocyte counts, reticulocyte numbers were likewise assessed in the blood smears (FIGS. 1C and 1D). At day 7, reticulocyte counts started to increase in the ADAMTS13−/− Ad-sFlt-1 group and were significantly higher compared to the ADAMTS13−/− Ad-null mice. At day 10, this increase became even more pronounced. As the most severe destruction of red blood cells was observed on day 7 in the ADAMTS13−/− Ad-sFlt-1 mice, these results indicate a compensatory upregulation of red blood cell formation and thus reticulocytosis. Interestingly, WT Ad sFlt-1 mice also showed a notable increase in their reticulocyte counts by day 10, indicating that low-grade red blood cell destruction might also have been taking place in those mice, although schistocyte counts remained normal in the majority of the mice throughout the study. There were no major differences in phenotypes between untreated wild type mice and wild type mice receiving Ad-null therapy (Table 3).

Figure 1E:
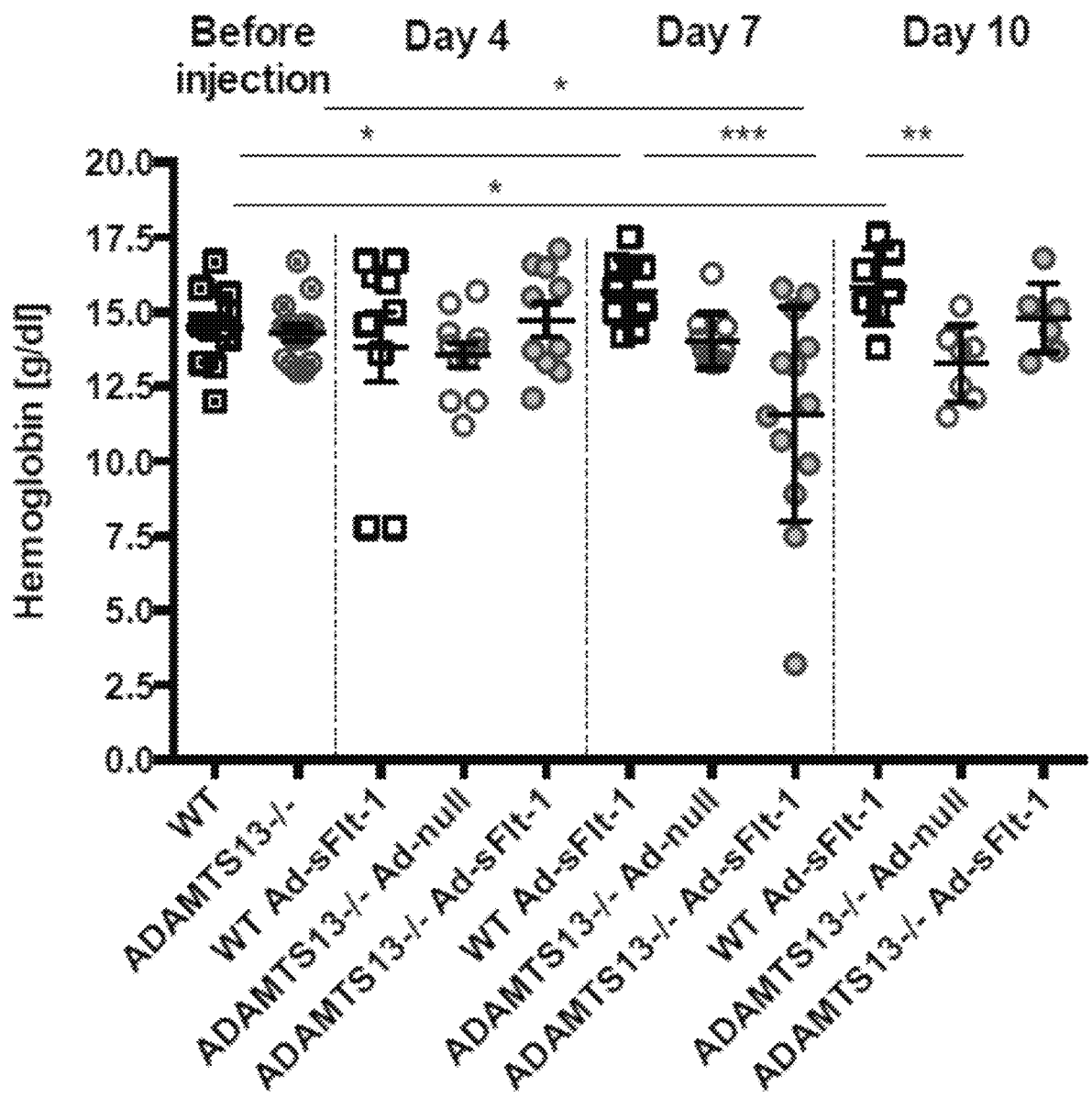

Patients suffering from TMA characteristically have hemolytic anemia, resulting from the severe destruction of red blood cells. Hemoglobin values were assessed as a measure for the severity of the resulting anemia (FIG. 1E). In the WT Ad-sFlt-1 mice, 2 mice were anemic by day 4, although overall hemoglobin was not significantly reduced at that time point. At day 7 and day 10, WT mice had slightly elevated levels of hemoglobin, in line with the previously proposed notion of a compensatory upregulation of erythrocyte production. In the ADAMTS13−/− mice, none of the Ad-null-treated mice, but 5 out of 13 ADAMTS13−/− Ad-sFlt-1 mice developed anemia with values <11 g/dl (hemoglobin 3.2-10.7 g/dl) by day 7. Average hemoglobin in the ADAMTS13−/− Ad-sFlt-1 was also significantly lower compared to untreated ADAMTS13−/− mice, corroborating the observation that development of TMA is strongly enhanced in ADAMTS13 deficiency.

sFlt-1 Causes VWF-Release and Leads to VWF-Rich Microthrombi in Numerous Organs of ADAMTS13−/− Mice.

Figure 1F:
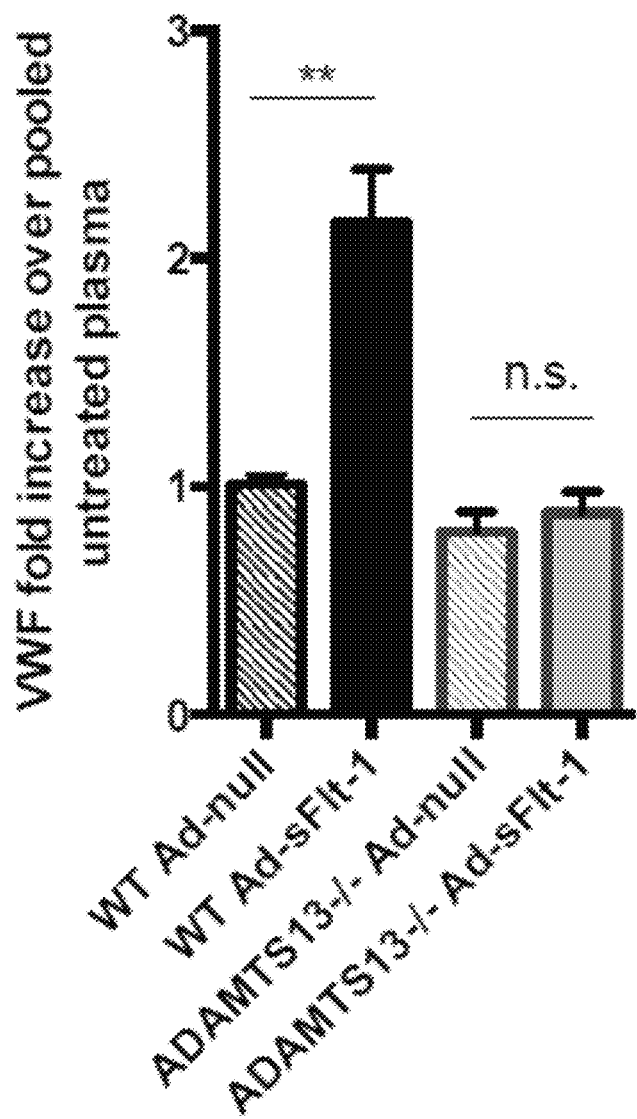
Figure 2:
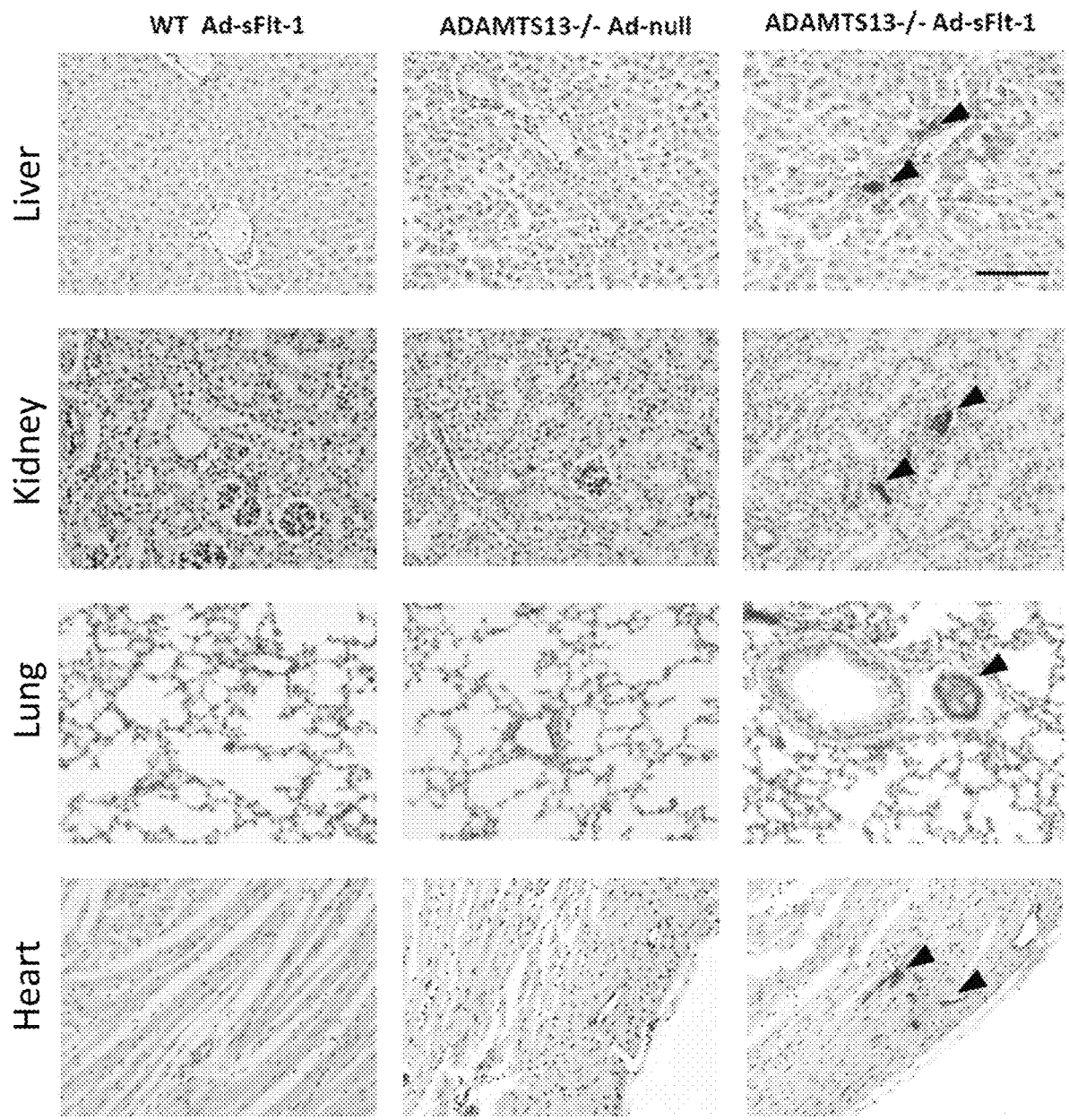
FIG. 2 demonstrates that ADAMTS13−/− mice show VWF-rich thrombi in multiple organs after sFlt-1 overexpression. Organs were collected from WT and ADAMTS13−/− mice 7 days after injection of Ad-sFlt-1 or Ad-null and immunohistochemical staining for VWF (brown) was performed. Representative photographs of liver, kidney, lung and heart sections are shown. Arrowheads indicate VWF-rich thrombi. Scale bar: 100 μm.
Figure 7:
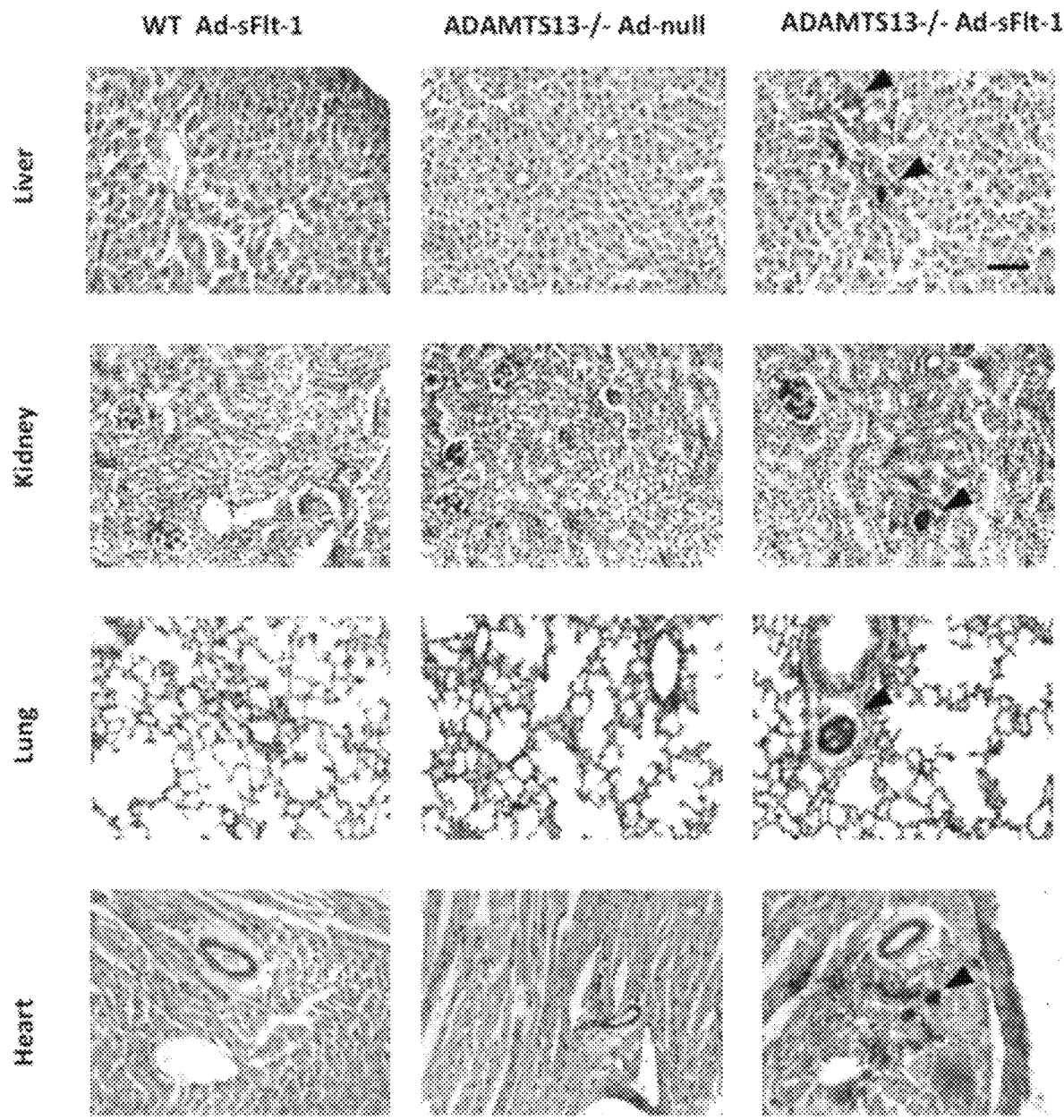
FIG. 7 demonstrates that VWF-rich thrombi in multiple organs after sFlt-1 overexpression in ADAMTS13−/− mice (lower power images). Organs were collected from WT and ADAMTS13−/− mice 7 days after injection of Ad-sFlt-1 or Ad-null. Representative photographs of immunohistochemical staining for VWF (brown) in liver, kidney, lung and heart sections are shown. Arrowheads indicate VWF-rich thrombi. Scale bar: 100 µm.

In TTP, schistocytes have been proposed to be a result of mechanical slicing of red blood cells by strands of VWF spanning across blood vessels.[7, 26] Because of the significant increase in schistocytes in the ADAMTS13−/− Ad-sFlt-1 mice, it was hypothesized that sFlt-1 leads to an increased release of stored VWF into blood. Plasma VWF in WT and ADAMTS13−/− mice, injected with Ad-null or Ad-sFlt-1, was measured (FIG. 1F). A strong increase was found in plasma VWF of the WT Ad-sFlt-1 mice. However, VWF levels were not elevated in the ADAMTS13−/− Ad-sFlt-1 mice (FIG. 1F). Without wishing to be bound by theory, a plausible explanation for this observation would be the consumption of the uncleaved VWF-strands into thrombi within the vasculature in the ADAMTS13−/− Ad-sFlt-1 mice, reflected by the thrombocytopenia seen in this group (FIG. 1A). Microthrombi are a pathological characteristic of TMAs and have been observed in murine models of TTP.[27, 28] For that reason, immunohistochemical staining was performed for VWF-rich thrombi in livers, kidneys, lungs and hearts of WT and ADAMTS13−/− mice treated with Ad-sFlt-1 and in Ad-null ADAMTS13−/− mice at day 7 after virus injection. VWF-positive thrombi could be found in all four organ groups in the ADAMTS13−/− mice that had received Ad-sFlt-1 (FIG. 2 and Table 2, FIG. 7) but were extremely rare in the control mice. Particularly the kidneys of ADAMTS13−/− Ad-sFlt-1 mice appeared to be very prone to microthrombosis, which is in line with the current knowledge of renal injury secondary to VEGF inhibitiors.[17]

ADAMTS13−/− Mice Overexpressing sFlt-1 are Susceptible to Proteinuria and Elevated Blood Pressure.

Figures 3A, 3B, 3C, 3D, 3E:
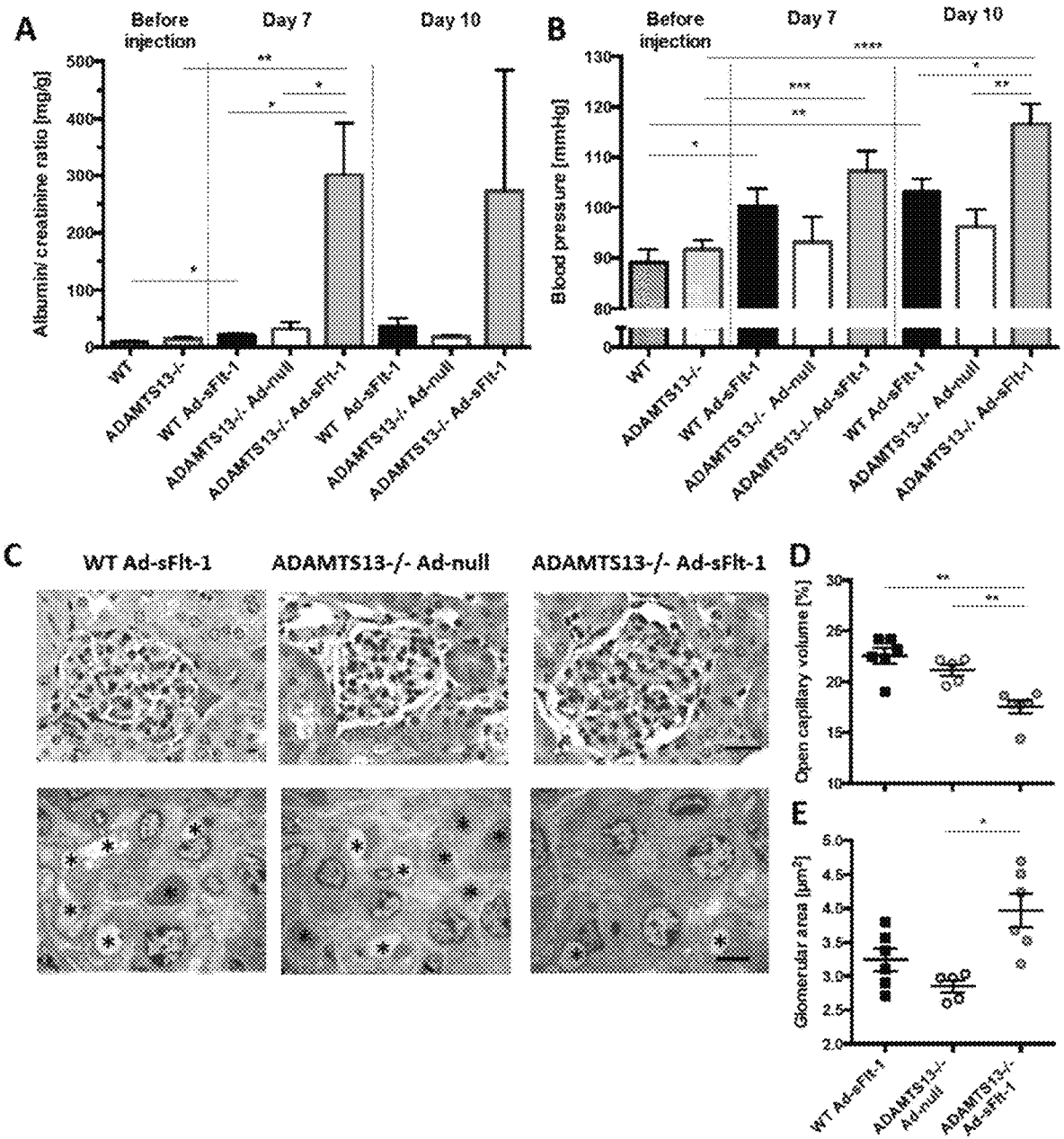
FIGS. 3A-3E demonstrate that ADAMTS13−/− mice are prone to proteinuria, hypertension and endotheliosis after Ad-sFlt-1 injection.

In patients treated with VEGF inhibitors, proteinuria and hypertension are common and by far the most prevalent side effect of the treatment.[13, 18] Similarly, preeclampsia is defined as new onset hypertension and proteinuria during pregnancy and both features are thought to originate at least in part from high levels of the VEGF-scavenger sFlt-1.[21] Therefore, it was next investigated whether lack of ADAMTS13 exacerbates the onset of these two prominent symptoms. Indeed, ADAMTS13−/− mice that had received Ad-sFlt-1 quickly developed pronounced proteinuria, determined as albumin/creatinine-ratio[21] (FIG. 3A). In spite of an overall low albumin-creatinine ratio, WT mice still showed a significant increase by day 7, from 9.3±3.67 mg/g to 16±7.9 mg/g, indicating that sFlt-1 induces modest proteinuria in mice with ADAMTS13.

To evaluate the influence of ADAMTS13 deficiency on the development of hypertension in mice overexpressing sFlt-1, systolic blood pressure was measured in a set of mice before virus injection, on day 7 and on day 10 (FIG. 3B). In line with the previous reports of blood pressure increase after sFlt-1 overexpression,[21, 29] the WT Ad-sFlt-1 mice showed a significant elevation in their blood pressure by day 7, which became more pronounced at day 10. ADAMTS13−/− mice that had received Ad-null virus did not show alterations in their blood pressure throughout the observation period. In contrast, in ADAMTS13−/− mice blood pressure increased by approximately 25 mmHg 10 days after Ad-sFlt-1 injection, a more substantial increase than that observed in the WT Ad-sFlt-1 mice. In conclusion, ADAMTS13−/− mice overexpressing sFlt-1 not only displayed pathophysiological parameters of TMA but also an exacerbation of clinical symptoms typical of some patients exposed to VEGF-inhibitors.[30]

ADAMTS13−/− Mice Injected with Ad-sFlt-1 are More Prone to Glomerular Endotheliosis than WT Mice.

Endothelial swelling, resulting in enlarged glomeruli, and capillary loop occlusion are histological indicators of kidney damage due to VEGF inhibition.[31] Therefore, H&E micrographs (FIG. 3C, upper panel) of kidneys from the WT Ad-sFlt-1, the ADAMTS13−/− Ad-null and the ADAMTS13−/− Ad-sFlt-1 mice were analyzed for percentage of open capillary volume (FIG. 3D) and average glomerular area (FIG. 3E). In the kidneys of ADAMTS13−/− Ad sFlt-1 mice the open capillary lumen was dramatically reduced and glomeruli enlarged, consistent with the strong proteinuria in these animals. Electron microscopy was performed to further evaluate glomerular structure (FIG. 3C, lower panel). It revealed swollen endothelial cells and obliterated capillary lumens in the ADAMTS13−/− Ad-sFlt-1 mice, while both WT sFlt-1 mice as well as ADAMTS13−/− Ad-null mice showed open capillary loops. WT Ad-sFlt-1 kidney tissue had modest endothelial damage, suggesting a certain amount of structural damage even without ADAMTS13-deficiency.

Treatment with rhADAMTS13 Rescues ADAMTS13−/− Ad-sFlt-1 Mice from the Development of TMA.

Figures 4A, 4B, 4C, 4D, 4E, 4F, 4G:
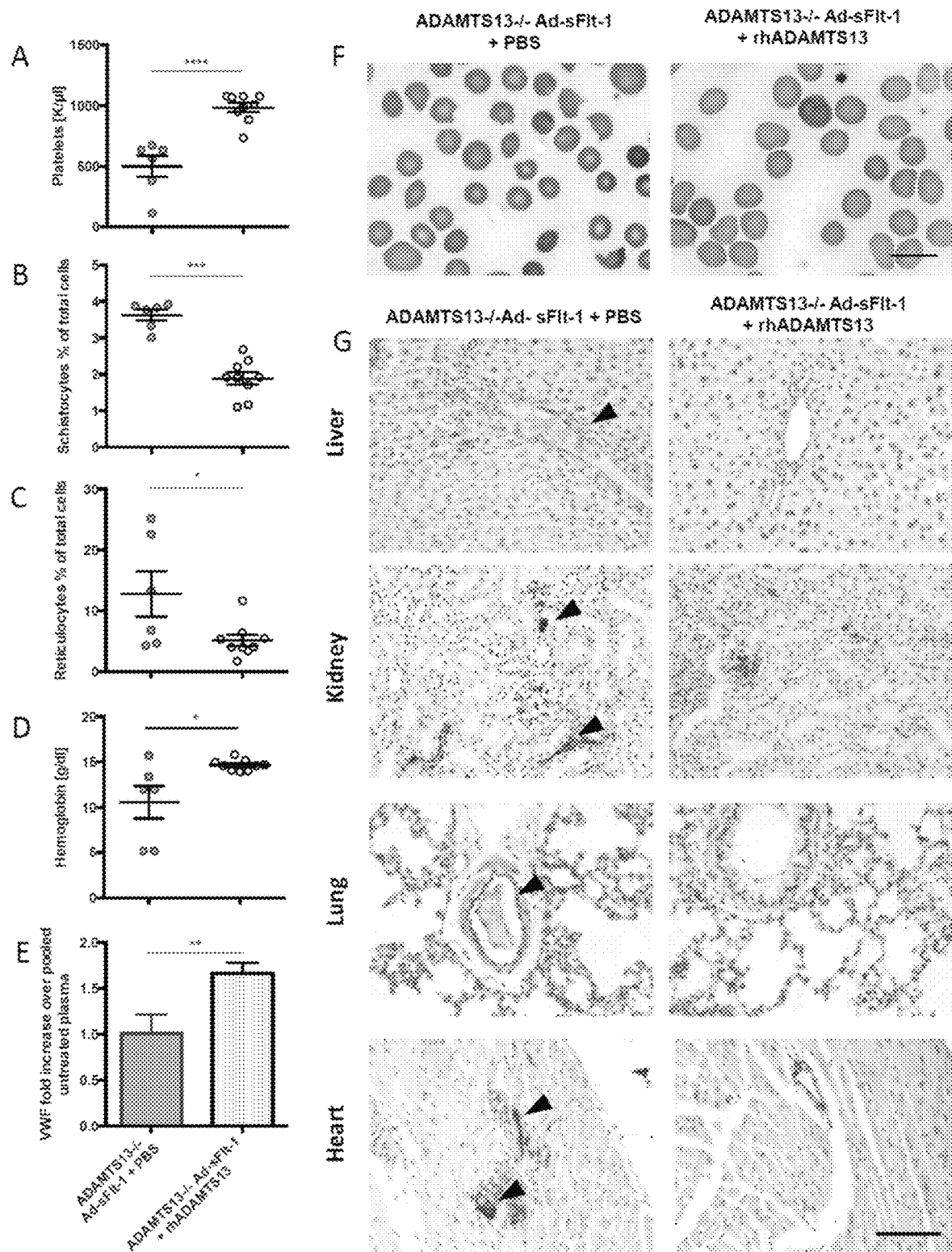
FIGS. 4A-4G demonstrate that treatment with rhADAMTS13 rescues ADAMTS13−/− mice from sFlt-1-induced TMA. ADAMTS13−/− mice were injected with Ad-sFlt-1 virus and then received daily treatment with rhADAMTS13 (or PBS as vehicle control) starting at day 4 after virus injection. By day 7, rhADAMTS13-treated ADAMTS13−/− Ad-sFlt-1 mice showed significant improvements compared to the vehicle-treated ADAMTS13−/− Ad-sFlt-1 mice in (FIG. 4A) platelet counts, (FIG. 4B) schistocyte counts, (FIG. 4C) reticulocyte counts and (FIG. 4D) hemoglobin values (n=6-9 for FIGS. 4A-4D).

To test whether insufficient cleavage of VWF through ADAMTS13 was directly responsible for the observed phenotype in the ADAMTS13−/− Ad-sFlt-1 mice, we attempted to rescue these mice by administering rhADAMTS13 every 24 hours[32], from day 4 to day 7 after virus injection. 7 days after receiving Ad-sFlt-1, ADAMTS13−/− mice that received rhADAMTS13 did not experience a drop in platelet count (FIG. 4A). Blood smears normalized and did not show schistocytosis (FIG. 4B, 4F). Reticulocytes were significantly lowered by rhADAMTS13 treatment (FIG. 4C, 4F) and none of the rhADAMTS13-treated mice developed anemia (FIG. 4D). To exclude that these differences were due to changes in the levels of sFlt-1 expression, sFlt-1 levels were measured in ADAMTS13−/− mice injected with Ad-sFlt-1 and then treated with rhADAMTS13 or PBS. The values between these two groups were not significantly different, with a mean of 4835+/−240.2 ng/ml for the ADAMTS13−/− Ad-sFlt-1+PBS mice compared to 4258.1+/−319.7 ng/ml for the ADAMTS13−/− Ad-sFlt-1+ rhADAMTS13 mice (n=4, P=0.197).

Figures 5A, 5B, 5C, 5D, 5E:
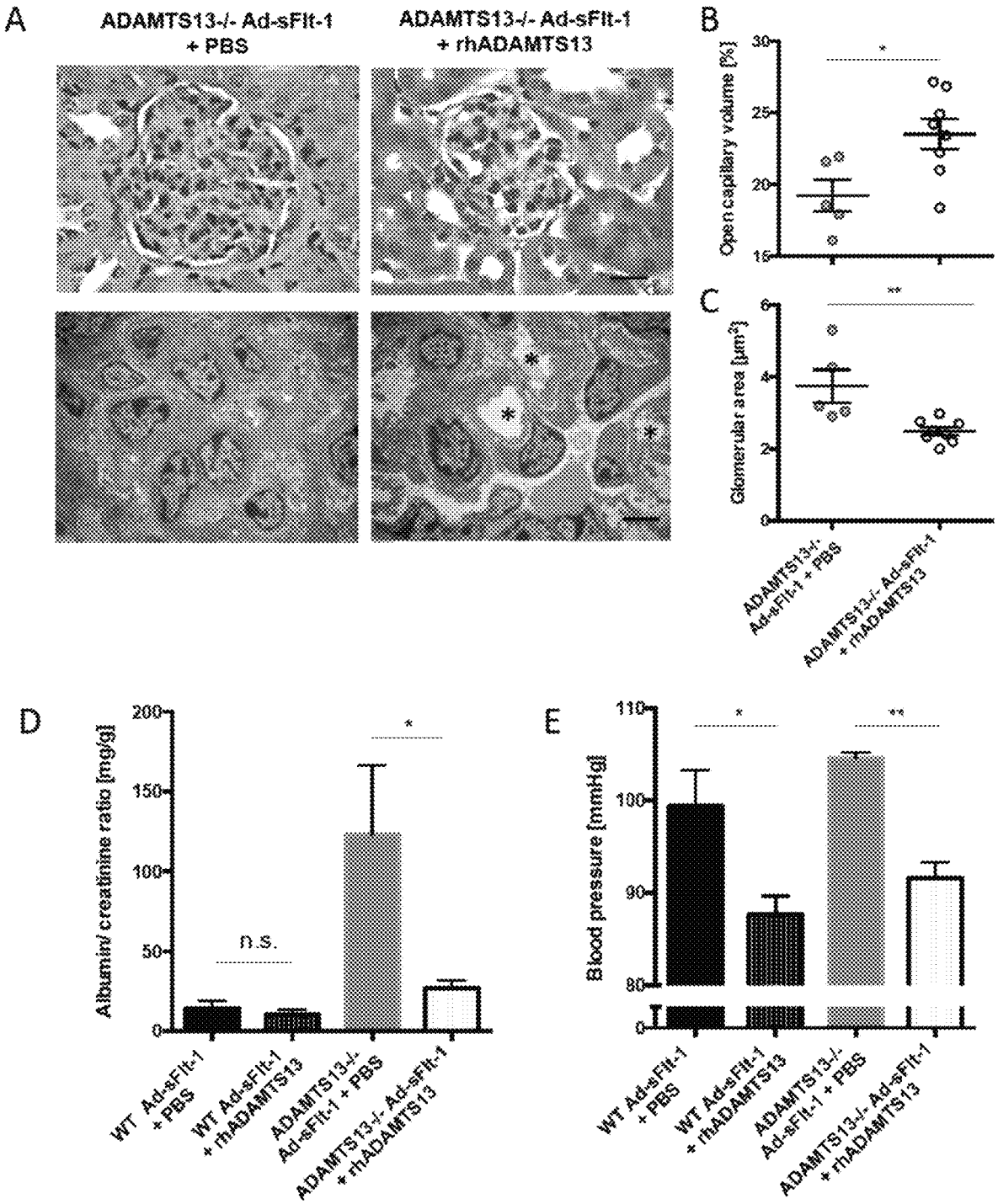
FIGS. 5A-5E demonstrate that kidney damage is reduced by treatment with rhADAMTS13 in ADAMTS13−/− Ad-sFlt-1 mice and blood pressure is normalized in both WT and ADAMTS13−/− mice overexpressing sFlt-1.

Interestingly, in rhADAMTS13-treated ADAMTS13−/− mice after Ad-sFlt-1 challenge, an almost 2-fold increase of plasma VWF was observed compared to vehicle (PBS)-treated ADAMTS13−/− mice by day 7 (FIG. 4E), similar to the WT mice after Ad-sFlt-1 injection (FIG. 1F). This implies that rhADAMTS13 did not prevent the release of VWF after sFlt-1-induced endothelial damage, but that released VWF could now be cleaved and was no longer recruited into thrombi. Indeed, at day 7 after Ad-sFlt-1 injection, formation of microthrombi was reduced by more than 50% in all organ types (Table 2, last 2 rows, FIG. 4G) after rhADAMTS13 treatment in ADAMTS13−/− mice, with the kidneys being the most strongly protected. The rhADAMTS13-treated mice also fared better in terms of kidney histology (FIG. 5A), with a significantly higher open capillary volume (FIG. 5B) and smaller glomeruli (FIG. 5C). Kidney function of ADAMTS13−/− Ad-sFlt-1 mice became comparable to that of control mice upon treatment with rhADAMTS13 (FIG. 5D) and blood pressure in the ADAMTS13−/− Ad-sFlt-1 group normalized (FIG. 5E).

As WT mice had shown a modest rise in their albumin-creatinine values as well as an increase in blood pressure after Ad-sFlt-1-injection, WT Ad-sFlt-1 mice were also given rhADAMTS13. Albumin-creatinine values decreased after rhADAMTS13 treatment, although this did not reach significance (FIG. 5D). Astonishingly, blood pressure in WT Ad-sFlt-1 mice was completely normalized by rhADAMTS13, implying that additional rhADAMTS13 can be helpful even in the presence of endogenous ADAMTS13 (FIG. 5E).

DISCUSSION

TMA associated with VEGF inhibitors can occur in cancer therapies or through high levels of endogenous circulating sFlt-1 as in severe preeclampsia/l HELLP syndrome. In both cases, TMA confers significant morbidity and mortality to patients.[3, 17, 33, 34] However, the mechanisms underlying VEGF-related TMA are still poorly understood and prognostic criteria to identify patients at risk are lacking. Described herein is an animal model of VEGF-related TMA in ADAMTS13−/− mice and the finding that replenishment of ADAMTS13 rescues the classic features of TMAs, including thrombocytopenia, schistocytosis, hemolytic anemia and microthrombosis in multiple organs. These findings have direct implications for the prediction and treatment of VEGF-related TMA or thrombosis arising in humans.

The development of animal models for TMAs is valuable both for understanding fundamental disease mechanisms and for pursuing new treatment strategies. Complete VEGF deletion from kidney podocytes is sufficient to induce renal TMA,[17] a finding that may account for the prominent renal manifestations of clinical VEGF inhibitor toxicity.[35, 36] In the present model of systemic VEGF inhibition, renal microthrombosis and proteinuria were also among the most prominent findings in the ADAMTS13−/− mice. Without wishing to be bound by theory, VEGF-inhibitor-related TMA is predominantly noted in the vascular bed of the kidneys as VEGF is constitutively expressed in the adult glomerular podocytes.[37] However, using a systemic agent, it is possible that the same local level of VEGF-inhibition in the podocytes was not reached, which would explain the less severe phenotype in our WT mice.

In addition to the above-mentioned model of renal TMA, a limited number of mouse models for congenital TTP and a baboon model for acquired TTP have been established.[38] Interestingly, ADAMTS13−/− mice, similar to humans deficient in the enzyme, do not readily develop TTP,[39] but require additional triggers to provoke the onset of the disease. Such triggers include shigatoxin injection,[27] administration of recombinant human VWF containing UL-VWF multimers,[28] or by genetically rendering the VWF molecule resistant to cleavage by ADAMTS13.[40] Thus, in the present work, VEGF inhibition may be viewed as the second hit, which then triggers TTP-like symptoms in ADAMTS13−/− mice. Indeed, pregnancy—a known trigger of TTP for patients with ADAMTS13 deficiency[41]—also leads to a physiological increase of plasma sFlt-1 (without reaching the very high levels found in preeclamptic women), giving more weight to the putative connection between low ADAMTS13, sFlt-1 overexpression and TMA.[21]

In analogy to the model using recombinant human VWF injection,[28] our model increased VWF-concentration in the blood of anti-VEGF treated mice. Inhibitors of VEGF function like sFlt-1 are known to cause endothelial activation[42] and release of VWF.[11, 43] In the ADAMTS13−/− Ad sFlt-1 mice, the released hyperactive VWF cannot be cleaved readily, leading to fully developed TMA. In the WT group, plasma VWF also increased after sFlt-1 overexpression; however, the mice only showed minor symptoms including increased blood pressure, a mild drop in platelet count and an increase in reticulocyte numbers and hemoglobin. Most likely the latter two can be seen as a compensation for a low-grade destruction of red blood cells which was too minor to be detected. It is conceivable that in WT animals, an initial, overwhelming release of large numbers of Weibel-Palade bodies from the vasculature leads to transient consumption of ADAMTS13, a drop in platelets and initiation of a thrombotic reaction, which is abrogated as the released VWF is cleaved into smaller, less active multimers.[44] If patients have compromised ADAMTS13 activity or levels, release of UL-VWF with consumption of existing ADAMTS13 in microthrombosis could start a vicious circle leading to severe disease. Additionally, VWF directly influences inflammation by promoting the extravasation of leukocytes and the destabilization of the endothelial barrier.[45] ADAMTS13−/− mice display increased leukocyte rolling and enhanced extravasation of neutrophils in thioglycollate-induced peritonitis.[46] Moreover, treatment with rhADAMTS13 has a strong anti-inflammatory effect in models of ischemic brain injury,[47] atherosclerosis[48] and myocardial infarction.[32] Thus, the interplay between ADAMTS13 and VWF exerts a role in more than the regulation of thrombosis.

Clinical manifestations of ADAMTS13 deficiency are relatively rare in the general population[49]. However, autoantibodies against the enzyme are present in up to 5% of healthy individuals[50, 51] and might become problematic under VEGF-inhibition. In addition, certain patient groups such as those suffering from immuno-mediated diseases like systemic lupus erythematosus and the antiphospholipid antibody syndrome can be far more susceptible to the development of inhibitory autoantibodies.[51] Finally, the two patient groups most likely to be exposed to high levels of VEGF-inhibitors—cancer patients and preeclamptic women—are known to have significantly decreased levels of ADAMTS13 activity or antigen. In patients with metastatic disease, ADAMTS13 activity can be severely reduced by 50%-95%.[52, 53] Likewise, small studies have reported a decrease in ADAMTS13 activities in patients with severe preeclampsia, with ADAMTS13 activity ≤70% being associated with early-onset preeclampsia, independent of VWF-Ag levels.[11, 54] However, it is not known if these alterations antedate clinical symptoms.

The results described herein indicate that low ADAMTS13 enzyme activity can lead to severe clinical consequences when exposed to anti-VEGF state. Thus, determining the activity of ADAMTS13 before treatment with a VEGF inhibitor and possibly monitoring it during treatment could be an important step to assess the susceptibility of the patient to TMA.

To date, the only specific therapy for TMAs resulting from VEGF-inhibition is the removal of the inhibitory agent,[4, 19, 57] interrupting either the cancer treatment or, in the case of preeclampsia/HELLP patients, terminating pregnancy and delivering the placenta. Because of the great need for novel therapeutic approaches to prevent TMA, it was tested whether ADAMTS13−/− mice could be cured of TMA by administering rhADAMTS13. Indeed, the ADAMTS13−/− mice treated with rhADAMTS13 were, for the most part, protected from TMA under VEGF-inhibition. Thrombus formation was still visible in a low number of mice, but overall thrombotic events were greatly reduced. In the WT Ad-sFlt-1 mice, treatment with rhADAMTS13 also normalized blood pressure. Without wishing to be bound by theory, it is contemplated that the above-mentioned beginning of a thrombotic reaction in the WT Ad-sFlt-1 mice was sufficient to cause some amount of kidney damage and a subsequent rise in blood pressure, which was impeded by rhADAMTS13 treatment.

The findings described herein demonstrate that ADAMTS13−/− mice are more prone to blood pressure elevation upon challenge with sFlt-1. Enhanced renal damage may contribute to hypertension.

The data presented herein indicate that rhADAMTS13 is an effective treatment option in patients suffering from anti-VEGF treatment-associated TMA with either reduced ADAMTS13 activity or even with normal activity, as supernormal ADAMTS13 levels appear to be beneficial during anti-VEGF therapy. Other treatment options include antibodies or aptamers which directly target the A1-domain of VWF that promotes platelet binding and which are also being developed for use in TTP patients.[60, 61] Finally, N-acetylcysteine (NAC) was shown to reduce the size and activity of VWF in human and mouse plasma[62] and has been successfully used in refractory TTP in one patient.[63]

Described herein is an important role for ADAMTS13 in preventing TMA following systemic VEGF inhibition. Contemplated herein is the treatment of cancer patients that need anti-VEGF treatment with rhADAMTS13, as it can reduce thrombotic complications and halt or even reverse the development of TMA symptoms.

Materials and Methods

Animals.

ADAMTS13−/−[64] and wild-type (WT) mice were on a C57BL/6J background. Animals were 11-12 weeks old and sex- and weight matched. All experimental procedures were reviewed and approved by the Institutional Animal Care and Use Committee of Boston Children's Hospital (protocol no. 13-06-2427).

sFlt-1 Overexpression:

Mice received lateral tail vein injections with $2.2 \times 10^9$ PFU units of adenovirus encoding sFlt-1 (Ad-sFlt-1) or empty CMV (Ad-null) at equivalent doses. The details of the virus construction is described elswhere and were amplified at the Vector Laboratories.[21, 25, 29]

Recombinant ADAMTS13 (rhADAMTS13) Treatment.

Treatment with rhADAMTS13 (or PBS vehicle) by retroorbital intravenous injections was started at day 4 after virus injection at a dose of 3460 U/kg every 24 hours[32] until day 7 after virus injection.

Analysis of Peripheral Blood.

Blood was collected via the retroorbital sinus into EDTA-coated capillary tubes and was analyzed by a Hemavet 950FS™ (Drew Scientific) for complete blood counts. Peripheral blood smears were prepared by standard procedures and fixed in methanol. Blood smears were stained with Wright-Giemsa stain (Sigma) and schistocytes and reticulocytes were counted in a blinded manner as percent of total cells, according to the recommendations of the International Council for Standardization in Haematology (ICSH).[65]

ELISAs:

Plasma sFlt-1 levels were measured using the Mouse sVEGF R1/Flt-1 Quantikine™ ELISA Kit (R&D Systems) in mouse plasma at day 7 and day 10 after virus injection. Plasma VWF levels were quantified by ELISA on day 7.[27, 64] VWF levels in plasma of WT or ADAMTS13−/− mice were calculated and shown as fold increase over pooled plasma VWF levels of untreated WT or untreated ADAMTS13−/− mice, respectively Tissue Preparation and Analysis.

Mice were anesthetized with Avertin™ (tribromoethanol). Perfusion was performed with 15 mL of PBS through the heart via the left ventricle. Organs were harvested and fixed in zinc fixative (100 mM Tris-HCl containing 37 mM zinc chloride, 23 mM zinc acetate, and 3.2 mM calcium acetate). Paraffin-embedded sections were stained with H&E. Glomerular area and open capillary volume was analyzed using ImageJ™ (National Institutes of Health, Bethesda, Md.) on at least 20 H&E stained glomeruli per mouse, as described previously.[29] VWF immunohistochemistry staining was performed.[27] Slides were evaluated by light microscopy using a Zeiss Axioplan™ microscope and Axiovision™ software.

Urine Analysis:

Urine was collected before Ad-null or Ad-sFlt-1 injection and after injection on day 4, 7 and 10. Albumin was measured using the Albuwell M kit (Exocell) according to the manufacturer's instructions. Creatinine was determined using the Creatinine (urinary) Colorimetric Assay Kit (Cayman Chemical) and the ratio between albumin and creatinine was calculated.

Blood Pressure Measurements:

Systolic blood pressure was measured before Ad-null or Ad-sFlt-1 injection and after on day 7 and 10, using a IITC 12M22931 non-invasive blood pressure system (IITC Life Science), a validated method that has been compared to both telemetry and direct blood pressure measurements.[66, 67]

Mice were trained twice several days before the onset of measurements to get them accustomed to the procedure. For this, mice were placed in restrainers and allowed to settle down for 10 min in the tail-cuff chamber at 34° C. The non-invasive blood pressure methodology employs a tail-cuff placed on the proximal part of the tail to occlude the blood flow. Upon deflation, the system uses a highly sensitive photoelectric sensor for detection of blood pressure pulses. Blood pressure was measured 5 times and the average value is presented.

Electron Microscopy:

Harvested kidneys were fixed in glutaraldehyde and embedded in araldite-epon mixture; 1 μm sections were cut and stained with Toluidine blue. Electron microscopy images were acquired using a Hamamatsu Orca-HR™ Digital Camera and Advanced Microscopy Techniques (AMT) Corp. image capture system.

Statistical Analysis.

Data are presented as mean±SEM. For statistical tests, a two-sided Student's t-test was used when two groups were compared. For comparison of more than two groups, the ANOVA test with Bonferroni adjustment was applied. The Chi-square test was employed for analysis of table 2.

Flow Cytometry:

Blood was collected using an EDTA-coated capillary from the retroorbital plexus. 10 μl of full blood were diluted in 100 μl PBS containing 0.1% sodium azide (Sigma) and 2% FCS. Platelets were labeled using APC-conjugated anti-GPIX antibody or corresponding isotype control (both BioLegend), according to standard protocols (Nieswandt, B, Schulte, V, Bergmeier, W: Flow-cytometric analysis of mouse platelet function. Methods Mol Biol, 272: 255-268, 2004). Platelet counts were determined by flow cytometry (BD FACSCantoII™) and analyzed using FlowJo™ software (TreeStar Inc., Version 8.8.7)

REFERENCES

1. Besbas, N, Karpman, D, Landau, D, Loirat, C, Proesmans, W, Remuzzi, G, Rizzoni, G, Taylor, C M, Van de Kar, N, Zimmerhackl, L B, European Paediatric Research Group for, HUS: A classification of hemolytic uremic syndrome and thrombotic thrombocytopenic purpura and related disorders. *Kidney international,* 70: 423-431, 2006.
2. Rosove, M H: Thrombotic microangiopathies. *Seminars in arthritis and rheumatism,* 43: 797-805, 2014.
3. Powe, C E, Levine, R J, Karumanchi, S A: Preeclampsia, a disease of the maternal endothelium: the role of anti-angiogenic factors and implications for later cardiovascular disease. *Circulation,* 123: 2856-2869, 2011.
4. Haram, K, Svendsen, E, Abildgaard, U: The HELLP syndrome: clinical issues and management. A Review. *BMC pregnancy and childbirth,* 9: 8, 2009.
5. Bianchi, V, Robles, R, Alberio, L, Furlan, M, Lammle, B: Von Willebrand factor-cleaving protease (ADAMTS13) in thrombocytopenic disorders: a severely deficient activity is specific for thrombotic thrombocytopenic purpura. *Blood,* 100: 710-713, 2002.
6. Furlan, M, Lammle, B: Aetiology and pathogenesis of thrombotic thrombocytopenic purpura and haemolytic uraemic syndrome: the role of von Willebrand factor-cleaving protease. *Best practice & research Clinical haematology,* 14: 437-454, 2001.
7. Lammle, B, Kremer Hovinga, J A, Alberio, L: Thrombotic thrombocytopenic purpura. *Journal of thrombosis and haemostasis: JTH,* 3: 1663-1675, 2005.
8. Dong, J F, Moake, J L, Nolasco, L, Bernardo, A, Arceneaux, W, Shrimpton, C N, Schade, A J, McIntire, L V, Fujikawa, K, Lopez, J A: ADAMTS-13 rapidly cleaves newly secreted ultralarge von Willebrand factor multimers on the endothelial surface under flowing conditions. *Blood,* 100: 4033-4039, 2002.
9. Radhi, M, Carpenter, S L: Thrombotic microangiopathies. *ISRN hematology,* 2012: 310596, 2012.
10. Blake-Haskins, J A, Lechleider, R J, Kreitman, R J: Thrombotic microangiopathy with targeted cancer agents. *Clinical cancer research: an official journal of the American Association for Cancer Research,* 17: 5858-5866, 2011.
11. Aref, S, Goda, H: Increased VWF antigen levels and decreased ADAMTS13 activity in preeclampsia. *Hematology,* 18: 237-241, 2013.
12. Veyradier, A, Obert, B, Haddad, E, Cloarec, S, Nivet, H, Foulard, M, Lesure, F, Delattre, P, Lakhdari, M, Meyer, D, Girma, J P, Loirat, C: Severe deficiency of the specific von Willebrand factor-cleaving protease (ADAMTS13) activity in a subgroup of children with atypical hemolytic uremic syndrome. *The Journal of pediatrics,* 142: 310-317, 2003.
13. Zhu, X, Wu, S, Dahut, W L, Parikh, C R: Risks of proteinuria and hypertension with bevacizumab, an antibody against vascular endothelial growth factor: systematic review and meta-analysis. *American journal of kidney diseases: the official journal of the National Kidney Foundation,* 49: 186-193, 2007.
14. Feldman, D R, Baum, M S, Ginsberg, M S, Hassoun, H, Flombaum, C D, Velasco, S, Fischer, P, Ronnen, E, Ishill, N, Patil, S, Motzer, R J: Phase I trial of bevacizumab plus escalated doses of sunitinib in patients with metastatic renal cell carcinoma. *Journal of clinical oncology: official journal of the American Society of Clinical Oncology,* 27: 1432-1439, 2009.
15. Bollee, G, Patey, N, Cazajous, G, Robert, C, Goujon, J M, Fakhouri, F, Bruneval, P, Noel, L H, Knebelmann, B: Thrombotic microangiopathy secondary to VEGF pathway inhibition by sunitinib. *Nephrology, dialysis, trans-* plantation: *official publication of the European Dialysis and Transplant Association-European Renal Association,* 24: 682-685, 2009.
16. Jin, K, Shen, Y, He, K, Xu, Z, Li, G, Teng, L: Aflibercept (VEGF Trap): one more double-edged sword of anti-VEGF therapy for cancer? *Clinical & translational oncology: official publication of the Federation of Spanish Oncology Societies and of the National Cancer Institute of Mexico,* 12: 526-532, 2010.
17. Eremina, V, Jefferson, J A, Kowalewska, J, Hochster, H, Haas, M, Weisstuch, J, Richardson, C, Kopp, J B, Kabir, M G, Backx, P H, Gerber, H P, Ferrara, N, Barisoni, L, Alpers, C E, Quaggin, S E: VEGF inhibition and renal thrombotic microangiopathy. *The New England journal of medicine,* 358: 1129-1136, 2008.
18. Tew, W P, Gordon, M, Murren, J, Dupont, J, Pezzulli, S, Aghajanian, C, Sabbatini, P, Mendelson, D, Schwartz, L, Gettinger, S, Psyrri, A, Cedarbaum, J M, Spriggs, D R: Phase 1 study of aflibercept administered subcutaneously to patients with advanced solid tumors. *Clinical cancer research: an official journal of the American Association for Cancer Research,* 16: 358-366, 2010.
19. Vigneau, C, Lorcy, N, Dolley-Hitze, T, Jouan, F, Arlot-Bonnemains, Y, Laguerre, B, Verhoest, G, Goujon, J M, Belaud-Rotureau, M A, Rioux-Leclercq, N: All anti-vascular endothelial growth factor drugs can induce 'pre-eclampsia-like syndrome': a RARe study. *Nephrology, dialysis, transplantation: official publication of the European Dialysis and Transplant Association-European Renal Association,* 29: 325-332, 2014.
20. Patel, T V, Morgan, J A, Demetri, G D, George, S, Maki, R G, Quigley, M, Humphreys, B D: A preeclampsia-like syndrome characterized by reversible hypertension and proteinuria induced by the multitargeted kinase inhibitors sunitinib and sorafenib. *Journal of the National Cancer Institute,* 100: 282-284, 2008.
21. Maynard, S E, Min, J Y, Merchan, J, Lim, K H, Li, J, Mondal, S, Libermann, T A, Morgan, J P, Sellke, F W, Stillman, I E, Epstein, F H, Sukhatme, V P, Karumanchi, S A: Excess placental soluble fms-like tyrosine kinase 1 (sFlt1) may contribute to endothelial dysfunction, hypertension, and proteinuria in preeclampsia. *The Journal of clinical investigation,* 111: 649-658, 2003.
22. Levine, R J, Maynard, S E, Qian, C, Lim, K H, England, L J, Yu, K F, Schisterman, E F, Thadhani, R, Sachs, B P, Epstein, F H, Sibai, B M, Sukhatme, V P, Karumanchi, S A: Circulating angiogenic factors and the risk of preeclampsia. *The New England journal of medicine,* 350: 672-683, 2004.
23. Bergmann, A, Ahmad, S, Cudmore, M, Gruber, A D, Wittschen, P, Lindenmaier, W, Christofori, G, Gross, V, Gonzalves, A, Grone, H J, Ahmed, A, Weich, H A: Reduction of circulating soluble Flt-1 alleviates preeclampsia-like symptoms in a mouse model. *Journal of cellular and molecular medicine,* 14: 1857-1867, 2010.
24. Li, Z, Zhang, Y, Ying Ma, J, Kapoun, A M, Shao, Q, Kerr, I, Lam, A, O'Young, G, Sannajust, F, Stathis, P, Schreiner, G, Karumanchi, S A, Protter, A A, Pollitt, N S: Recombinant vascular endothelial growth factor 121 attenuates hypertension and improves kidney damage in a rat model of preeclampsia. *Hypertension,* 50: 686-692, 2007.
25. Kuo, C J, Farnebo, F, Yu, E Y, Christofferson, R, Swearingen, R A, Carter, R, von Recum, H A, Yuan, J, Kamihara, J, Flynn, E, D'Amato, R, Folkman, J, Mulligan, R C: Comparative evaluation of the antitumor activity of antiangiogenic proteins delivered by gene transfer. *Proceedings of the National Academy of Sciences of the United States of America,* 98: 4605-4610, 2001.
26. Lopez, J A, Chung, D W: VWF self-association: more bands for the buck. *Blood,* 116: 3693-3694, 2010.
27. Motto, D G, Chauhan, A K, Zhu, G, Homeister, J, Lamb, C B, Desch, K C, Zhang, W, Tsai, H M, Wagner, D D, Ginsburg, D: Shigatoxin triggers thrombotic thrombocytopenic purpura in genetically susceptible ADAMTS13-deficient mice. *The Journal of clinical investigation,* 115: 2752-2761, 2005.
28. Schiviz, A, Wuersch, K, Piskernik, C, Dietrich, B, Hoellriegl, W, Rottensteiner, H, Scheiflinger, F, Schwarz, H P, Muchitsch, E M: A new mouse model mimicking thrombotic thrombocytopenic purpura: correction of symptoms by recombinant human ADAMTS13. *Blood,* 119: 6128-6135, 2012.
29. Li, F, Hagaman, J R, Kim, H S, Maeda, N, Jennette, J C, Faber, J E, Karumanchi, S A, Smithies, O, Takahashi, N: eNOS deficiency acts through endothelin to aggravate sFlt-1-induced pre-eclampsia-like phenotype. *Journal of the American Society of Nephrology: JASN,* 23: 652-660, 2012.
30. Kamba, T, McDonald, D M: Mechanisms of adverse effects of anti-VEGF therapy for cancer. *British journal of cancer,* 96: 1788-1795, 2007.
31. Stillman, I E, Karumanchi, S A: The glomerular injury of preeclampsia. *Journal of the American Society of Nephrology: JASN,* 18: 2281-2284, 2007.
32. Savchenko, A S, Borissoff, J I, Martinod, K, De Meyer, S F, Gallant, M, Erpenbeck, L, Brill, A, Wang, Y, Wagner, D D: VWF-mediated leukocyte recruitment with chromatin decondensation by PAD4 increases myocardial ischemia/reperfusion injury in mice. *Blood,* 123: 141-148, 2014.
33. Vigil-De Gracia, P: Maternal deaths due to eclampsia and HELLP syndrome. *International journal of gynaecology and obstetrics: the official organ of the International Federation of Gynaecology and Obstetrics,* 104: 90-94, 2009.
34. Hayman, S R, Leung, N, Grande, J P, Garovic, V D: VEGF inhibition, hypertension, and renal toxicity. *Current oncology reports,* 14: 285-294, 2012.
35. Frangie, C, Lefaucheur, C, Medioni, J, Jacquot, C, Hill, G S, Nochy, D: Renal thrombotic microangiopathy caused by anti-VEGF-antibody treatment for metastatic renal-cell carcinoma. *Lancet Oncol,* 8: 177-178, 2007.
36. Stokes, M B, Erazo, M C, D'Agati, V D: Glomerular disease related to anti-VEGF therapy. *Kidney international,* 74: 1487-1491, 2008.
37. Eremina, V, Cui, S, Gerber, H, Ferrara, N, Haigh, J, Nagy, A, Ema, M, Rossant, J, Jothy, S, Miner, J H, Quaggin, S E: Vascular endothelial growth factor a signaling in the podocyte-endothelial compartment is required for mesangial cell migration and survival. *Journal of the American Society of Nephrology: JASN,* 17: 724-735, 2006.
38. Vanhoorelbeke, K, De Meyer, S F: Animal models for thrombotic thrombocytopenic purpura. *Journal of thrombosis and haemostasis: JTH,* 11 Suppl 1: 2-10, 2013.
39. Banno, F, Kokame, K, Okuda, T, Honda, S, Miyata, S, Kato, H, Tomiyama, Y, Miyata, T: Complete deficiency in ADAMTS13 is prothrombotic, but it alone is not sufficient to cause thrombotic thrombocytopenic purpura. *Blood,* 107: 3161-3166, 2006.
40. Morioka, Y, Casari, C, Wohner, N, Cho, S, Kurata, S, Kitano, A, Christophe, O D, Lenting, P J, Li, R, Denis, C V, Prevost, N: Expression of a structurally constrained 41. Fujimura, Y, Matsumoto, M, Kokame, K, Isonishi, A, Soejima, K, Akiyama, N, Tomiyama, J, Natori, K, Kuranishi, Y, Imamura, Y, Inoue, N, Higasa, S, Seike, M, Kozuka, T, Hara, M, Wada, H, Murata, M, Ikeda, Y, Miyata, T, George, J N: Pregnancy-induced thrombocytopenia and TTP, and the risk of fetal death, in Upshaw-Schulman syndrome: a series of 15 pregnancies in 9 genotyped patients. *British journal of haematology*, 144: 742-754, 2009.

42. Walshe, T E, Dole, V S, Maharaj, A S, Patten, I S, Wagner, D D, D'Amore, P A: Inhibition of VEGF or TGF-{beta} signaling activates endothelium and increases leukocyte rolling. *Arteriosclerosis, thrombosis, and vascular biology*, 29: 1185-1192, 2009.

43. Di Marco, G S, Reuter, S, Hillebrand, U, Amler, S, Konig, M, Larger, E, Oberleithner, H, Brand, E, Pavenstadt, H, Brand, M: The soluble VEGF receptor sFlt1 contributes to endothelial dysfunction in CKD. *Journal of the American Society of Nephrology: JASN*, 20: 2235-2245, 2009.

44. Sadler, J E: Von Willebrand factor, ADAMTS13, and thrombotic thrombocytopenic purpura. *Blood*, 112: 11-18, 2008.

45. Hillgruber, C, Steingraber, A K, Poppelmann, B, Denis, C V, Ware, J, Vestweber, D, Nieswandt, B, Schneider, S W, Goerge, T: Blocking von Willebrand factor for treatment of cutaneous inflammation. *The Journal of investigative dermatology*, 134: 77-86, 2014.

46. Chauhan, A K, Kisucka, J, Brill, A, Walsh, M T, Scheiflinger, F, Wagner, D D: ADAMTS13: a new link between thrombosis and inflammation. *The Journal of experimental medicine*, 205: 2065-2074, 2008.

47. Zhao, B Q, Chauhan, A K, Canault, M, Patten, I S, Yang, J J, Dockal, M, Scheiflinger, F, Wagner, D D: von Willebrand factor-cleaving protease ADAMTS13 reduces ischemic brain injury in experimental stroke. *Blood*, 114: 3329-3334, 2009.

48. Gandhi, C, Khan, M M, Lentz, S R, Chauhan, A K: ADAMTS13 reduces vascular inflammation and the development of early atherosclerosis in mice. *Blood*, 119: 2385-2391, 2012.

49. Murrin, R J, Murray, J A: Thrombotic thrombocytopenic purpura: aetiology, pathophysiology and treatment. *Blood reviews*, 20: 51-60, 2006.

50. Grillberger, R, Casina, V C, Turecek, P L, Zheng, X L, Rottensteiner, H, Scheiflinger, F: Anti-ADAMTS13 IgG autoantibodies present in healthy individuals share linear epitopes with those in patients with thrombotic thrombocytopenic purpura. *Haematologica*, 99: e58-60, 2014.

51. Rieger, M, Mannucci, P M, Kremer Hovinga, J A, Herzog, A, Gerstenbauer, G, Konetschny, C, Zimmermann, K, Scharrer, I, Peyvandi, F, Galbusera, M, Remuzzi, G, Bohm, M, Plaimauer, B, Lammle, B, Scheiflinger, F: ADAMTS13 autoantibodies in patients with thrombotic microangiopathies and other immunomediated diseases. *Blood*, 106: 1262-1267, 2005.

52. Oleksowicz, L, Bhagwati, N, DeLeon-Fernandez, M: Deficient activity of von Willebrand's factor-cleaving protease in patients with disseminated malignancies. *Cancer research*, 59: 2244-2250, 1999.

53. Mannucci, P M, Karimi, M, Mosalaei, A, Canciani, M T, Peyvandi, F: Patients with localized and disseminated tumors have reduced but measurable levels of ADAMTS-13 (von Willebrand factor cleaving protease). *Haematologica*, 88: 454-458, 2003.

54. Stepanian, A, Cohen-Moatti, M, Sanglier, T, Legendre, P, Ameziane, N, Tsatsaris, V, Mandelbrot, L, de Prost, D, Veyradier, A, Group, E S: Von Willebrand factor and ADAMTS13: a candidate couple for preeclampsia pathophysiology. *Arteriosclerosis, thrombosis, and vascular biology*, 31: 1703-1709, 2011.

55. Lechner, K, Simonitsch, I, Haselbock, J, Jager, U, Pabinger, I: Acquired immune-mediated thrombophilia in lymphoproliferative disorders. *Leukemia & lymphoma*, 52: 1836-1843, 2011.

56. Yao, H, Monge, M, Renou, M, Lecaque, C, Jaureguy, M, Presne, C, Makdassi, R, Choukroun, G: Thrombotic thrombocytopenic purpura due to anti-ADAMTS13 antibodies in multiple myeloma. *Clinical nephrology*, 81: 210-215, 2014.

57. Uzan, J, Carbonnel, M, Piconne, O, Asmar, R, Ayoubi, J M: Pre-eclampsia: pathophysiology, diagnosis, and management. *Vascular health and risk management*, 7: 467-474, 2011.

58. Plaimauer, B, Kremer Hovinga, J A, Juno, C, Wolfsegger, M J, Skalicky, S, Schmidt, M, Grillberger, L, Hasslacher, M, Knobl, P, Ehrlich, H, Scheiflinger, F: Recombinant ADAMTS13 normalizes von Willebrand factor-cleaving activity in plasma of acquired TTP patients by overriding inhibitory antibodies. *Journal of thrombosis and haemostasis: JTH*, 9: 936-944, 2011.

59. Piskernik, C, Dietrich B., Kubik S., Ruthsatz T., Scheiflinger, F., Schwarz H. P., Muchitsch E. M.: Preclinical Safety of Baxter's Recombinant ADAMTS13 [abstract]. *54th ASH Annual Meeting and Exposition*: Abstract 3381, 2012.

60. Jilma-Stohlawetz, P, Gilbert, J C, Gorczyca, M E, Knobl, P, Jilma, B: A dose ranging phase I/II trial of the von Willebrand factor inhibiting aptamer ARC 1779 in patients with congenital thrombotic thrombocytopenic purpura. *Thrombosis and haemostasis*, 106: 539-547, 2011.

61. Feys, H B, Roodt, J, Vandeputte, N, Pareyn, I, Mottl, H, Hou, S, Lamprecht, S, Van Rensburg, W J, Deckmyn, H, Vanhoorelbeke, K: Inhibition of von Willebrand factor-platelet glycoprotein Ib interaction prevents and reverses symptoms of acute acquired thrombotic thrombocytopenic purpura in baboons. *Blood*, 120: 3611-3614, 2012.

62. Chen, J, Reheman, A, Gushiken, F C, Nolasco, L, Fu, X, Moake, J L, Ni, H, Lopez, J A: N-acetylcysteine reduces the size and activity of von Willebrand factor in human plasma and mice. *The Journal of clinical investigation*, 121: 593-603, 2011.

63. Li, G W, Rambally, S, Kamboj, J, Reilly, S, Moake, J L, Udden, M M, Mims, M P: Treatment of refractory thrombotic thrombocytopenic purpura with N-acetylcysteine: a case report. *Transfusion*, 54: 1221-1224, 2014.

64. Chauhan, A K, Walsh, M T, Zhu, G, Ginsburg, D, Wagner, D D, Motto, D G: The combined roles of ADAMTS13 and VWF in murine models of TTP, endotoxemia, and thrombosis. *Blood*, 111: 3452-3457, 2008.

65. Zini, G, d'Onofrio, G, Briggs, C, Erber, W, Jou, J M, Lee, S H, McFadden, S, Vives-Corrons, J L, Yutaka, N, Lesesve, J F, International Council for Standardization in, H: ICSH recommendations for identification, diagnostic value, and quantitation of schistocytes. *International journal of laboratory hematology*, 34: 107-116, 2012.

66. Feng, M, Whitesall, S, Zhang, Y, Beibel, M, D'Alecy, L, DiPetrillo, K: Validation of volume-pressure recording tail-cuff blood pressure measurements. *American journal of hypertension*, 21: 1288-1291, 2008.

67. Krege, J H, Hodgin, J B, Hagaman, J R, Smithies, O: A noninvasive computerized tail-cuff system for measuring blood pressure in mice. *Hypertension*, 25: 1111-1115, 1995.

TABLE 1 sFlt-1 plasma levels in WT and ADAMTS13-/- mice at day 7 and day 10 after adenovirus injection.

| Day | WT Ad-sFlt-1 | ADAMTS13-/- Ad-null | ADAMTS13-/- Ad sFlt-1 |
|---|---|---|---|
| Day 7 | 6345.91 ± 576.13 ng/ml ns to ADAMTS13-/- Ad-sFlt-1 day 7 ns to WT Ad-sFlt-1 day 10 (P = 0.076) | 0.63 ± 0.15 ng/ml | 7177.26 ± 286.91 ng/ml * to ADAMTS13-/- Ad-sFlt-1 day 10 |
| Day 10 | 4995.59 ± 388.71 ng/ml ns to ADAMTS13-/- Ad-sFlt-1 day 10 | 0.69 ± 0.12 ng/ml | 4813.54 ± 307.73 ng/ml |

Values are average ± SEM, n = 7-13.
* P < 0.05. There was no significant difference between sFlt-1 plasma levels of WT and ADAMTS13-/- Ad-sFlt-1 mice on day 7 or day 10, respectively. From day 7 to day 10, sFlt-1 levels declined significantly in the ADAMTS13-/- Ad-sFlt-1 mice and showed a trend toward lower sFlt-1 levels in the WT Ad-sFlt-1 mice.

TABLE 2

Organs positive for VWF-rich thrombi in WT and ADAMTS13-/- mice, at day 7 after Ad-sFlt-1 or Ad-null injection and after treatment with rhADAMTS13 or PBS (as vehicle).

| Group | Liver | Kidney | Lung | Heart |
|---|---|---|---|---|
| WT Ad-sFlt-1 | 0/6 (0%) | 1/6 (16%) | 1/6 (16%) | 0/6 (0%) |
| ADAMTS13-/- Ad-null | 0/6 (0%) | 0/6 (0%) | 0/6 (0%) | 1/6 (16%) |
| ADAMTS13-/- Ad-sFlt-1 | 5/6 (83%) ** to WT Ad-sFlt-1 ** to ADAMTS13-/- Ad-null | 6/6 (100%) ** to WT Ad- sFlt-1 *** to ADAMTS13-/- Ad-null | 4/6 (66%) ns to WT Ad- sFlt-1 * to ADAMTS13-/ Ad-null | 5/6 (83%) ** to WT Ad-sFlt-1 * to ADAMTS13-/- Ad-null |
| ADAMTS13-/- Ad-sFlt-1 + PBS | 4/5 (80%) | 5/5 (100%) | 2/5 (40%) | 4/5 (80%) |
| ADAMTS13-/- Ad-sFlt-1 + rhADAMTS13 | 3/9 (33%) ns to ADAMTS13-/- Ad-sFlt-1 + PBS (P = 0.094) | 2/9 (22%) ** to ADAMTS13-/- Ad-sFlt-1 + PBS | 1/9 (11%) ns to ADAMTS13-/- Ad-sFlt-1 + PBS (P = 0.21) | 3/9 (33%) ns to ADAMTS13-/- Ad-sFlt-1 + PBS (P = 0.094) |

Last two rows:
Treatment of ADAMTS13-/- Ad-sFlt-1 mice with PBS (as vehicle) or rhADAMTS13 was carried out from day 4 to day 7 after Ad-sFlt-1 or Ad-null injection.
Statistical comparison between the groups was performed by Chi-square test between the indicated groups.
* P < 0.05;
** P < 0.01;
*** P < 0.001.

TABLE 4

Parameters determined in WT mice 7 days after injection of Ad-null virus

| Parameter | Value | P value compared to untreated WT mice |
|---|---|---|
| Platelet number | 776.75 ± 24.19 K/μl | 0.659 |
| Schistocytes | 0.63 ± 0.15% | 0.45 |
| Reticulocytes | 2.37 ± 0.056% | 0.21 |
| Hemoglobin | 14.23 ± 0.45 g/dl | 0.72 |
| Albumin-creatinine Ratio | 13.7 ± 5.7 | 0.36 |
| Glomerular size | 2.993 ± 149.28 μm$^2$ | Not determined in untreated WT mice |
| Open capillary space per glomerulus | 23.9 ± 1.76% | Not determined in untreated WT mice |

Values are average ± SEM, n = 4 for the WT Ad-null mice.

Example 2

Overexpression of sFlt-1, a circulating VEGF inhibitor, in rodents causes hypertension.[1-3] Moreover, in humans, VEGF inhibitors used in cancer patients are associated with hypertension.[4] As described herein, ADAMTS13-/- mice are more prone to blood pressure elevation upon challenge with sFlt-1. Without wishing to be bound by theory, it is contemplated that hypertension in the setting of ADAMTS13-/- deficiency is likely secondary to worse renal damage (as noted in FIG. 3C and FIG. 5A-5E), which can be prevented by rhADAMTS13 infusions, as ADAMTS13 has both anti-thrombotic and anti-inflammatory activities. Consistent with this hypothesis, cystatin-C levels, a marker of glomerular filtration, were significantly increased in the ADAMTS13-/- mice exposed to sFlt-1.

REFERENCES

1. Li, F, Hagaman, J R, Kim, H S, Maeda, N, Jennette, J C, Faber, J E, Karumanchi, S A, Smithies, O, Takahashi, N: eNOS deficiency acts through endothelin to aggravate sFlt-1-induced pre-eclampsia-like phenotype. *Journal of the American Society of Nephrology*: JASN 23: 652-660, 2012.
2. Maynard, S E, Min, J Y, Merchan, J, Lim, K H, Li, J, Mondal, S, Libermann, T A, Morgan, J P, Sellke, F W, Stillman, I E, Epstein, F H, Sukhatme, V P, Karumanchi, S A: Excess placental soluble fms-like tyrosine kinase 1 (sFlt1) may contribute to endothelial dysfunction, hypertension, and proteinuria in preeclampsia. *The Journal of clinical investigation,* 111: 649-658, 2003.
3. Holwerda, K M, Burke, S D, Faas, M M, Zsengeller, Z, Stillman, I E, Kang, P M, van Goor, H, McCurley, A, Jaffe, I Z, Karumanchi, S A, Lely, A T: Hydrogen sulfide attenuates sFlt1-induced hypertension and renal damage by upregulating vascular endothelial growth factor. *Journal of the American Society of Nephrology:* JASN 25: 717-725, 2014.
4. Patel, T V, Morgan, J A, Demetri, G D, George, S, Maki, R G, Quigley, M, Humphreys, B D: A preeclampsia-like syndrome characterized by reversible hypertension and proteinuria induced by the multitargeted kinase inhibitors sunitinib and sorafenib. *Journal of the National Cancer Institute,* 100: 282-284, 2008.
5. Feng, M, Whitesall, S, Zhang, Y, Beibel, M, D'Alecy, L, DiPetrillo, K: Validation of volume-pressure recording tail-cuff blood pressure measurements. *American journal of hypertension,* 21: 1288-1291, 2008.
6. Krege, J H, Hodgin, J B, Hagaman, J R, Smithies, O: A noninvasive computerized tail-cuff system for measuring blood pressure in mice. *Hypertension,* 25: 1111-1115, 1995.
7. Desch, K, Motto, D: Is there a shared pathophysiology for thrombotic thrombocytopenic purpura and hemolytic-uremic syndrome? *Journal of the American Society of Nephrology:* JASN, 18: 2457-2460, 2007.
8. Motto, D G, Chauhan, A K, Zhu, G, Homeister, J, Lamb, C B, Desch, K C, Zhang, W, Tsai, H M, Wagner, D D, Ginsburg, D: Shigatoxin triggers thrombotic thrombocytopenic purpura in genetically susceptible ADAMTS13-deficient mice. *The Journal of clinical investigation,* 115: 2752-2761, 2005.
9. Eremina, V, Cui, S, Gerber, H, Ferrara, N, Haigh, J, Nagy, A, Ema, M, Rossant, J, Jothy, S, Miner, J H, Quaggin, S E: Vascular endothelial growth factor a signaling in the podocyte-endothelial compartment is required for mesangial cell migration and survival. *Journal of the American Society of Nephrology:* JASN, 17: 724-735, 2006.
10. Tsai, H M: Pathophysiology of thrombotic thrombocytopenic purpura. *International journal of hematology,* 91: 1-19, 2010.
11. Stillman, I E, Karumanchi, S A: The glomerular injury of preeclampsia. *Journal of the American Society of Nephrology:* JASN, 18: 2281-2284, 2007.
12. Eremina, V, Jefferson, J A, Kowalewska, J, Hochster, H, Haas, M, Weisstuch, J, Richardson, C, Kopp, J B, Kabir, M G, Backx, P H, Gerber, H P, Ferrara, N, Barisoni, L, Alpers, C E, Quaggin, S E: VEGF inhibition and renal thrombotic microangiopathy. *The New England journal of medicine,* 358: 1129-1136, 2008.
13. Aref, S, Goda, H: Increased VWF antigen levels and decreased ADAMTS13 activity in preeclampsia. *Hematology,* 18: 237-241, 2013.
14. Stepanian, A, Cohen-Moatti, M, Sanglier, T, Legendre, P, Ameziane, N, Tsatsaris, V, Mandelbrot, L, de Prost, D, Veyradier, A, Group, E S: Von Willebrand factor and ADAMTS13: a candidate couple for preeclampsia pathophysiology. *Arteriosclerosis, thrombosis, and vascular biology,* 31: 1703-1709, 2011.
15. Martinod, K, Demers, M, Fuchs, T A, Wong, S L, Brill, A, Gallant, M, Hu, J, Wang, Y, Wagner, D D: Neutrophil histone modification by peptidylarginine deiminase 4 is critical for deep vein thrombosis in mice. *Proceedings of the National Academy of Sciences of the United States of America,* 110: 8674-8679, 2013.
16. Chauhan, A K, Motto, D G, Lamb, C B, Bergmeier, W, Dockal, M, Plaimauer, B, Scheiflinger, F, Ginsburg, D, Wagner, D D: Systemic antithrombotic effects of ADAMTS13. *The Journal of experimental medicine,* 203: 767-776, 2006.
17. Zhao, B Q, Chauhan, A K, Canault, M, Patten, I S, Yang, J J, Dockal, M, Scheiflinger, F, Wagner, D D: von Willebrand factor-cleaving protease ADAMTS13 reduces ischemic brain injury in experimental stroke. *Blood,* 114: 3329-3334, 2009.
18. Crescente, M, Thomas, G M, Demers, M, Voorhees, J R, Wong, S L, Ho-Tin-Noe, B, Wagner, D D: ADAMTS13 exerts a thrombolytic effect in microcirculation. *Thrombosis and haemostasis,* 108: 527-532, 2012.
19. Furlan, M, Lammle, B: Aetiology and pathogenesis of thrombotic thrombocytopenic purpura and haemolytic uraemic syndrome: the role of von Willebrand factor-cleaving protease. *Best practice & research Clinical haematology,* 14: 437-454, 2001.
20. Vanhoorelbeke, K, De Meyer, S F: Animal models for thrombotic thrombocytopenic purpura. *Journal of thrombosis and haemostasis: JTH,* 11 Suppl 1: 2-10, 2013.

Example 2: ADAMTS13 Deficiency Worsens Colitis and Exogenous ADAMTS13 Administration Decreases Colitis Severity in Mice Inflammatory Bowel Disease (IBD) affects 1.6 million people in the US. Patients with IBD are at increased risk of thrombosis at baseline and even more so with worsening disease. The pathogenesis of IBD and this increased thrombotic risk is incompletely understood. Ultra large von Willebrand Factor (ULVWF) multimers are released from activated endothelium in response to inflammatory stimuli and recruit both platelets and leukocytes. As described herein, ADAMTS13 is an enzyme that cleaves highly adhesive ULVWF into less bioactive smaller multimers releasing them into circulation.

Mice deficient in ADAMTS13 (ADAMTS13$^{-/-}$) have increased leukocyte rolling and adhesion at baseline which increases with inflammatory stimuli. We hypothesized that ADAMTS13$^{-/-}$ mice would have more severe colitis compared to wild type (WT). Chemical (Dextran Sodium Sulfate) colitis was induced in ADAMTS13$^{-/-}$ and WT mice. Colitis was worse in ADAMTS13$^{-/-}$ mice as demonstrated by increased weight loss, worse anemia, clinical and histologic colitis severity.

ADAMTS13$^{-/-}$ mice had increased VWF release with accumulation at inflamed colonic sites and the majority of mice showed one or more submucosal colonic thrombi. Exogenous ADAMTS13 administration in WT mice decreased colitis severity without worsening colonic bleeding. Additionally, several immune-mediated chronic murine colitis models and inflamed colon tissue specimens from IBD patients showed increased VWF release at inflamed sites suggesting a generalizability of the present findings. ADAMTS13 deficiency worsens colitis and propagates intestinal inflammation most likely through increased platelet-leukocyte recruitment and resulting thrombi. ADAMTS13 administration is of therapeutic value by decreasing both colonic inflammation and thrombosis in IBD, thus improving outcomes.

Inflammatory bowel diseases (IBD) which include Crohn disease and ulcerative colitis (UC) are diseases of chronic intestinal inflammation manifesting in relapsing and remitting often bloody diarrhea and debilitating abdominal pain. IBD affects 1.6 million individuals in the US' and is rising in incidence. The precise pathogenesis of IBD remains unknown; it is thought to arise from a combination of genetic predisposition and a dysregulated immune response to an environmental, likely microbial, trigger.[2]

Interestingly, patients with IBD are at three-fold higher risk of developing thromboembolism compared to age-matched controls, and this risk rises further to 15-fold with worsening disease activity[3] (reviewed in Zitomersky et al[4]). Deep vein thrombosis (DVT) and pulmonary embolism (PE) are the most common thrombotic events, but arterial events[5] including cardiovascular disease and mesenteric ischemia are also more prevalent with IBD.[6]

Von Willebrand Factor (VWF) is a large multimeric glycoprotein. In its ultralarge form (ULVWF) it is stored in the Weibel-Palade bodies of the endothelium, and in α-granules of platelets. ULVWF is released upon activation by inflammatory signals or hypoxia[5]. VWF release leads to the initial adhesion of platelets and leukocytes to the vessel wall, a first step in initiating both inflammation and thrombosis[12,15] ULVWF multimers are extremely biologically active as they avidly bind to extracellular matrix[16] and form stronger bonds with platelet GPIb compared to smaller plasma multimers.[17] A disintegrin and metalloproteinase with thrombospondin type I repeats—motif 13 (ADAMTS13) decreases platelet adhesion and VWF-platelet string formation by cleaving hyperactive ULVWF multimers under conditions of fluid shear stress.[18]

Mechanisms of platelet recruitment and the factors that regulate platelet recruitment in colitis are incompletely understood. In Dextran Sodium Sulfate (DSS) colitis, platelets accumulate in venules of the inflamed colon.[22] They bind endothelium and leukocytes bound to the vessel wall. The presence of these adherent platelets and leukocytes in colonic vessels correlates with disease severity[22]. Mice with DSS colitis made thrombocytopenic with anti-platelet antibody rich serum demonstrate marked reductions in leukocyte adhesion.[23] These data highlight the critical roles of platelet and leukocyte recruitment in colitis, and emphasize the importance of understanding their interactions with the vessel wall. ULVWF avidly binds platelets and recruits leukocytes in thrombosis and inflammation but has not been extensively studied in colitis.

Described herein is the role of ADAMTS13 in DSS induced colitis by comparing ADAMTS13−/− and wild-type (WT) mice. The present results show that ADAMTS13 deficiency leads to the accumulation of VWF-rich thrombi in colonic submucosal vessels, increasingly inflamed colonic tissue, and a worse colitis phenotype. Moreover, it is demonstrated herein that treatment of WT mice with recombinant human ADAMTS13 (rhADAMTS13) ameliorates colitis which identifies ADAMTS13 as a potential drug for colitis Materials and Methods Animals.

ADAMTS13$^{-/-}$[24,25] and WT mice were on a C57BL/6J background. Animals were all 6-8 week-old males, weight-matched, who were in-house bred, with the majority from heterozygous by heterozygous crosses and the remaining from in-house bred WT C57BL/6J. Rag2$^{-/-}$, Rag2$^{-/-}$Il10rb$^{-/-}$, Il10rb$^{-/-}$, Was$^{-/-}$ and Was$^{-/-}$Il4$^{-/-}$ mice were on 129 SvEv background.[26,27] All experimental procedures were reviewed and approved by the Institutional Animal Care and Use Committee of Boston Children's Hospital.

DSS Colitis Model.

Acute DSS colitis was induced by administration of DSS salt (3% wt/vol, mol. wt: 36-50 kDa; MP Biomedicals) in autoclaved drinking water for 10 days as described.[28] Fresh DSS was administered on days 3 and 6. Daily weight and clinical colitis scores were measured using an established scoring system based on percentage weight loss (<10%=1, >10%=2, >20%=3), onset of diarrhea (1), bloody diarrhea (2), hunched posture (1) and rectal prolapse (1) for a maximum score of 7.[28]

Recombinant Human ADAMTS13 (rhADAMTS13) Treatment.

Treatment with rhADAMTS13 (or saline vehicle) by retro-orbital intravenous injections was done on day 3-10 at a dose of 3460 U/kg every 24 hours, a concentration shown to decrease leukocyte recruitment in myocardial ischemia reperfusion injury.[29]

Analysis of Peripheral Blood.

Blood was collected via the retro-orbital sinus into EDTA-coated capillary tubes and was analyzed by a Hemavet 950FS (Drew Scientific) for complete blood counts.

Plasma VWF, IL-6, IL-10, Soluble P-Selectin (sPsel) and Thrombin Anti-Thrombin Complexes (TAT).

Plasma VWF levels were quantified by ELISA on day 10.[30] VWF levels in plasma of WT or ADAMTS13$^{-/-}$ mice were calculated and shown as fold increase over pooled plasma VWF levels of untreated WT or untreated ADAMTS13$^{-/-}$ mice, respectively. Interleukin (IL)-6 (Biolegend), IL-10 (R&D Systems), sPsel (R&D Systems), and thrombin anti-thrombin complexes (Abcam) were measured according to the manufacturer's instructions.

Human Tissue Specimens.

Anonymous human colon tissue specimens were obtained from the Pediatric Inflammatory Bowel Disease Biospecimen Repository at Boston Children's Hospital. This repository was approved by the Institutional Review Board of Boston Children's Hospital (Protocol number: IRB-P00000529). Prior to specimen deposit, informed written consent was obtained from study subjects and/or their legal guardians.

Tissue Preparation and Analysis.

Mice were anesthetized with isofluorane and terminally bled from the retro-orbital sinus. Entire spleens were harvested and weighed. Colon length was measured from anal verge to cecum then colons were cut longitudinally and Swiss rolled so the entire colon could be evaluated.[28] Colons were fixed in zinc fixative (100 mM Tris-HCl containing 37 mM zinc chloride, 23 mM zinc acetate, and 3.2 mM calcium acetate). Paraffin-embedded sections were stained with hematoxylin and eosin (H&E) and scored for colitis severity using an established scoring system[31] by an individual blinded to the study groups. Human colon tissue biopsies were embedded in OCT, snap frozen, cryostat sectioned and fixed in zinc as described above.

Immunostaining and Fluorescence Microscopy.

Tissue sections were washed with PBS and permeabilized (0.1% Triton X-100, 0.1% sodium citrate) for 10 min at 4° C. Samples were blocked with 3% (wt/vol) BSA for 90 min at 37° C., rinsed, and then incubated overnight at 4° C. or for 1 h at 37° C. in primary antibody dilution buffer containing 0.3% BSA and rabbit anti-human VWF (DAKO, 1:500) and rat anti-mouse CD31 (1:250, Biolegend). After several washes, samples were incubated for 2 h at room temperature in antibody dilution buffer containing Alexa Fluor-conjugated secondary antibodies in 0.3% BSA in PBS: goat anti-rat Ig (IgG) (Alexa555, 2 µg/mL, Biolegend) donkey anti-rabbit IgG (Alexa488, 1.5 µg/mL, Biolegend), or donkey anti-sheep IgG (Alexa568, 2 µg/mL; Invitrogen). DNA was counterstained with 1 µg/mL Hoechst 33342 and slides were coverslipped with Fluoromount™ gel (Electron Microscopy Sciences). Fluorescent images were acquired using an Axiovert 200 wide field fluorescence microscope (Zeiss) in conjunction with an Axiocam MRm™ monochromatic CCD camera (Zeiss) and analyzed with Zeiss Axiovision™ software. All channels were acquired in grayscale and pseudo colored using Zeiss Axiovision™ or ImageJ™ software (National Institutes of Health). VWF immunofluorescent intensity in colon tissue was quantified by FITC intensity at the same exposure time on the same day divided by DNA area which stained all nuclei so it estimated entire tissue area in 5 separate 20× images.

Statistics.

Data are presented as mean±SEM and analyzed using Student t test or Mann-Whitney U test unless otherwise noted. Data were considered significant when P values were <0.05. For comparison of platelet count and weight loss after DSS colitis induction between WT an ADAMTS13$^{-/-}$ mice (FIG. 12B) an analysis of covariance was used with a 95% confidence interval to determine if there was a difference between the two slopes.

Results

ADAMTS13 Deficiency Results in a More Severe DSS Colitis Phenotype.

Figures 11A, 11B, 11C:
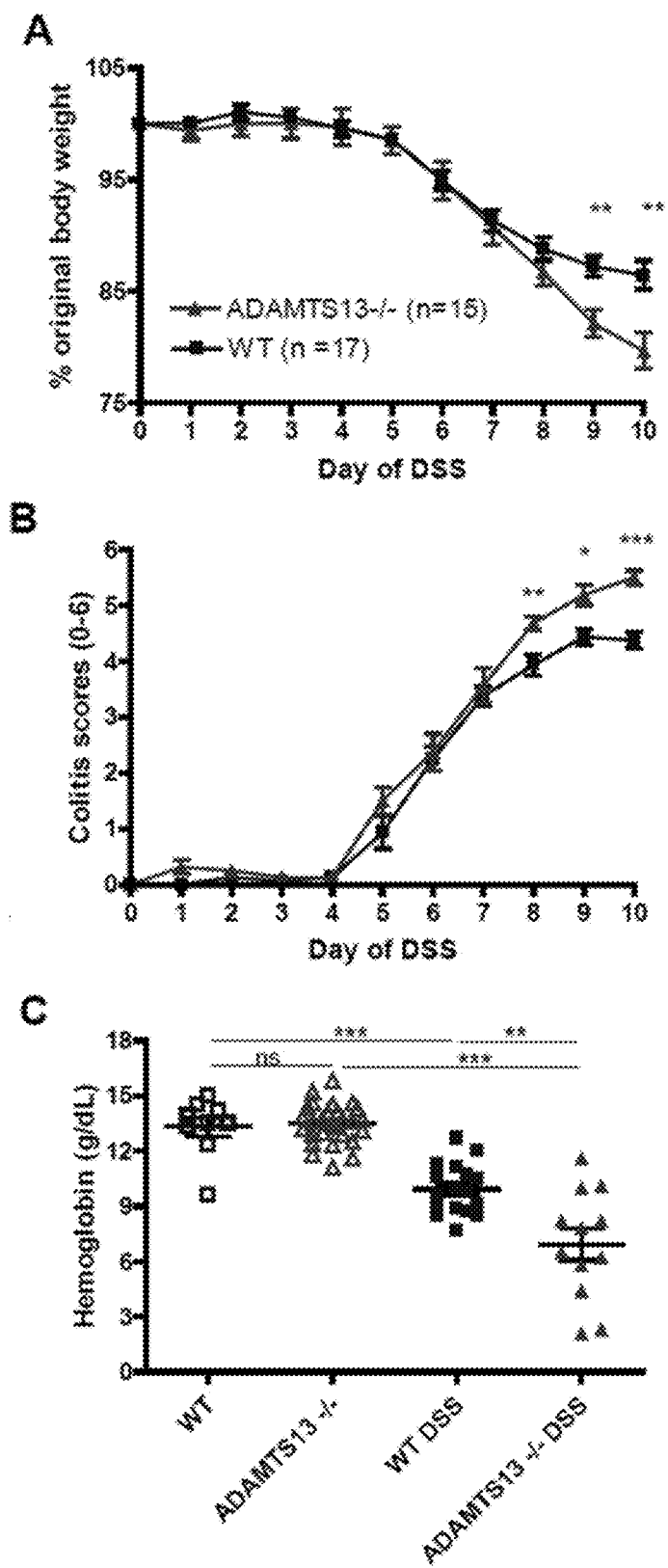
FIGS. 11A-11J demonstrate that ADAMTS13 deficiency aggravates DSS colitis in mice.

To address the role of ADAMTS13 in colonic inflammation, colitis was chemically induced in littermate ADAMTS13$^{-/-}$ and WT mice. Initial body weight did not differ between ADAMTS13$^{-/-}$ and WT mice nor did they have diarrhea at baseline. In three separate experiments, ADAMTS13$^{-/-}$ mice (n=15) with DSS induced colitis lost more weight compared to WT (n=17) on days 9 (P<0.005) and 10 (P<0.0005) when colitis is most severe (FIG. 11A). Clinical colitis scores were also worse on days 8-10 (FIG. 11B; P<0.005, P<0.05, P<0.0005 respectively); this was associated with more weight loss, earlier onset of bloody diarrhea, and hunched body habitus. In colitis, hemoglobin concentration decreases due to blood loss in stool. Hemoglobin concentration did not differ significantly at baseline prior to colitis induction, indicating ADAMTS13 deficiency did not result in clinically significant bleeding without intestinal mucosal injury (FIG. 11C). ADAMTS13$^{-/-}$ mice developed worse anemia (P<0.005) compared to WT mice with colitis (FIG. 11C).

Figures 11D, 11E, 11F, 11G, 11H, 11I, 11J:
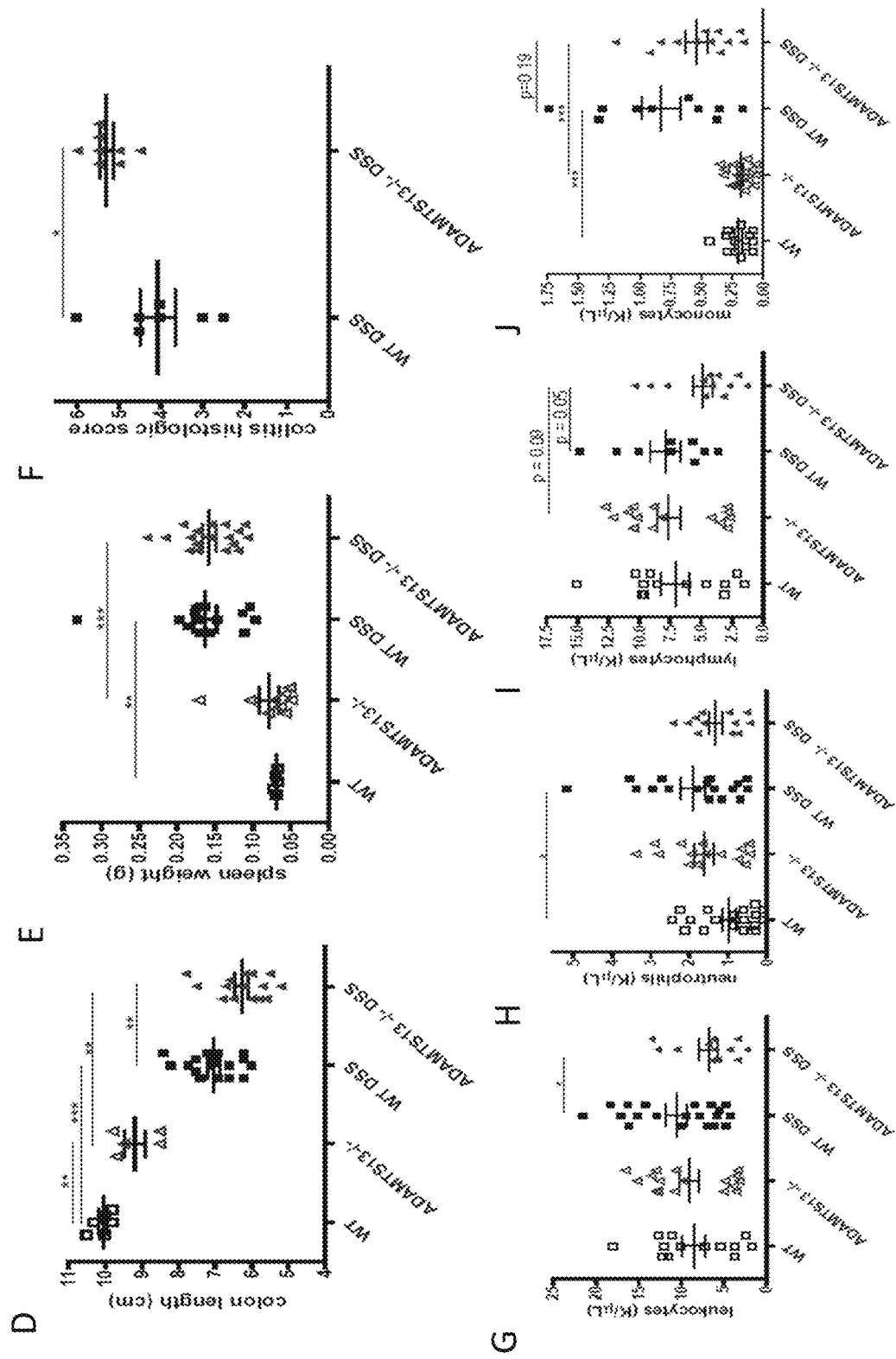

With colonic inflammation the colon becomes edematous and shortens.[28] ADAMTS13$^{-/-}$ mice had slightly shorter colons compared to WT mice even without colitis (FIG. 11D, P<0.005). Because of this slight difference, we looked for microscopic inflammation in H&E stained colon sections from untreated ADAMTS13$^{-/-}$ mice but we found no evidence of inflammation (data not shown). After induction of DSS colitis, colons from ADAMTS13$^{-/-}$ were significantly shorter compared to WT treated mice (P<0.005) as well as untreated ADAMTS13$^{-/-}$ mice suggesting severe colitis (FIG. 11E). Spleen weight is a marker of systemic inflammation in colitis mouse models. Spleen weight increased significantly in both WT and ADAMTS13$^{-/-}$ mice with colitis (P<0.0005) however it did not differ between ADAMTS13$^{-/-}$ and WT mice (FIG. 11E). This and the above observations confirm the induction of severe colitis in both genotypes of mice. Entire H&E stained Swiss rolled colons were evaluated for histologic colitis severity. DSS-treated ADAMTS13$^{-/-}$ colons had more histologic evidence of inflammation compared to WT mice (FIG. 11F, P<0.05).

Blood counts revealed lower total circulating leukocytes in DSS-treated ADAMTS13$^{-/-}$ mice compared to WT mice (FIG. 11G). Circulating leukocyte counts did not differ at baseline (FIG. 1G) Neutrophils increased in WT mice with colitis but were unchanged in ADAMTS13$^{-/-}$ mice with colitis (FIG. 11H). Lymphocytes in WT mice were unchanged, with colitis and tended to be lower in ADAMTS13$^{-/-}$ mice compared to WT mice (FIG. 11I). Monocytes rose significantly in WT and ADAMTS13$^{-/-}$ mice with colitis but did not differ between the two genotypes (FIG. 11J). No significant differences in plasma were observed in the pro-inflammatory cytokine IL-6, or the anti-inflammatory cytokine IL-10, thrombin anti-thrombin complexes (TAT) or soluble P-selectin (sPsel) between WT and ADAMTS13$^{-/-}$ mice with colitis (FIGS. 15A-15D). These results indicate that ADAMTS13-deficiency favors the local accumulation of inflammatory cells in colonic tissue without affecting systemic inflammation.

ADAMTS13$^{-/-}$ Mice Drop their Platelet Count and Develop Colonic Sub-Mucosal Thrombi with Colitis.

Figure 12A:
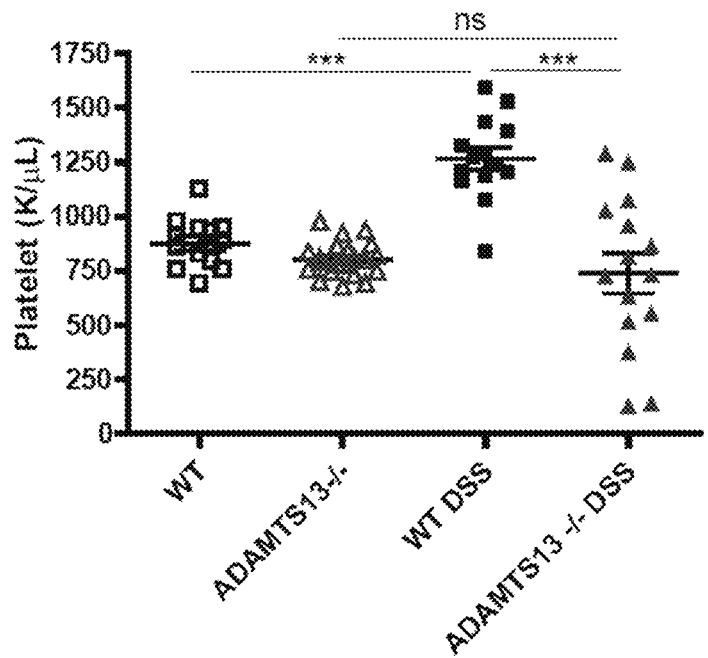
FIGS. 12A-12C demonstrate the effects of ADAMTS13 deficiency on platelet count and colonic thrombosis.
Figure 12B:
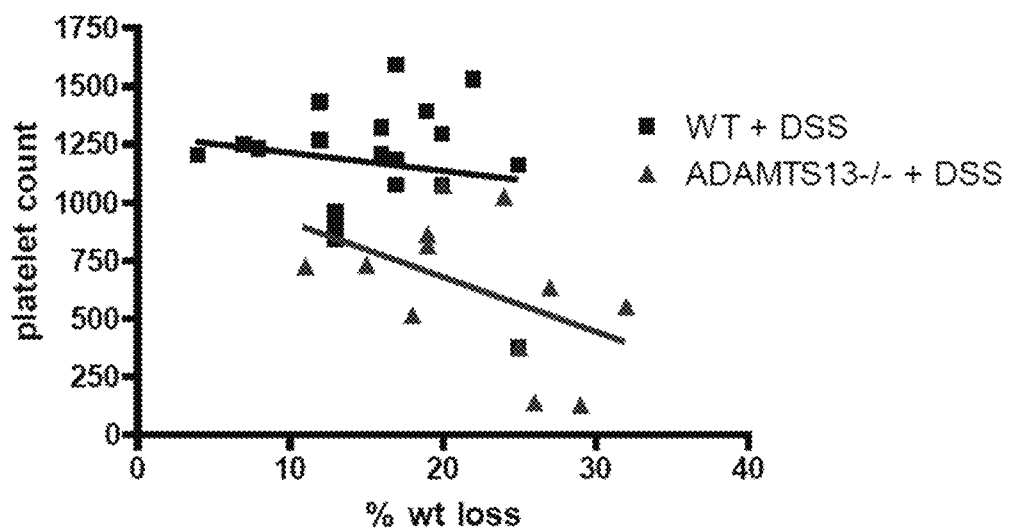
Figure 12C:
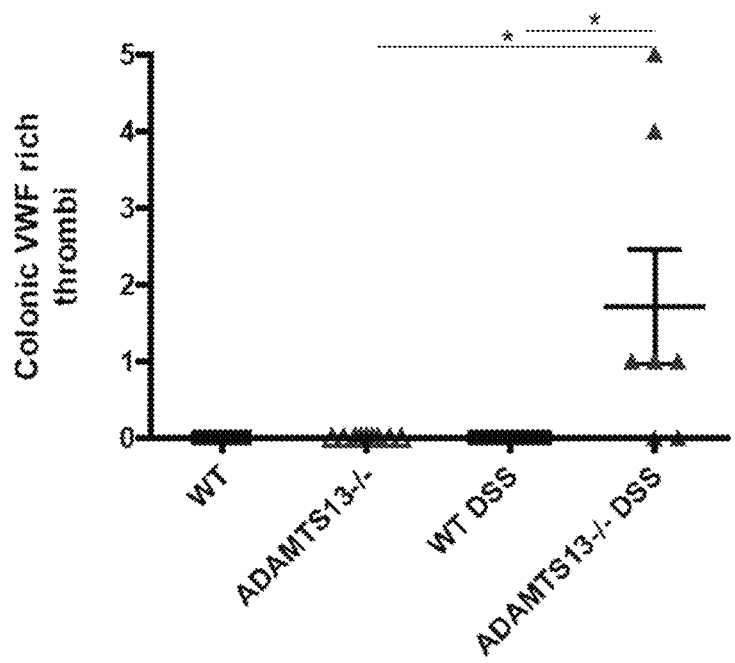

Thrombocytosis is marker of colonic inflammation and is seen in colitis in mice and humans.[8,32] Platelet counts were evaluated in WT and ADAMTS13$^{-/-}$ mice before and after colitis initiation. Platelet counts in WT and ADAMTS13$^{-/-}$ mice did not differ prior to colitis initiation (FIG. 12A). WT mice demonstrated the typical pattern of significant thrombocytosis with DSS colitis (P<0.0005), whereas ADAMTS13$^{-/-}$ mice had no significant difference in platelet count after the development of colitis (P=0.12). In fact, ADAMTS13$^{-/-}$ with the most severe colitis phenotype tended to be more thrombocytopenic (FIG. 21B). This finding led to investigation of whether in ADAMTS13$^{-/-}$ mice platelets were consumed in colonic thrombi. Entire Swiss rolled colons were immunofluorescently stained for VWF and endothelial cells for PECAM-1 (CD31) to identify vessels. In a majority of ADAMTS13$^{-/-}$ mice with colitis, we found one or more sub-mucosal vessel(s) completely occluded by a VWF-rich thrombus, compared to WT where none were found (FIG. 12C, P<0.05). Notably, in colons from WT and ADAMTS13$^{-/-}$ mice without colitis we found no sub-mucosal thrombi. Taken together, these results indicate that, through accumulation of ULVWF in the colonic vessels, ADAMTS13 deficiency worsens colitis by inducing local inflammation and thrombosis.

WT and ADAMTS13$^{-/-}$ Mice Show Prominent Subendothelial VWF Staining in Inflamed Colonic Tissue.

Circulating VWF could be a marker of increased endothelial activation and inflammation in colitis and also serve as an indicator of ADAMTS13 activity. To further characterize these in murine colitis, plasma VWF was quantified at baseline and at day 10 of colitis. As we expected, DSS colitis increased plasma VWF in WT mice but also in ADAMTS13$^{-/-}$ mice. However, VWF increased significantly more in WT than in ADAMTS13$^{-/-}$ mice (FIG. 13A) perhaps indicating that ULVWF was in part retained in the ADAMTS13$^{-/-}$ mouse colons.

Figure 13A:
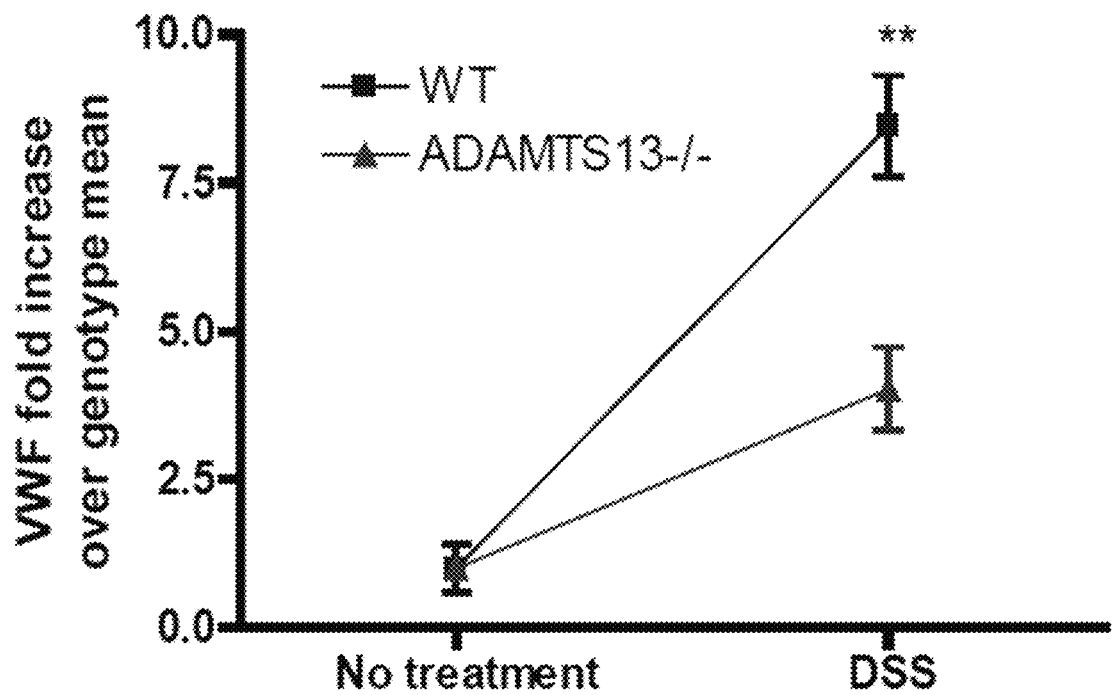
FIGS. 13A-13B demonstrate that colitis causes massive VWF release.
Figure 13B:
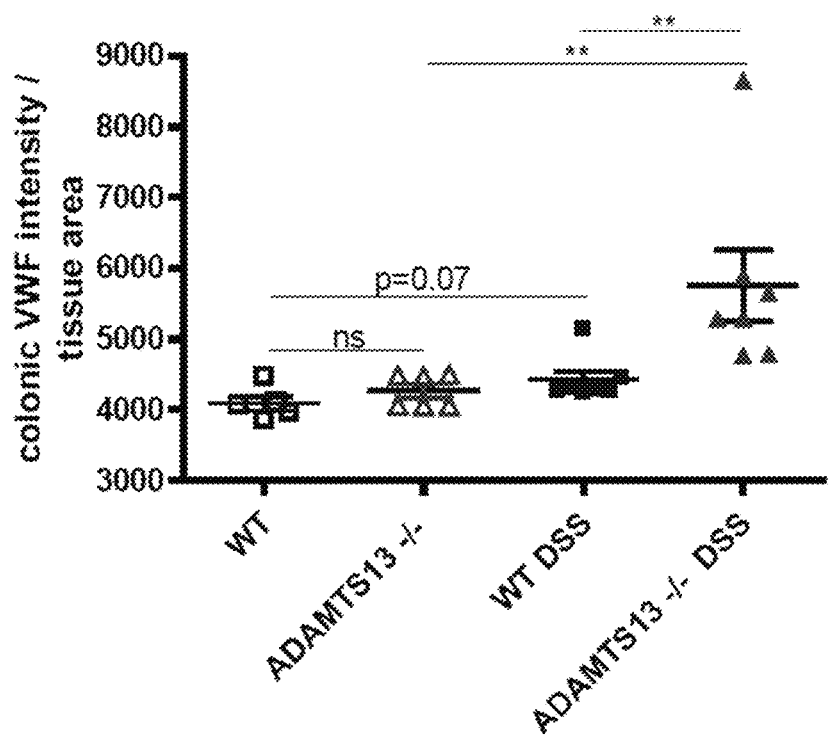

Colons from WT and ADAMTS13-/- mice without colitis were immunofluorescently stained for VWF. In WT mice, VWF staining was in a dotted pattern and was closely associated with PECAM-1 positive endothelium thus suggesting it was still contained in Weibel-Palade bodies (data not shown). In contrast, both WT and ADAMTS13-/- mice with colitis had increased areas of VWF stained colonic tissue extending beyond PECAM-1 positive vessels into the subendothelial space (data not shown). Colonic sections were assessed by an observer blinded to mouse genotype for VWF immunofluorescent intensity. There was more intense VWF staining in colonic tissue from ADAMTS13−/− mice compared to WT mice with colitis (P=0.0023, FIG. 13B). VWF intensity in ADAMTS13−/− mice increased significantly over baseline (P=0.0012), while WT showed a tendency to increase VWF tissue intensity (P=0.07). Notably, VWF intensity in colonic tissue did not significantly differ at baseline between WT and ADAMTS13−/− mice (P=0.43). This apparent retention of released VWF in inflamed tissue together with thrombi formation may explain the relatively lower increase of plasma VWF in colitis in the ADAMTS13−/− mice compared to WT mice (FIG. 13A).

Increased VWF Release in Colon Tissue is Seen in Other Murine Colitis Models and in Human Colitis Specimens.

In the DSS colitis model acute colonic injury leads to development of inflammation, mainly a Th1 mediated response,[33] which is immunologically distinct from chronic colitis models and relapsing and remitting human disease. Despite this distinction, it was investigated whether increased colonic VWF release may also occur in additional immune-mediated colitis models and in human colitis. Indeed, prominent VWF staining was found in colitic tissue from several chronic colitis models. Interstitial VWF release seemed more pronounced in models with a more severe colitis phenotype. Most notably the WT CD4 T cell transfer into Rag2−/− model has a mild colitis phenotype without any weight loss 4 weeks post transfer and minimally increased colitis scores.[26] In this model, there was minimally increased colonic VWF staining compared to control WT colons and staining was contained within vessel walls (data not shown). Similarly, slightly increased VWF staining was observed in the IL10 receptor β (Il10rb)−/− mice which have a mild phenotype with colitis development after 15 weeks.[34] In contrast, when these two genotypes are combined, WT CD4 T cell transfer into Rag2−/− Il10rb−/− mice have 20% weight loss 4 weeks post transfer and colitis scores that are six times worse than the WT CD4 T cell transfer into Rag2−/−.[26] Colons from these more severely affected mice showed extensive and intense VWF staining (data not shown). Mice deficient in Wiskott Aldrich Syndrome protein (WAS) develop severe colonic inflammation by the age of 12 to 16 weeks with mixed Th1 and Th2 type responses.[27] Disease in these mice is partially driven by interleukin 4 (IL4) as deletion of IL4 improves disease in Was−/−Il4−/− mice.[27] Similar to diseaseseverity, VWF staining in colonic tissues from Was−/− mice is more pronounced compared to Was−/−Il4−/− mice, which corroborates the hypothesis (data not shown).

In human inflamed colonic tissue, similar to DSS colitis and the chronic colitis models above, increased VWF release was observed at sites of marked inflammation in comparison to healthy sites in 12 human colitis biopsy or colon resection specimens from individuals with IBD (data not shown). Staining was both intravascular and extravascular with VWF extending into colon tissue (data not shown). Taken together, these results indicate that even without ADAMTS13-deficiency, colitis induces the release of VWF in inflamed colons and this increases with the severity of the disease.

Treatment of WT Mice with DSS Colitis with rhADAMTS13 Reduces Clinical Colitis Severity.

Figure 14A:
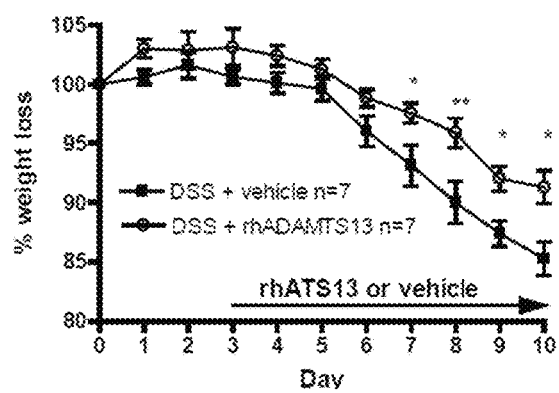
FIGS. 14A-14F demonstrate that treatment of WT mice with rhADAMTS13 improves outcome.
Figure 14B:
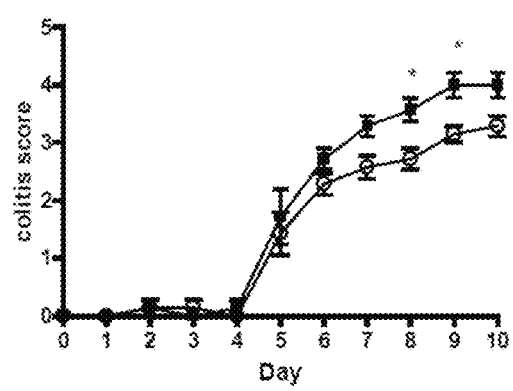
Figure 14C:
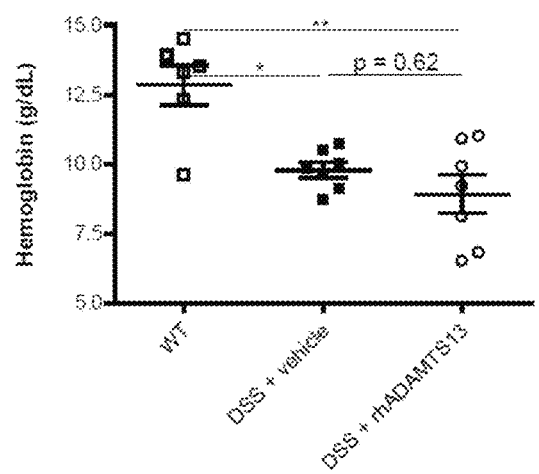
Figure 14D:
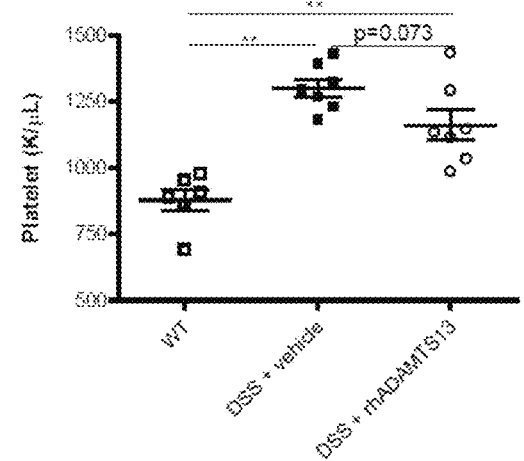
Figure 14E:
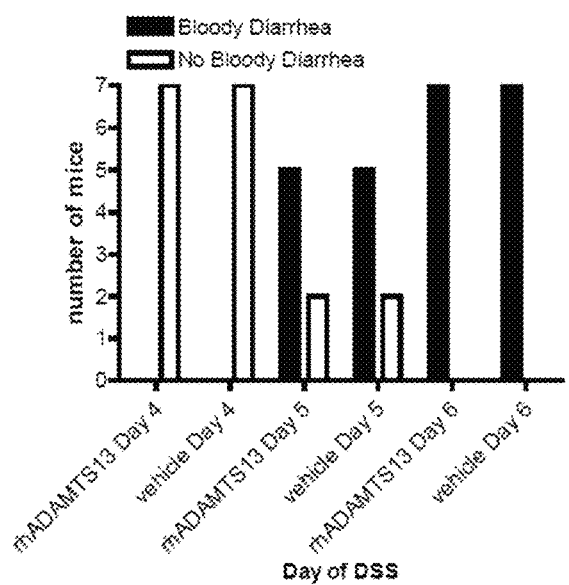

Since colitis is worse in mice in the absence of ADAMTS13, and colitic WT mice had highly increased VWF release in both plasma (FIG. 13A) and in inflamed colonic tissue (FIG. 13B), it was hypothesized that systemic administration of rhADAMTS13 to supplement endogenous ADAMTS13 in WT mice would reduce colitis severity. rhADAMTS13 or saline vehicle was administered intravenously daily beginning on day 3 of DSS treatment, which is two days before the onset of weight loss in the DSS model. In mice treated with rhADAMTS13, less weight loss (FIG. 14A), and less severe clinical colitis scores on days 8-10 were observed than in vehicle treated mice (FIG. 14B). While the expected drop in hemoglobin typical of colitis with bloody diarrhea in DSS treated mice was observed, there was not a significant difference in hemoglobin concentrations (FIG. 14C) or onset of bloody diarrhea (FIG. 14E) between rhADAMTS13−, and vehicle-treated mice indicating an absence of excessive rectal bleeding as a result of rhADAMTS13 treatment. The expected increase in platelet counts was observed in both rhADAMTS13- and vehicle-treated groups with colitis. However, there tended to be less thrombocytosis in the rhADAMTS13 treated group (FIG. 14D). Significant differences were not found between rhADAMTS13- and vehicle-treated groups with respect to colon length, scores of microscopic inflammation of H&E stained colon sections, VWF colon staining, plasma VWF or spleen weight (data not shown).

Figure 14F:
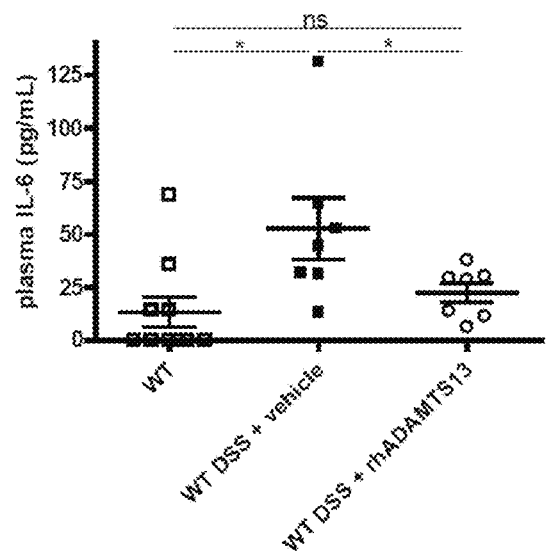
Figure 15A:
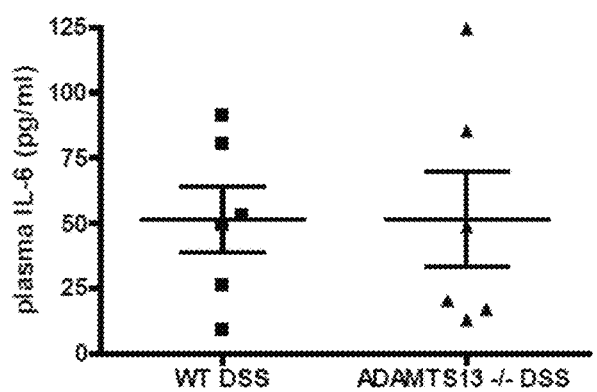
FIG. 15A depicts a graph demonstrating that plasma IL-6 did not differ between WT and ADAMTS13−/− mice. There were no differences in plasma sPsel (FIG. 15B), TAT (FIG. 15C), or IL-10 (FIG. 15D) between WT and ADAMTS13−/− mice with DSS colitis or between vehicle or rhADAMTS13 treated WT mice.
Figure 15B:
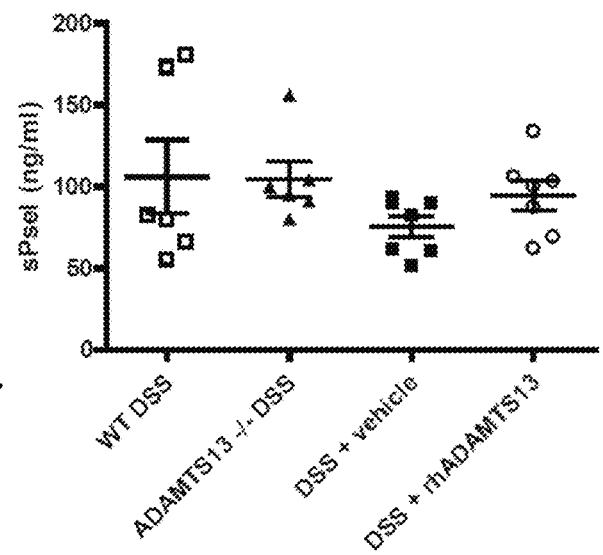
Figure 15C:
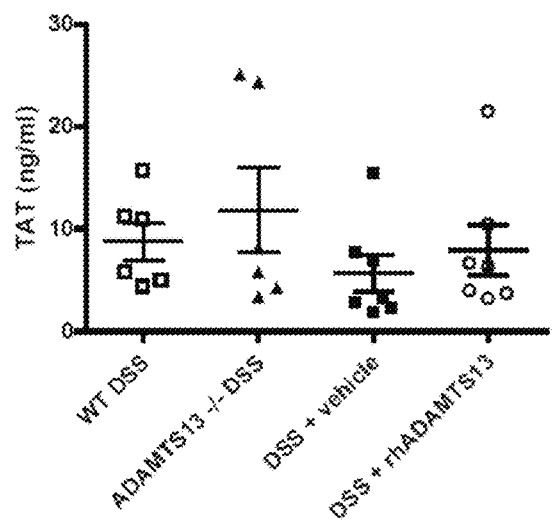
Figure 15D:
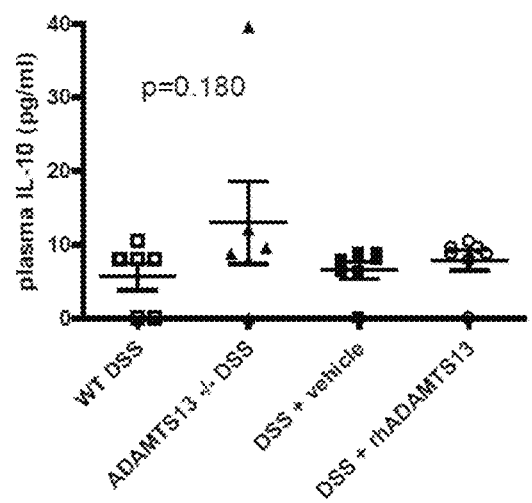

No differences in IL10, TAT, or sPsel were detected between rhADAMTS13− and vehicle-treated mice (FIGS. 15B-15D). However, administration of rhADAMTS13 resulted in lower IL-6 levels in plasma (FIG. 14F). IL-6 is a pathologically important cytokine in human and murine colitis.[35] It is both pro-inflammatory and prothrombotic, as it enhances platelet activation and aggregation, increases platelet leukocyte aggregates, and accelerates thrombopoiesis in DSS colitis.[32,35] This finding can account for part of the beneficial effect of rhADAMT13 in the treated mice (FIG. 14A-14B).

DISCUSSION

Demonstrated herein is an important protective role of ADAMTS13 in colitis and an additional mechanism linking thrombosis and inflammation in IBD. Decreased ADAMTS13 activity in IBD can contribute to the increased rates of thrombosis in this condition and also worsen colonic inflammation through decreased ULVWF degradation and clearance from colonic endothelium. The work described herein indicates a mechanism whereby colonic inflammation releases ULVWF that, when uncut by ADAMTS13, entangles platelets resulting in the formation of VWF rich thrombi in submucosal vessels. These thrombi then further worsen disease similar to what we saw in the ADAMTS13−/− mice.

Increased VWF release was found with colonic inflammation in murine DSS colitis, in several models of chronic murine colitis, and in inflamed human colon tissue samples. ULVWF release was most marked at ulcerated sites. Multiple factors may contribute to endothelial activation in colitis including localized hypoxia, activated platelets, circulating platelet leukocyte aggregates, circulating immune complexes, and cytokines,[39,40] all of which could lead to Weibel-Palade body release of ULVWF. When ULVWF is left uncut by ADAMTS13, excess platelet and leukocyte recruitment worsens inflammation and can lead to thrombosis.[19,41] Microvascular and submucosal thrombosis may then further worsen inflammation through tissue hypoxia, resulting ROS production, and more tissue injury.

Increased vascular permeability is a feature of colitis[22] and likely results from a combination of factors some of which are mentioned above. Thioglycollate peritonitis leads to increased vascular permeability of mesenteric vessels.[42] In this model, antibody blockade of VWF and platelet depletion both significantly decrease vascular permeability.[42] Our group has also observed that VWF release under inflammatory conditions increases the permeability of cerebral vessels. 43

Excess VWF and platelets in colonic vessels may contribute to the worse phenotype found in ADAMTS13−/− mice. More VWF staining was also found in inflamed human tissue specimens from patients with IBD compared to tissue from healthy controls.

Described herein is prominent VWF staining in several chronic murine colitis models. In these models, the severity of the colitis phenotype seem to parallel the amount of VWF staining present. Similar to the human specimens, more VWF release was seen in more severely affected sites. These results indicate a generalizability of the findings, beyond the acute DSS colitis chemical injury model, to diseases of chronic intestinal inflammation which involve both the innate and adaptive immune systems and repeated immune injury and tissue remodeling.

Without wishing to be bound by theory, it is contemplated herein that the marked increase in plasma VWF observed in WT mice compared to ADAMTS13−/− mice occurred because more VWF was sequestered in the inflamed colons of ADAMTS13−/− mice and not released into circulation by ADAMTS13 cleavage. This VWF may remain attached to the inflamed vessels or to micro-thrombi formed by activated platelets. The present findings in both WT and ADAMTS13−/− mice with colitis agree with observations in human subjects where high circulating VWF levels are found with active colitis.[20]

Patients with IBD develop extra-intestinal thrombosis especially when their disease is active. They have higher levels of circulating platelet leukocyte aggregates compared to both healthy and inflamed controls.[49] Circulating VWF multimers bound with activated platelets, and platelet leukocyte aggregates could also be a nidus for thrombosis at extra-intestinal sites and/or contribute to systemic endothelial activation. VWF represents an intriguing biomarker which could be measured in patients with IBD as an indicator of both disease activity and thrombotic risk. Described herein is marked VWF release in tissue from patients with active IBD.

High circulating VWF and decreased ADAMTS13 activity can be used as indicators for patients who would benefit from anticoagulation- and/or rhADAMTS13 to decrease their thrombosis risk with an added anti-inflammatory effect. rhADAMTS13 represents an appealing potential anti-inflammatory treatment for colitis by decreasing platelet and leukocyte recruitment into inflamed tissue and by preventing microthrombi formation. As described herein, treatment of WT mice with rhADAMTS13 decreased colitis severity by lessening weight loss, improving clinical colitis scores, and revealed a trend towards less thrombocytosis. Importantly, despite active colonic bleeding in colitis, rhADAMTS13 treatment did not worsen anemia. Therefore, rhADAMTS13 administration did not worsen colonic bleeding, an important feature if it is to be considered as a therapeutic in colitis.

Thrombocytosis is an inflammatory marker in colitis.[8] The trend towards less thrombocytosis in rhADAMTS13 treated mice may argue for an anti-inflammatory effect. Additionally, rhADAMTS13 treatment resulted in a reduction of plasma IL-6. IL-6 is a pro-inflammatory cytokine associated in both murine and human colitis.[50] IL-6 increases platelet production and these newly formed platelets are more thrombogenic.[10,51] Intermittent ischemia and reperfusion occur in the affected areas of the colon. rhADAMTS13 treatment improves ischemia/reperfusion injury in animal models of stroke[52] and myocardial infarction[29,53] in part by reducing leukocyte recruitment. These examples support another potential anti-inflammatory mechanism for rhADAMTS13 in colitis.

The present findings indicate that VWF and ADAMTS13 play significant roles in modulating colitis. Elevated plasma VWF and decreased ADAMTS13 levels or activity are intriguing biomarkers of inflamed endothelium and thrombotic risk in patients with IBD. ADAMTS13 deficiency is deleterious in colitis and rhADAMTS13 had anti-inflammatory effects without worsening colonic bleeding.

REFERENCES

1. Kappelman M D, Moore K R, Allen J K, Cook S F. Recent trends in the prevalence of Crohn's disease and ulcerative colitis in a commercially insured U S population. *Dig Dis Sci.* 2013; 58(2):519-525.
2. Xavier R J, Podolsky D K. Unravelling the pathogenesis of inflammatory bowel disease. *Nature.* 2007; 448(7152): 427-434.
3. Bernstein C N, Blanchard J F, Houston D S, Wajda A. The incidence of deep venous thrombosis and pulmonary embolism among patients with inflammatory bowel disease: a population-based cohort study. *Thromb Haemost.* 2001; 85(3):430-434.
4. Zitomersky N L, Verhave M, Trenor C C, 3rd. Thrombosis and inflammatory bowel disease: a call for improved awareness and prevention. *Inflamm Bowel Dis.* 2011; 17(1):458-470.
5. Ha C, Magowan S, Accortt N A, Chen J, Stone C D. Risk of arterial thrombotic events in inflammatory bowel disease. *Am J Gastroenterol.* 2009; 104(6): 1445-1451.
6. Ozturk K, Guler A K, Cakir M, et al. Pulse Wave Velocity, Intima Media Thickness, and Flow-mediated Dilatation in Patients with Normotensive Normoglycemic Inflammatory Bowel Disease. *Inflamm Bowel Dis.* 2015.
7. Danese S, Papa A, Saibeni S, Repici A, Malesci A, Vecchi M. Inflammation and coagulation in inflammatory bowel disease: The clot thickens. *Am J Gastroenterol.* 2007; 102(1):174-186.
8. Harries A D, Fitzsimons E, Fifield R, Dew M J, Rhoades J. Platelet count: a simple measure of activity in Crohn's disease. *Br Med J (Clin Res Ed).* 1983; 286(6376):1476.
9. Andoh A, Yoshida T, Yagi Y, et al. Increased aggregation response of platelets in patients with inflammatory bowel disease. *J Gastroenterol.* 2006; 41(1):47-54.
10. Esmon C T. The impact of the inflammatory response on coagulation. *Thromb Res.* 2004; 114(5-6):321-327.
11. Feys H B, Canciani M T, Peyvandi F, Deckmyn H, Vanhoorelbeke K, Mannucci P M. ADAMTS13 activity to antigen ratio in physiological and pathological conditions associated with an increased risk of thrombosis. *Br J Haematol.* 2007; 138(4):534-540.
12. Ley K, Laudanna C, Cybulsky M I, Nourshargh S. Getting to the site of inflammation: the leukocyte adhesion cascade updated. *Nat Rev Immunol.* 2007; 7(9):678-689.
13. Sandborn W J, Feagan B G, Rutgeerts P, et al. Vedolizumab as induction and maintenance therapy for Crohn's disease. *N Engl J Med.* 2013; 369(8):711-721.
14. Feagan B G, Rutgeerts P, Sands B E, et al. Vedolizumab as induction and maintenance therapy for ulcerative colitis. *N Engl J Med.* 2013; 369(8):699-710.
15. Wagner D D. Cell biology of von Willebrand factor. *Annu Rev Cell Biol.* 1990; 6:217-246.
16. Sporn L A, Marder V J, Wagner D D. von Willebrand factor released from Weibel-Palade bodies binds more 16. avidly to extracellular matrix than that secreted constitutively. *Blood.* 1987; 69(5):1531-1534.
17. Arya M, Anvari B, Romo G M, et al. Ultralarge multimers of von Willebrand factor form spontaneous high-strength bonds with the platelet glycoprotein Ib-IX complex: studies using optical tweezers. *Blood.* 2002; 99(11): 3971-3977.
18. Dong J F, Moake J L, Nolasco L, et al. ADAMTS-13 rapidly cleaves newly secreted ultralarge von Willebrand factor multimers on the endothelial surface under flowing conditions. *Blood.* 2002; 100(12):4033-4039.
19. Chauhan A K, Kisucka J, Brill A, Walsh M T, Scheiflinger F, Wagner D D. ADAMTS13: a new link between thrombosis and inflammation. *J Exp Med.* 2008; 205(9): 2065-2074.
20. Stevens T R, James J P, Simmonds N J, et al. Circulating von Willebrand factor in inflammatory bowel disease. *Gut.* 1992; 33(4):502-506.
21. Zezos P, Papaioannou G, Nikolaidis N, Vasiliadis T, Giouleme O, Evgenidis N. Elevated plasma von Willebrand factor levels in patients with active ulcerative colitis reflect endothelial perturbation due to systemic inflammation. *World J Gastroenterol.* 2005; 11(48):7639-7645.
22. Mori M, Salter J W, Vowinkel T, Krieglstein C F, Stokes K Y, Granger D N. Molecular determinants of the prothrombogenic phenotype assumed by inflamed colonic venules. *Am J Physiol Gastrointest Liver Physiol.* 2005; 288(5):G920-926.
23. Vowinkel T, Wood K C, Stokes K Y, et al. Mechanisms of platelet and leukocyte recruitment in experimental colitis. *Am J Physiol Gastrointest Liver Physiol.* 2007; 293(5):G1054-1060.
24. Chauhan A K, Walsh M T, Zhu G, Ginsburg D, Wagner D D, Motto D G. The combined roles of ADAMTS13 and VWF in murine models of TTP, endotoxemia, and thrombosis. *Blood.* 2008; 111(7):3452-3457.
25. Motto D G, Chauhan A K, Zhu G, et al. Shigatoxin triggers thrombotic thrombocytopenic purpura in genetically susceptible ADAMTS13-deficient mice. *J Clin Invest.* 2005; 115(10):2752-2761.
26. Shouval D S, Biswas A, Goettel J A, et al. Interleukin-10 receptor signaling in innate immune cells regulates mucosal immune tolerance and anti-inflammatory macrophage function. *Immunity.* 2014; 40(5):706-719.
27. Nguyen D D, Maillard M H, Cotta-de-Almeida V, et al. Lymphocyte-dependent and Th2 cytokine-associated colitis in mice deficient in Wiskott-Aldrich syndrome protein. *Gastroenterology.* 2007; 133(4):1188-1197.
28. Wirtz S, Neurath M F. Mouse models of inflammatory bowel disease. *Adv Drug Deliv Rev.* 2007; 59(11): 1073-1083.
29. Savchenko A S, Borissoff J I, Martinod K, et al. VWF-mediated leukocyte recruitment with chromatin decondensation by PAD4 increases myocardial ischemia/reperfusion injury in mice. *Blood.* 2014a; 123(1):141-148.
30. Brill A, Fuchs T A, Chauhan A K, et al. von Willebrand factor-mediated platelet adhesion is critical for deep vein thrombosis in mouse models. *Blood.* 2011; 117(4):1400-1407.
31. Mizoguchi E. Chitinase 3-like-1 exacerbates intestinal inflammation by enhancing bacterial adhesion and invasion in colonic epithelial cells. *Gastroenterology.* 2006; 130(2):398-411.
32. Yan S L, Russell J, Harris N R, Senchenkova E Y, Yildirim A, Granger D N. Platelet abnormalities during colonic inflammation. *Inflamm Bowel Dis.* 2013; 19(6):1245-1253.
33. Alex P, Zachos N C, Nguyen T, et al. Distinct cytokine patterns identified from multiplex profiles of murine DSS and TNBS-induced colitis. *Inflamm Bowel Dis.* 2009; 15(3):341-352.
34. Spencer S D, Di Marco F, Hooley J, et al. The orphan receptor CRF2-4 is an essential subunit of the interleukin 10 receptor. *J Exp Med.* 1998; 187(4):571-578.
35. Senchenkova E Y, Komoto S, Russell J, et al. Interleukin-6 mediates the platelet abnormalities and thrombogenesis associated with experimental colitis. *Am J Pathol.* 2013; 183(1):173-181.
36. Dhillon A P, Anthony A, Sim R, et al. Mucosal capillary thrombi in rectal biopsies. *Histopathology.* 1992; 21(2): 127-133.
37. Violi N V, Schoepfer A M, Fournier N, et al. Prevalence and clinical importance of mesenteric venous thrombosis in the Swiss Inflammatory Bowel Disease Cohort. *AJR Am J Roentgenol.* 2014; 203(1):62-69.
38. Papay P, Miehsler W, Tilg H, et al. Clinical presentation of venous thromboembolism in inflammatory bowel disease. *J Crohns Colitis.* 2013; 7(9):723-729.
39. Wagner D D, Frenette P S. The vessel wall and its interactions. *Blood.* 2008; 111(11):5271-5281.
40. Bernardo A, Ball C, Nolasco L, Moake J F, Dong J F. Effects of inflammatory cytokines on the release and cleavage of the endothelial cell-derived ultralarge von Willebrand factor multimers under flow. *Blood.* 2004; 104(1):100-106.
41. Goerge T, Ho-Tin-Noe B, Carbo C, et al. Inflammation induces hemorrhage in thrombocytopenia. *Blood.* 2008; 111(10):4958-4964.
42. Petri B, Broermann A, Li H, et al. von Willebrand factor promotes leukocyte extravasation. *Blood.* 2010; 116(22): 4712-4719.
43. Suidan G L, Brill A, De Meyer S F, et al. Endothelial Von Willebrand factor promotes blood-brain barrier flexibility and provides protection from hypoxia and seizures in mice. *Arterioscler Thromb Vasc Biol.* 2013; 33(9):2112-2120.
44. Middleton J, Americh L, Gayon R, et al. A comparative study of endothelial cell markers expressed in chronically inflamed human tissues: MECA-79, Duffy antigen receptor for chemokines, von Willebrand factor, CD31, CD34, CD105 and C D 146. *J Pathol.* 2005; 206(3):260-268.
45. Matsumoto T, Kitano A, Nakamura S, et al. Possible role of vascular endothelial cells in immune responses in colonic mucosa examined immunocytochemically in subjects with and without ulcerative colitis. *Clin Exp Immunol.* 1989; 78(3):424-430.
46. Ippolito C, Segnani C, Errede M, et al. An integrated assessment of histopathological changes of the enteric neuromuscular compartment in experimental colitis. *J Cell Mol Med.* 2015; 19(2):485-500.
47. Cromer W E, Mathis J M, Granger D N, Chaitanya G V, Alexander J S. Role of the endothelium in inflammatory bowel diseases. *World J Gastroenterol.* 2011; 17(5):578-593.
48. Thompson N P, Wakefield A J, Pounder R E. Inherited disorders of coagulation appear to protect against inflammatory bowel disease. *Gastroenterology.* 1995; 108(4): 1011-1015.
49. Irving P M, Macey M G, Shah U, Webb L, Langmead L, Rampton D S. Formation of platelet-leukocyte aggregates in inflammatory bowel disease. *Inflamm Bowel Dis.* 2004; 10(4):361-372.
50. Powell N, Lo J W, Biancheri P, et al. Interleukin-6 Increases Production of Cytokines by Colonic Innate Lymphoid Cells in Mice and Patients with Chronic Intestinal Inflammation. *Gastroenterology.* 2015; 149(2):456-6.
51. Burstein S A. Cytokines, platelet production and hemostasis. *Platelets.* 1997; 8(2-3):93-104.
52. Khan M M, Motto D G, Lentz S R, Chauhan A K. ADAMTS13 reduces VWF-mediated acute inflammation following focal cerebral ischemia in mice. *J Thromb Haemost.* 2012; 10(8):1665-1671.
53. De Meyer S F, Savchenko A S, Haas M S, et al. Protective anti-inflammatory effect of ADAMTS13 on myocardial ischemia/reperfusion injury in mice. *Blood.* 2012; 120(26):5217-5223.

What is claimed herein is:

1. A method of treating preeclampsia in a subject in need of treatment therefor, the method comprising administering to the subject an ADAMTS13 polypeptide or a recombinant ADAMTS13 polypeptide;
   wherein the ADAMTS13 polypeptide or the recombinant ADAMTS13 polypeptide comprises a sequence at least 95% identical to SEQ ID NO: 2 and which retains the activity of SEQ ID NO: 2;
   wherein the subject is a subject determined to have an elevated level of expression of soluble VEGF receptor 1 (soluble fms-like tyrosine kinase 1; sFlt-1); and
   whereby the blood pressure of the subject is improved.

2. The method of claim 1, wherein the subject is a subject determined to have a reduced level of expression and/or activity of ADAMTS13.

3. The method of claim 1, wherein the subject is being treated with a VEGF inhibitor.

4. The method of claim 3, wherein the VEGF inhibitor is selected from the group consisting of:
   bevacizumab; sunitinib; aflibercept; pazopanib; axitinib; sorafenib; vandetanib;
   regorafenib; and ramucirumab.

5. The method of claim 1, wherein the ADAMTS13 polypeptide or the recombinant ADAMTS13 polypeptide comprises the sequence of SEQ ID NO: 2.

* * * * *